US011925683B2

(12) United States Patent
Straub et al.

(10) Patent No.: US 11,925,683 B2
(45) Date of Patent: *Mar. 12, 2024

(54) COMPOSITIONS FOR MAKING AND USING ANTI-MYOSTATIN ANTIBODIES

(71) Applicant: SCHOLAR ROCK, INC., Cambridge, MA (US)

(72) Inventors: Michelle Straub, Yarmouth, ME (US); Dong Yun Lee, Boston, MA (US); William K. McConaughy, Boston, MA (US); Katherine Jane Turner, Acton, MA (US); Nagesh K. Mahanthappa, Cambridge, MA (US); Justin W. Jackson, Cambridge, MA (US)

(73) Assignee: Scholar Rock, Inc., Cambridge, MA (US)

( * ) Notice: Subject to any disclaimer, the term of this patent is extended or adjusted under 35 U.S.C. 154(b) by 212 days.

This patent is subject to a terminal disclaimer.

(21) Appl. No.: 17/446,897

(22) Filed: Sep. 3, 2021

(65) Prior Publication Data

US 2022/0152200 A1 May 19, 2022

Related U.S. Application Data

(63) Continuation of application No. 16/374,854, filed on Apr. 4, 2019, now Pat. No. 11,135,291, which is a continuation of application No. 15/524,651, filed as application No. PCT/US2015/059468 on Nov. 6, 2015, now Pat. No. 10,307,480.

(60) Provisional application No. 62/219,094, filed on Sep. 15, 2015, provisional application No. 62/187,348, filed on Jul. 1, 2015, provisional application No. 62/100,361, filed on Jan. 6, 2015, provisional application No. 62/076,230, filed on Nov. 6, 2014.

(51) Int. Cl.
| | | |
|---|---|---|
| *C07K 16/22* | (2006.01) | |
| *A61K 39/395* | (2006.01) | |
| *G01N 33/53* | (2006.01) | |
| *G01N 33/74* | (2006.01) | |
| *A61K 39/00* | (2006.01) | |
| *C07K 14/475* | (2006.01) | |

(52) U.S. Cl.
CPC .... *A61K 39/39533* (2013.01); *A61K 39/3955* (2013.01); *C07K 16/22* (2013.01); *G01N 33/53* (2013.01); *G01N 33/74* (2013.01); *A61K 2039/505* (2013.01); *C07K 14/475* (2013.01); *C07K 2317/21* (2013.01); *C07K 2317/30* (2013.01); *C07K 2317/33* (2013.01); *C07K 2317/622* (2013.01); *C07K 2317/76* (2013.01); *C07K 2317/92* (2013.01); *C07K 2317/94* (2013.01); *G01N 2800/10* (2013.01)

(58) Field of Classification Search
CPC ..... C07K 16/22; A61K 39/3955; G01N 33/53
See application file for complete search history.

(56) References Cited

U.S. PATENT DOCUMENTS

| | | |
|---|---|---|
| 6,096,506 A | 8/2000 | Lee et al. |
| 6,656,475 B1 | 12/2003 | Lee et al. |
| 6,858,208 B2 | 2/2005 | Lee et al. |
| 7,138,501 B2 | 11/2006 | Ruben et al. |
| 7,566,768 B1 | 7/2009 | Lee et al. |
| 10,287,345 B2 | 5/2019 | Donovan et al. |
| 10,307,480 B2 | 6/2019 | Straub et al. |
| 10,751,413 B2 | 8/2020 | Carven et al. |
| 10,882,904 B2 | 1/2021 | Donovan et al. |
| 10,946,036 B2 | 3/2021 | Long et al. |
| 11,135,291 B2 | 10/2021 | Straub et al. |
| 11,155,611 B2 | 10/2021 | Donovan et al. |
| 11,439,704 B2 | 9/2022 | Carven et al. |
| 2002/0157126 A1 | 10/2002 | Lee et al. |
| 2003/0167492 A1 | 9/2003 | Lee et al. |
| 2005/0049402 A1 | 3/2005 | Babcook et al. |
| 2005/0143306 A1 | 6/2005 | Junker et al. |
| 2006/0025340 A1 | 2/2006 | Knopf et al. |
| 2006/0216279 A1 | 9/2006 | Glass et al. |
| 2006/0263354 A1 | 11/2006 | Chin et al. |
| 2007/0087000 A1 | 4/2007 | Walsh et al. |
| 2007/0178095 A1 | 8/2007 | Smith et al. |
| 2007/0218067 A1 | 9/2007 | Buttner et al. |
| 2008/0119426 A1 | 5/2008 | Dale |
| 2008/0213251 A1 | 9/2008 | Sexton et al. |
| 2008/0299126 A1 | 12/2008 | Han et al. |
| 2009/0131638 A1 | 5/2009 | Davies et al. |
| 2009/0148436 A1 | 6/2009 | Lavallie et al. |
| 2009/0324590 A1 | 12/2009 | Kambadur et al. |
| 2010/0080811 A1 | 4/2010 | Davies et al. |
| 2010/0087631 A1 | 4/2010 | Han et al. |
| 2010/0166764 A1 | 7/2010 | Sayers et al. |
| 2010/0183616 A1 | 7/2010 | Green et al. |

(Continued)

FOREIGN PATENT DOCUMENTS

| | | |
|---|---|---|
| AU | 2011244851 A1 | 11/2011 |
| EP | 2853898 A1 | 4/2015 |

(Continued)

OTHER PUBLICATIONS

Castellana et al, 2011. Proteomics. 11(3): 395-405.*
Chen Declaration filed in opposition of EP Patent No. 3368069 on Apr. 27, 2022 ( 2pgs.).
Cure SMA Presentation filed in opposition of EP Patent No. 3368069 on Apr. 27, 2022 (86 pgs.).
Hori et al. (2022) "Elimination of plasma soluble antigen in cynomolgus monkeys by combining pH-dependent antigen binding and novel Fc engineering" MAbs. 14(1):2068213. doi: 10.1080/19420862.2022.2068213.
Jarecki Declaration filed in opposition of EP Patent No. 3368069 on Apr. 27, 2022 (2 pgs.).

(Continued)

*Primary Examiner* — Zachary C Howard
(74) *Attorney, Agent, or Firm* — Finnegan, Henderson, Farabow, Garrett, & Dunner, LLP

(57) ABSTRACT

Aspects of the present disclosure relate to antibodies that specifically bind proMyostatin and/or latent Myostatin and uses thereof.

9 Claims, 29 Drawing Sheets

Specification includes a Sequence Listing.

(56) References Cited

U.S. PATENT DOCUMENTS

| | | |
|---|---|---|
| 2010/0221777 A1 | 9/2010 | Choe et al. |
| 2010/0331252 A1 | 12/2010 | Hamrick |
| 2011/0165175 A1 | 7/2011 | Linhard et al. |
| 2011/0239317 A1 | 9/2011 | Lee et al. |
| 2011/0256132 A1 | 10/2011 | Ashman et al. |
| 2011/0293630 A1 | 12/2011 | Stitt et al. |
| 2013/0065820 A1 | 3/2013 | Bower et al. |
| 2013/0209489 A1 | 8/2013 | Han et al. |
| 2013/0216548 A1 | 8/2013 | Neijssen et al. |
| 2013/0230515 A1 | 9/2013 | Han et al. |
| 2013/0336982 A1 | 12/2013 | Mader et al. |
| 2014/0017262 A1 | 1/2014 | Sanicola-Nadel et al. |
| 2014/0023638 A1 | 1/2014 | Lavallie et al. |
| 2016/0199458 A1 | 7/2016 | Knopf et al. |
| 2017/0198032 A1 | 7/2017 | Donovan et al. |
| 2017/0333558 A1 | 11/2017 | Straub et al. |
| 2021/0046180 A1 | 2/2021 | Carven et al. |
| 2021/0283166 A1 | 9/2021 | Long et al. |
| 2021/0332117 A1 | 10/2021 | Donovan et al. |

FOREIGN PATENT DOCUMENTS

| | | |
|---|---|---|
| EP | 3922645 | 12/2021 |
| JP | 2003-520839 | 7/2003 |
| JP | 2004-504826 | 2/2004 |
| JP | 2009-545313 | 12/2009 |
| JP | 2010-502633 | 1/2010 |
| JP | 2012-520887 | 9/2012 |
| JP | 2017536354 | 12/2017 |
| WO | WO 1996/001845 A2 | 1/1996 |
| WO | WO2001-055029 A1 | 8/2001 |
| WO | WO 2002/009641 A2 | 2/2002 |
| WO | WO 2002/085306 A2 | 10/2002 |
| WO | WO 2003/027248 A2 | 4/2003 |
| WO | WO 2004/009776 A2 | 1/2004 |
| WO | WO 2004/024890 A2 | 3/2004 |
| WO | WO 2004/037861 A2 | 5/2004 |
| WO | WO 2005/066204 A2 | 7/2005 |
| WO | WO 2005/084699 A1 | 9/2005 |
| WO | WO 2005/103081 A2 | 11/2005 |
| WO | WO 2005/115439 A2 | 12/2005 |
| WO | WO 2006/116269 A2 | 11/2006 |
| WO | WO 2007/024535 A2 | 3/2007 |
| WO | WO 2007/044411 A3 | 4/2007 |
| WO | WO 2007/047112 A2 | 4/2007 |
| WO | WO 2007/061995 A2 | 5/2007 |
| WO | WO 2008/067480 A2 | 6/2008 |
| WO | WO 2008/119426 A1 | 10/2008 |
| WO | WO 2009/038760 A2 | 3/2009 |
| WO | WO 2010/070094 A1 | 6/2010 |
| WO | WO 2010/125003 A1 | 11/2010 |
| WO | WO 2010/144452 A1 | 12/2010 |
| WO | WO 2011/122011 A2 | 10/2011 |
| WO | WO 2011/150008 A1 | 12/2011 |
| WO | WO 2012/024242 A1 | 2/2012 |
| WO | WO 2013/071056 A2 | 5/2013 |
| WO | WO 2013/072902 A1 | 5/2013 |
| WO | WO 2013/148284 A1 | 11/2013 |
| WO | WO 2013/165972 A2 | 11/2013 |
| WO | WO 2013/186719 A1 | 12/2013 |
| WO | WO 2014/074532 A2 | 5/2014 |
| WO | WO 2014/182676 A2 | 11/2014 |
| WO | WO 2015/070158 A1 | 5/2015 |
| WO | WO 2015/195094 A1 | 12/2015 |
| WO | WO 2016/073853 A1 | 5/2016 |
| WO | WO 2016/073879 A2 | 5/2016 |
| WO | WO 2016/073906 A2 | 5/2016 |
| WO | WO 2016/098357 A1 | 6/2016 |
| WO | WO 2016/168613 A1 | 10/2016 |
| WO | WO 2017/049011 A1 | 3/2017 |
| WO | WO 2017/120523 A2 | 7/2017 |
| WO | WO 2018/116201 A1 | 6/2018 |

OTHER PUBLICATIONS

Jobling et al. (2006) "Isoform-specific activation of latent transforming growth factor beta (LTGF-beta) by reactive oxygen species", Radiat Res. 166(6):839-48.

Ling et al. (2012) "Severe neuromuscular denervation of clinically relevant muscles in a mouse model of spinal muscular atrophy" Human Molecular Genetics, vol. 21, No. 1, pp. 185-195.

Opposition Pre-summons Response filed in EP Patent No. 3368069 on Apr. 27, 2022 (33 pgs.).

Bernardo et al. (2010) "Postnatal PPARdelta activation and myostatin inhibition exert distinct yet complimentary effects on the metabolic profile of obese insulin-resistant mice," PLoS One. 5(6): e11307.

Extended European Search Report in EP Application No. 21170667.6 dated Nov. 11, 2021.

Igawa et al. (2013) "Engineered Monoclonal Antibody with Novel AntigenSweeping Activity In Vivo". PLoS One 8(5):e63236.

Schoch et al., (2015) "Charge-mediated influence of the antibody variable domain on FcRn-dependent pharmacokinetics", Proceedings of the National Academy of Sciences, vol. 112, No. 19, pp. 5997-6002.

Anderson et al., (2008) "Identification of a novel pool of extracellular pro myostatin in skeletal muscle", The Journal of Biological Chemistry, 283(11):7027-7035.

Anonymous (2005) "Human Myostatin ELISA—Prodomain specific", BioVendor Laboratory Medicine, Inc., XP055100354, Retrieved from the Internet: URL:http://deltaclon.es/pdf/RD193058100.pdf (10 pgs.).

Anonymous (2017) "SC 2. Anterolateral Systems—Deficits" [online]. Retrieved from: http://www.neuroanatomy.wisc.edu/sc97/text/p2/deficits.htm; on Jul. 11, 2017 (1 page).

Anonymous (2019) "GDF-11/BMP-11 Mouse anti-Human, Clone: 743833, R&D Systems(TM)" [online]. Retrieved from: http://www.fishersci.co.uk/shop/products/gdf-11bpm-11-mouse-anti-human-clone-743833-r-d-systems/15724724; on Feb. 28, 2019 (4 pgs.).

Australian Application No. 202010134, filed Jul. 27, 2020, for Scholar Rock, Inc.: Examination Report No. 1, dated Oct. 15, 2020.

Baranello et al., (2020) "Evaluation of body composition as a potential biomarker in spinal muscular atrophy", Muscle & Nerve, 61(4):530-534.

Benatar (2007) "Lost in translation: Treatment trials in the SOD1 mouse and in human ALS", Neurobiology of Disease, 26:1-13.

Biovendor, Research and Diagnostics Products. Myostatin Propeptide Human, Chicken Polyclonal Antibody. Product Data Sheet 2 pgs. Apr. 11, 2013.

Bräuninger et al., (2003) "Epstein-Barr virus (EBV)-positive lymphoproliferations in post-transplant patients show immunoglobulin V gene mutation patterns suggesting interference of EBV with normal B cell differentiation processes", Eur J Immunol., 33(6):1593-1602.

Breitbart et al., (2013) "Highly specific detection of myostatin prodomain by an immunoradiometric sandwich assay in serum of healthy individuals and patients", PLOS One, 8(11):e80454 (10 pgs.).

Brown et al., (1996) "Tolerance of single, but not multiple, amino acid replacements in antibody VH CDR 2: a means of minimizing B cell wastage from somatic hypermutation?", J Immunol., 156(9):3285-3291.

Burch et al., (2017) "Reduced serum myostatin concentrations associated with genetic muscle disease progression", Journal of Neurology, 264(3):541-553.

Chen et al., "Considerations for Developing Combination Therapies in SMA", Cure SMA Researcher Meeting, Jun. 16, 2016.

Ciciliot et al., (2013) "Muscle type and fiber type specificity in muscle wasting", Int J Biochem Cell Biol., 45(10):2191-2199.

Cohen et al., (2015) "Muscle wasting in disease: molecular mechanisms and promising therapies", Nat Rev Drug Discov., 14(1):58-74.

(56) References Cited

OTHER PUBLICATIONS

Cully, (2014) "Beefing up the right splice variant to treat spinal muscular atrophy". Nat Rev Drug Discov 13, 725. https://doi.org/10.1038/nrd4445 (1 pg.).
Dagbay et al., (2020) " Structural basis of specific inhibition of extracellular activation of pro- or latent myostatin by the monoclonal antibody SRK-015", J. Biol. Chem., 295(16):5404-5418.
Dalbo et al., (2017) "Testosterone and trenbolone enanthate increase mature myostatin protein expression despite increasing skeletal muscle hypertrophy and satellite cell number in rodent muscle", Andrologia, 49(3):1-11.
Day et al., (2021) "Onasemnogene abeparvovec gene therapy for symptomatic infantile-onset spinal muscular atrophy in patients with two copies of SMN2 (STR1VE): an open-label, single-arm, multicentre, phase 3 trial", Lancet Neurol, 20:284-293.
Dibernardo et al., (2006) "Translating preclinical insights into effective human trials in ALS", Biochimica et Biophysica Acta, 1762:1139-1149.
D'ydewalle et al., (2015) "Spinal muscular atrophy therapeutics: where do we stand?", Neurotherapeutics, 12(2):303-316.
Egerman et al., (2015) "GDF11 Increases with Age and Inhibits Skeletal Muscle Regeneration", Cell Metabolism, 22(1):164-174.
European Patent Application No. 16828657.3, by Scholar Rock, Inc.: Supplementary European Search Report and Opinion, dated Mar. 20, 2019.
European Patent Application No. 20179533.3, by Scholar Rock, Inc.: Partial European Search Report, dated Mar. 31, 2021 (12 pgs.).
European Patent Application No. 20193425.4, by Scholar Rock, Inc.: European Search Report, dated Apr. 1, 2021 (9 pgs.).
Farrar et al. (2017) "Emerging therapies and challenges in spinal muscular atrophy" Ann Neural 81(3): 355-368. Published online Feb. 17, 2017. doi: 10.1002/ana.24864. Publication details included.
Feng et al., (2016) "Pharmacologically induced mouse model of adult spinal muscular atrophy to evaluate effectiveness of therapeutics after disease onset", Human Molecular Genetics, 25(5):964-975.
Ferrara et al., (2015) "Recombinant renewable polyclonal antibodies", MAbs, 7(1):32-41.
Fidler, (2016) "Scholar Rock Rolls Up $36M to Move Muscle Drug to Clinical Trials" https://xconomy.com/boston/2016/01/04/scholar-rock-rolls-up-36m-to-move-muscle-drug-to-clinical-trials/.
Ge et al., (2005) "GDF11 Forms a Bone Morphogenetic Protein 1-Activated Latent Complex That Can Modulate Nerve Growth Factor-Induced Differentiation of PC12 Cells", Molecular and Cellular Biology, 25(14):5846-5858.
Giangregorio et al., (2006) "Bone Loss and Muscle Atrophy in Spinal Cord Injury: Epidemiology, Fracture Prediction, and Rehabilitation Strategies", J Spinal Cord Med., 29(5):489-500.
Gogliotti et al., (2011) "Characterization of a commonly used mouse model of SMA reveals increased seizures susceptibility and heightened fear response in FVB/N mice", Neurobiol Dis. 43(1):142-151.
Gonzalez et al., (2005) "BMP-1/Tolloid-like Metalloproteases Process Endorepellin, the Angiostatic C-terminal Fragment of Perlecan", The Journal of Biological Chemistry, 280(8):7080-7087.
Graham et al., (2015) "A Soluble Myostatin Inhibitor Does Not Prevent Sublesional Muscle Atrophy 56 Days After Spinal Cord Injury in Mice", Medicine & Science in Sports & Exercise, Abstract No. 2219:587.
Guo et al., (2009) "Myostatin Inhibition in Muscle, but Not Adippose Tissue, Decreases Fat Mass and Improves Insulin Sensitivity", PLoS One, 4(3):e4937 (11 pgs.).
Heymsfield et al., (2021) "Effect of Bimagrumab vs Placebo on Body Fat Mass Among Adults With Type 2 Diabetes and Obesity: A Phase 2 Randomized Clinical Trial", 4(1):e2033457. doi: 10.1001/jamanetworkopen.2020.33457.
Holzbaur et al., (2006) "Myostatin inhibition slows muscle atrophy in rodent models of amyotrophic lateral sclerosis", Neurobiol Dis., 23(3):697-707.

Iinternational Search Report for Application No. PCT/US2015/059557, dated May 19, 2016 (5 pgs.).
International Application No. PCT/US2016/043712, by Scholar Rock, Inc., International Search Report and Written Opinion, dated Jan. 13, 2017.
International Application No. PCT/US2017/012606, by Scholar Rock, Inc., International Search Report and Written Opinion, dated Jul. 24, 2017.
International Application No. PCT/US2017/012606, by Scholar Rock, Inc., Written Opinion dated Jan. 3, 2018 (18 pgs.).
International Application No. PCT/US2017/037332, by Scholar Rock, Inc., International Search Report and Written Opinion, dated Nov. 14, 2017.
International Application No. PCT/US2018/012686, by Scholar Rock, Inc., International Search Report and Written Opinion, dated Apr. 3, 2018.
International Preliminary Report on Patentability for Application No. PCT/US2015/059468, dated May 9, 2017 (12 pgs.).
International Preliminary Report on Patentability for Application No. PCT/US2015/059515, dated May 9, 2017 (12 pgs.).
International Preliminary Report on Patentability for Application No. PCT/US2015/059557, dated May 9, 2017 (12 pgs.).
International Preliminary Report on Patentability for Application No. PCT/US2016/052014, dated Mar. 29, 2018 (11 pgs.).
International Search Report and Written Opinion for Application No. PCT/US2016/052014, dated Jan. 9, 2017 (17 pgs.).
International Search Report for Application No. PCT/US2015/059468, dated Apr. 4, 2016 (6 pgs.).
International Search Report for Application No. PCT/US2015/059515, dated Mar. 25, 2016 (8 pgs.).
Japanese Patent Application No. 2019-517209, filed Jun. 13, 2017, by Scholar Rock, Inc., Decision to Grant a Patent, dated Dec. 8, 2020 (7 pgs.).
Jarolim et al., (2013) "2013 AACC Annual Meeting Abstracts B-175 Determination of Cardiac Troponin with a Single-Molecule High-Sensitivity Assay and Outcomes in Patients with Stable Coronary Artery Disease: Analysis from PROVE IT-TIMI 22", XP055100559, Retrieved from the Internet: URL:http://www.aacc.org/events/Annual_Meeting/abstracts/Documents/AACC_13_AM_B175-B239.pdf (22 pgs.).
Jiang et al., (2019) "Genomic analysis of a spinal muscular atrophy (SMA) discordant family identifies a novel mutation in TLL2, an activator of growth differentiation factor 8 (myostatin): a case report", BMC Medical Genetics, 20(1):204.
Kariya et al., (2014) "Requirement of enhanced Survival Motoneuron protein imposed during neuromuscular junction maturation", The Journal of Clinical Investigation, 124(2):785-800.
Latres et al., (2015) "Myostatin blockade with a fully human monoclonal antibody induces muscle hypertrophy and reverses muscle atrophy in young and aged mice", Skeletal Muscle, 5:34.
Latres et al., (2017) "Activin A more prominently regulates muscle mass in primates than does GDF8", Nature Communications, 8:15153.
Liu et al., (2014) "The Smn-Independent Beneficial Effect of Trichostatin A on an Intermediate Mouse Model of Spinal Muscular Atrophy", PLOS ONE, 9(7):e101225.(9 pgs.).
Liu et al., (2016) Activin Receptor Type 118 Inhibition Improves Muscle Phenotype and Function in a Mouse Model of Spinal Muscular Atrophy, PLoS One 11 (11):e0166803, published Nov. 21, 2016.
Loffredo et al., (2013) "Growth differentiation factor 11 is a circulating factor that reverses age-related cardiac hypertrophy", Cell, 153(4):828-839.
Long et al., (2019) "Specific inhibition of myostatin activation is beneficial in mouse models of SMA therapy", Human Molecular Genetics, 28(7):1076-1089.
Mariot et al., (2017) "Downregulation of myostatin pathway in neuromuscular diseases may explain challenges of anti-myostatin therapeutic approaches", Nature Communications, 8(1):1859.
McPherron et al., (2010) "Metabolic Functions of Myostatin and GDF11", Immunol Endocr Metab Agents Med Chem., 10(4):217-231.

(56) References Cited

OTHER PUBLICATIONS

Morrison et al., (2009) "A soluble activin type IIB receptor improves function in a mouse model of amyotrophic lateral sclerosis", Exp Neurol, 217(2):258-268.
Mosler et al., (2012) "The anabolic steroid methandienone targets the hypothalamic-pituitary-testicular axis and myostatin signaling in a rat training model", Archives of Toxicology, 86(1):109-119.
Muramatsu et al., (2021) "Novel myostatin-specific antibody enhances muscle strength in muscle disease models", Sci Rep, 11:2160, https://doi.org/10.1038/s41598-021-81669-8 (16 pgs.).
Naryshkin et al., (2014) "SMN2 splicing modifiers improve motor function and longevity in mice with spinal muscular atrophy" Science, vol. 345, Issue 6197, pp. 688-693, DOI: 10.1126/science.1250127.
Ojala et al., (2021) "In Search of a Cure: The Development of Therapeutics to Alter the Progression of Spinal Muscular Atrophy", Brain Sci., 11:194 (39 pgs.).
Opposition filed in EP Patent No. 3368069 on Apr. 28, 2021 (37 pgs.).
Opposition filed in EP Patent No. 3368069 on May 4, 2021 (89 pgs.).
Pandya et al., (2013) "Therapeutic neuroprotective agents for amyotrophic lateral sclerosis", Cell Mol Life Sci., 70(24):4729-4745.
Pirruccello-Straub et al., (2018) "Blocking extracellular activation of myostatin as a strategy for treating muscle wasting", Scientific Reports, 8(1):2292.
Pistilli et al., (2011) "Targeting Activin Type IIB Receptor to Improve Muscle Mass and Function in the mdx Mouse Model of Duchenne Muscular Dystrophy", Am J Pathol., 178(3):1287-1297.
Pubchem Substance No. CID 310264710 (trevogrumab); Create Date Feb. 5, 2016 [online]. Retrieved from: http://pubchem.ncbi.nlm.nih.gov/substance/310264710; on Feb. 5, 2020 (6 pgs.).
Reply to Examination Report dated Feb. 13, 2016 in EP Application No. 17732001.7, dated May 31, 2019.
Request for early entry and processing of EP Application No. 17732001.7, on Jun. 1, 2018.
Response to Communication dated Jul. 31, 2018 in EP Application No. 17732001.7, dated Dec. 10, 2018.
Rodino-Klapac et al., (2009) "Inhibition of myostatin with emphasis on follistatin as a therapy for muscle disease" Muscle Nerve 39(3):283-96. doi: 10.1002/mus.21244.
Roth et al., (2004) "Myostatin: a therapeutic target for skeletal muscle wasting" Curr Opin Clin Nutr Metab Care 7(3):259-63. doi: 10.1097/00075197-200405000-00004.
ScholarRock Announcement (2015) "Scholar Rock Presents First Data for Niche Modulator Inhibiting Myostatin Activation and Announces SRK-015 as Lead Drug Program" (1 pg.).
Rose et al., (2009) "Delivery of recombinant follistatin lessens disease severity in a mouse model of spinal muscular atrophy" Hum Mol Genet. Mar. 15, 2009; 18(6): 997-1005, Published online Dec. 12, 2008. doi: 10.1093/hmg/ddn426.
ScholarRock.com (2016) "Scholar Rock discovered SRK-015, a selective and local inhibitor or latent myostatin activation for the treatment of primary myopathies" (1 pg.).
Sgoutas et al., (1992) "Effect of Lyophilization on Determinations of Lipoprotein(a) in Serum", Clin Chem., 38(7):1355-1360.
Shorrock et al., (2016) "Development and Translation of Therapies for Spinal Muscular Atrophy" EMJ Neurol. 4[1]:64-73.
Singapore Patent Application No. 11201805709R, filed Jan. 6, 2017, by Scholar Rock, Inc.: International Search Report and Written Opinion, dated Oct. 11, 2019 (12 pgs.).
SMA Annual Conference "The 2016 Annual SMA Conference is here", https://www.curesma.org/the-2016-annual-sma-conference-is-here/ (3 pgs.).
SMA Researcher Meeting Summary: The Changing Landscape of SMA 2016 (5 pgs.).
Smith et al., (2013) "Myostatin inhibitors as therapies for muscle wasting associated with cancer and other disorders", Curr Opin Support Palliat Care, 7(4):352-360.
Smith et al., (2015) "Myostatin Neutralization Results in Preservation of Muscle Mass and Strength in Preclinical Models of Tumor-Induced Muscle Wasting", Mol Cancer Ther., 14(7): 1661-1670.
Spinraza (Nusinersen) FDA label, Dec. 2016 (13 pgs.).
Sumner et al. (2016) "Spinal Muscular Atrophy, Disease Mechanisms and Therapy", Academic Press, pp. 6, 15-19 and 351-356. Publication details included (22 pgs).
Sumner et al., (2009) "Inhibition of myostatin does not ameliorate disease features of severe spinal muscular atrophy mice", Human Molecular Genetics, 18(17):3145-3152.
Sumner et al., (2016) "Spinal Muscular Atrophy, Disease Mechanisms and Therapy", First edition, Academic Press, Chapters 15, 16, 21, and 23. Publication details included (91 pgs.).
Suragani et al., (2014) "Transforming growth factor-β superfamily ligand trap ACE-536 corrects anemia by promoting late-stage erythropoiesis", Nature Medicine, 20(4):408-414.
Szlama et al., (2013) "Latent myostatin has significant activity and this activity is controlled more efficiently by WFIKKN1 than by WFIKKN2", FEBS Journal, 280(16):3822-3839.
Unkown (2000) American Spinal Injury Association (ASIA) Impairment Scale, Standard Neurological Classification of Spinal Cord Injury (2 pgs.).
Unknown (2013) "Myostatin Propeptide Human, Chicken Polyclonal Antibody", BioVendor, Research and Diagnostic Products, Data Sheet (2 pgs.).
Wagner, (2020) "The elusive promise of myostatin inhibition for muscular dystrophy", Current Opinion in Neurology, 33(5):621-628.
Walker et al., Biochemistry and Biology of GDF11 and Myostatin: similarities, differences and questions for future investigation, Cir. Res. 118(7): 1125-1142, published Apr. 1, 2016.
Walter et al., (2021) "Improving Care and Empowering Adults Living with SMA: A Call to Action in the New Treatment Era", Journal of Neuromuscular Diseases, DOI 10.3233/JND-200611 (9 pgs.).
Wang (2000) "Lyophilization and development of solid protein pharmaceuticals", International Journal of Pharmaceutics, 203(1-2):1-60.
Whittemore et al., (2003) "Inhibition of myostatin in adult mice increases skeletal muscle mass and strength", Biochem Biophys Res Commun, 300(4):965-971.
Wintgens et al., (2012) "Plasma myostatin measured by a competitive ELISA using a highly specific antiserum", Clin Chim Acta., 413(15-16):1288-1294.
Wolfman et al., (2003) "Activation of latent myostatin by the BMP-1/tolloid family of metalloproteinases", Proc Natl Acad Sci U.S.A., 100(26):15842-15846.
Zhao et al., (2016) "Pharmacokinetics, pharmacodynamics, and efficacy of a small molecule SMN2 splicing modifier in mouse models of spinal muscular atrophy", Human Molecular Genetics, 25(10):1885-1899.
Amthor et al. "Lack of myostatin results in excessive muscle growth but impaired force generation," Proc Natl Acad Sci U S A. Feb. 6, 2007;104(6):1835-40.
Benjamini et al. (1991) Immunology: A Short Course, 2nd edition, p. 40 only.
Castellana et al. "Resurrection of a clinical antibody: template proteogenomic de novo proteomic sequencing and reverse engineering of an anti-lymphotoxin-α antibody", Proteomics. Feb. 2011;11(3):395-405.
Deguise et al. (2017) "New insights into SMA pathogenesis: immune dysfunction and neuroinflammation," Ann Clin Transl Neurol. 4(7):522-53.
Extended European Search Report in EP23158609.0, dated Aug. 8, 2023, 27 pages.
Jablonka et al. (2022) "Therapy development for spinal muscular atrophy: perspectives for muscular dystrophies and neurodegenerative disorders," Neurol Res Pract. 4(7):522-530.
Rindt et al. (2012) "Transgenic inactivation of murine myostatin does not decrease the severity of disease in a model of Spinal Muscular Atrophy," Neuromuscul Disord. 22(3):277-85.

(56) References Cited

OTHER PUBLICATIONS

Suh et al. (2020) "GDF11 promotes osteogenesis as opposed to MSTN, and follistatin, a MSTN/GDF11 inhibitor, increases muscle mass but weakens bone," Proc Natl Acad Sci U S A. 3;117(9):4910-4920.

* cited by examiner

■ Group 1: Vehicle Control
▨ Group 2: Ab7 (25mg/kg)
▨ Group 3: Ab1 (25mg/kg)
▨ Group 4: Ab8 (25mg/kg)
■ Group 5: Ab9 (25mg/kg)

- Group 1: Vehicle Control
- Group 2: Ab7 (25mg/kg)
- Group 3: Ab1 (25mg/kg)
- Group 4: Ab8 (25mg/kg)
- Group 5: Ab9 (25mg/kg)

- PBS
- IgG ctl (60 mg/kg/wk)
- Ab1 (60 mg/kg/wk)
- Ab1 (20 mg/kg/wk)
- Ab1 (6 mg/kg/wk)
- Ab1 (2 mg/kg/wk)

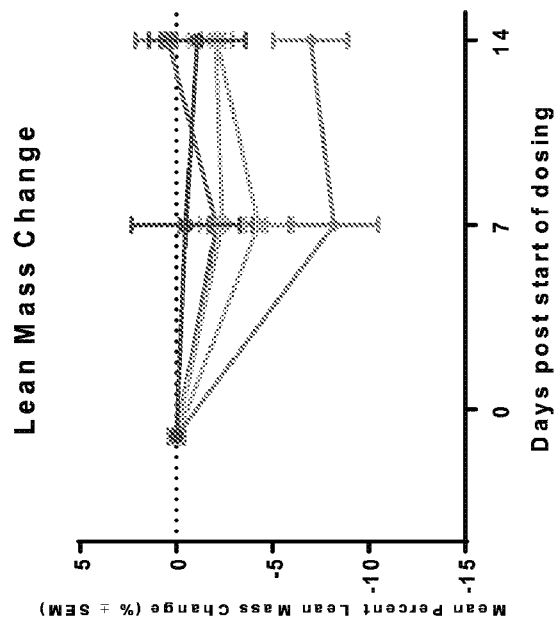
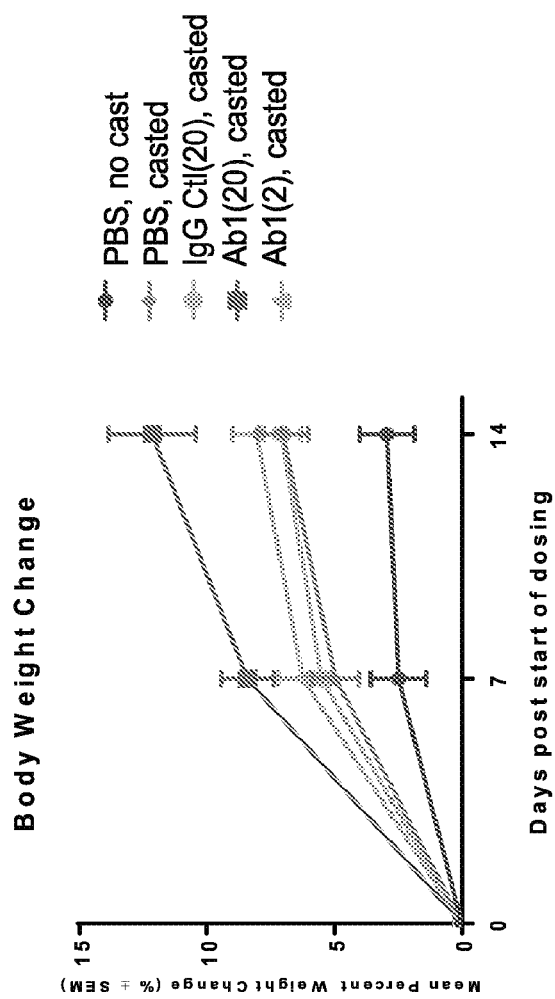
FIG. 13B
FIG. 13A

| Muscle | Ab | PBS_Ctl | 20 mg/kg/wk | 2 mg/kg/wk | 0.5 mg/kg/wk |
|---|---|---|---|---|---|
| Gastrocnemius | Ab1 | 0 | 25.1 | 13.0 | 14.9 |
| Gastrocnemius | Ab2 | 0 | 25.6 | 24.0 | 9.8 |
| Gastrocnemius | Ab4 | 0 | 25.0 | 15.0 | 3.1 |
| Gastrocnemius | Ab6 | 0 | 24.8 | 9.3 | 7.4 |
| Quadriceps | Ab1 | 0 | 23.9 | 13.9 | 10.8 |
| Quadriceps | Ab2 | 0 | 23.9 | 26.1 | 7.6 |
| Quadriceps | Ab4 | 0 | 37.8 | 6.4 | 0.2 |
| Quadriceps | Ab6 | 0 | 32.0 | 0.4 | 0.2 |

FIG. 18C

```
  1 QVQLVESGGGVVQPGRSLRLSCAASGFTFSSYGMHWVRQAPGKGLEWVAVISYDGSNKYY   60
 61 ADSVKGRFTISRDNSKNTLYLQMNSLRAEDTAVYYCARDLLVRFLEWSHYYGMDVWGQGT  120
121 TVTVSSASTKGPSVFPLAPCSRSTSESTAALGCLVKDYFPEPVTVSWNSGALTSGVHTFP  180
181 AVLQSSGLYSLSSVVTVPSSSLGTKTYTCNVDHKPSNTKVDKRVESKYGPPCPPCPAPEF  240
241 LGGPSVFLFPPKPKDTLMISRTPEVTCVVVDVSQEDPEVQFNWYVDGVEVHNAKTKPREE  300
301 QFNSTYRVVSVLTVLHQDWLNGKEYKCKVSNKGLPSSIEKTISKAKGQPREPQVYTLPPS  360
361 QEEMTKNQVSLTCLVKGFYPSDIAVEWESNGQPENNYKTTPPVLDSDGSFFLYSRLTVDK  420
421 SRWQEGNVFSCSVMHEALHNHYTQKSLSLSLG                             452
```

FIG. 21A

```
  1 QSVLTQPPSASGTPGQRVTISCSGSSSNIGSNTVHWYQQLPGTAPKLLIYSDNQRPSGVP   60
 61 DRFSGSKSGTSASLAISGLQSEDEADYYCAAWDDSLNGVFGGGTKLTVLGQPKAAPSVTL  120
121 FPPSSEELQANKATLVCLISDFYPGAVTVAWKADSSPVKAGVETTTPSKQSNNKYAASSY  180
181 LSLTPEQWKSHRSYSCQVTHEGSTVEKTVAPTECS                          215
```

FIG. 21B

Top 12 clones selected for further characterization

Ab1:          4.8 nM
Ab4:          0.47 nM      10-fold improved
Ab6:          0.48 nM      10-fold improved
Best affy matured mAb:  <10 pM     >480-fold improvement

```
              FRAMEWORK 1                CDR1           FRAMEWORK 2
Ab1    QIQLVQSGGGVVQPGRSLRLSCAASGFTFSSYGMHWVRQAPGKGLEWVA
Ab3    QIQLVQSGGGVVQPGRSLRLSCAASGF FSSYGMHWVRQAPGKGLEWVA
Ab5    QIQLVQSGGGVVQPGRSLRLSCAASGF FSSYGMHWVRQAPGKGLEWVA

CDR2              FRAMEWORK 3
Ab1    VISYDGSNKYYADSVKGRFTISRDNSKNTLYLQMNSLRAEDTAVYYCAR
Ab3    VISYDGS KYYADSVKGRFTISRDNSKNTLYLQMNSLRAEDTAVYYCAR
Ab5    VISYDG NKYYADSVKGRFTISRDNSKNTLYLQMNSLRAEDTAVYYCAR

CDR3          FRAMEWORK 4
Ab1    DLLVRFLEWSHYYGMDVWGQGTTVTVSS
Ab3    DLLVRFLEWSH YGMDVWGQGTTVTVSS
Ab5    DLLVRFLEWSH YGMDVWGQGTTVTVSS
```

FIG. 24A

```
              FRAMEWORK 1              CDR1         FRW2
Ab1    QPVLTQPPSASGTPGQRVTISCSGSSSNIGSNTVHWYQQLPGTAPKLLIY
Ab3    QPVLTQPPSASGTPGQRVTISCSGS SNIGSNTVHWYQQLPGTAPKLLIY
Ab5    QPVLTQPPSASGTPGQRVTISCSGSSSNIG NTVHWYQQLPGTAPKLLIY

CDR2            FRAMEWORK 3
Ab1    SDNQRPSGVPDRFSGSKSGTSASLVISGLQSDDEADYYC
Ab3    SD QRPSGVPDRFSGSKSGTSASLVISGLQSDDEADYYC
Ab5    SD QRPSGVPDRFSGSKSGTSASLVISGLQSDDEADYYC

CDR3      FRAMEWORK 4
Ab1    AAWDDSLNGVFGGGTKLTVL
Ab3    AAWD SLNGVFGGGTKLTVL
Ab5    AAWD SLNGVFGGGTKLTVL
```

FIG. 24B

```
                              SEQUENCE LISTING

<160> NUMBER OF SEQ ID NOS: 101

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Ser Tyr Gly Met His
1               5

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Phe Thr Phe Ser Ser Tyr Gly Met His
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Phe Ala Phe Ser Ser Tyr Gly Met His
1               5                   10

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 4

Val Ile Ser Tyr Asp Gly Ser Asn Lys Tyr Tyr Ala Asp Ser Val Lys
1               5                   10                  15

Gly

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ile Ser Tyr Asp Gly Ser Asn
1               5

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Val Ile Ser Tyr Asp Gly Ser Ile Lys Tyr Tyr Ala Asp Ser Val Lys
1               5                   10                  15

Gly

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ile Ser Tyr Asp Gly Ser Ile
1               5

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Val Ile Ser Tyr Asp Gly Asn Asn Lys Tyr Tyr Ala Asp Ser Val Lys
1               5                   10                  15

Gly

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ile Ser Tyr Asp Gly Asn Asn
```

```
1               5

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asp Leu Leu Val Arg Phe Leu Glu Trp Ser His Tyr Tyr Gly Met Asp
1               5                   10                  15

Val

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asp Leu Leu Val Arg Phe Leu Glu Trp Ser His Lys Tyr Gly Met Asp
1               5                   10                  15

Val

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ser Gly Ser Ser Ser Asn Ile Gly Ser Asn Thr Val His
1               5                   10

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ser Ser Asn Ile Gly Ser Asn Thr
1               5

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ser Gly Ser Thr Ser Asn Ile Gly Ser Asn Thr Val His
1               5                   10

<210> SEQ ID NO 15
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Thr Ser Asn Ile Gly Ser Asn Thr
1               5

<210> SEQ ID NO 16
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ser Gly Ser Ser Ser Asn Ile Gly Gly Asn Thr Val His
1               5                   10

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ser Ser Asn Ile Gly Gly Asn Thr
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ser Asp Asn Gln Arg Pro Ser
1               5

<210> SEQ ID NO 19
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ser Asp Asn
1

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ser Asp Asp Gln Arg Pro Ser
```

<210> SEQ ID NO 21
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ser Asp Asp
1

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ala Ala Trp Asp Asp Ser Leu Asn Gly Val
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ala Ala Trp Asp Glu Ser Leu Asn Gly Val
1               5                   10

<210> SEQ ID NO 24
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gln Ile Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Leu Val Arg Phe Leu Glu Trp Ser His Tyr Tyr Gly
            100                 105                 110

Met Asp Val Trp Gly Gln Gly Thr Thr Val Thr Val Ser Ser
        115                 120                 125

<210> SEQ ID NO 25
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Leu Val Arg Phe Leu Glu Trp Ser His Tyr Tyr Gly
            100                 105                 110

Met Asp Val Trp Gly Gln Gly Thr Thr Val Thr Val Ser Ser
        115                 120                 125

<210> SEQ ID NO 26
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gln Ile Gln Leu Val Gln Ser Gly Gly Gly Val Val Gln Pro Gly Arg
1               5                   10                  15

Ser Leu Arg Leu Ser Cys Ala Ala Ser Gly Phe Ala Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Ile Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Leu Val Arg Phe Leu Glu Trp Ser His Lys Tyr Gly
            100                 105                 110

Met Asp Val Trp Gly Gln Gly Thr Thr Val Thr Val Ser Ser
        115                 120                 125

<210> SEQ ID NO 27
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ala Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Ile Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Leu Val Arg Phe Leu Glu Trp Ser His Lys Tyr Gly
            100                 105                 110

Met Asp Val Trp Gly Gln Gly Thr Thr Val Thr Val Ser Ser
        115                 120                 125

<210> SEQ ID NO 28
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gln Ile Gln Leu Val Gln Ser Gly Gly Gly Val Val Gln Pro Gly Arg
1               5                   10                  15

Ser Leu Arg Leu Ser Cys Ala Ala Ser Gly Phe Ala Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Leu Val Arg Phe Leu Glu Trp Ser His Lys Tyr Gly
            100                 105                 110

Met Asp Val Trp Gly Gln Gly Thr Thr Val Thr Val Ser Ser
        115                 120                 125

<210> SEQ ID NO 29
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ala Phe Ser Ser Tyr
            20                  25                  30

Gly Met His Trp Val Arg Gln Ala Pro Gly Lys Gly Leu Glu Trp Val

```
                    35                  40                  45
Ala Val Ile Ser Tyr Asp Gly Asn Asn Lys Tyr Tyr Ala Asp Ser Val
         50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Asp Leu Leu Val Arg Phe Leu Glu Trp Ser His Lys Tyr Gly
            100                 105                 110
Met Asp Val Trp Gly Gln Gly Thr Thr Val Thr Val Ser Ser
            115                 120                 125
```

<210> SEQ ID NO 30
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

```
Gln Pro Val Leu Thr Gln Pro Pro Ser Ala Ser Gly Thr Pro Gly Gln
 1               5                  10                  15
Arg Val Thr Ile Ser Cys Ser Gly Ser Ser Asn Ile Gly Ser Asn
             20                  25                  30
Thr Val His Trp Tyr Gln Gln Leu Pro Gly Thr Ala Pro Lys Leu Leu
         35                  40                  45
Ile Tyr Ser Asp Asn Gln Arg Pro Ser Gly Val Pro Asp Arg Phe Ser
     50                  55                  60
Gly Ser Lys Ser Gly Thr Ser Ala Ser Leu Val Ile Ser Gly Leu Gln
 65                  70                  75                  80
Ser Asp Asp Glu Ala Asp Tyr Tyr Cys Ala Ala Trp Asp Asp Ser Leu
                 85                  90                  95
Asn Gly Val Phe Gly Gly Gly Thr Lys Leu Thr Val Leu
            100                 105
```

<210> SEQ ID NO 31
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

```
Gln Ser Val Leu Thr Gln Pro Pro Ser Ala Ser Gly Thr Pro Gly Gln
 1               5                  10                  15
Arg Val Thr Ile Ser Cys Ser Gly Ser Ser Asn Ile Gly Ser Asn
             20                  25                  30
Thr Val His Trp Tyr Gln Gln Leu Pro Gly Thr Ala Pro Lys Leu Leu
         35                  40                  45
Ile Tyr Ser Asp Asn Gln Arg Pro Ser Gly Val Pro Asp Arg Phe Ser
     50                  55                  60
Gly Ser Lys Ser Gly Thr Ser Ala Ser Leu Ala Ile Ser Gly Leu Gln
 65                  70                  75                  80
Ser Glu Asp Glu Ala Asp Tyr Tyr Cys Ala Ala Trp Asp Asp Ser Leu
                 85                  90                  95
Asn Gly Val Phe Gly Gly Gly Thr Lys Leu Thr Val Leu
```

<210> SEQ ID NO 32
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gln Pro Val Leu Thr Gln Pro Pro Ser Ala Ser Gly Thr Pro Gly Gln
1               5                   10                  15

Arg Val Thr Ile Ser Cys Ser Gly Ser Thr Ser Asn Ile Gly Ser Asn
            20                  25                  30

Thr Val His Trp Tyr Gln Gln Leu Pro Gly Thr Ala Pro Lys Leu Leu
        35                  40                  45

Ile Tyr Ser Asp Asp Gln Arg Pro Ser Gly Val Pro Asp Arg Phe Ser
    50                  55                  60

Gly Ser Lys Ser Gly Thr Ser Ala Ser Leu Val Ile Ser Gly Leu Gln
65                  70                  75                  80

Ser Asp Asp Glu Ala Asp Tyr Tyr Cys Ala Ala Trp Asp Glu Ser Leu
                85                  90                  95

Asn Gly Val Phe Gly Gly Gly Thr Lys Leu Thr Val Leu
            100                 105

<210> SEQ ID NO 33
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Ser Val Leu Thr Gln Pro Pro Ser Ala Ser Gly Thr Pro Gly Gln
1               5                   10                  15

Arg Val Thr Ile Ser Cys Ser Gly Ser Thr Ser Asn Ile Gly Ser Asn
            20                  25                  30

Thr Val His Trp Tyr Gln Gln Leu Pro Gly Thr Ala Pro Lys Leu Leu
        35                  40                  45

Ile Tyr Ser Asp Asp Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Glu Ser Leu
                85                  90                  95

Asn Gly Val Phe Gly Gly Gly Thr Lys Leu Thr Val Leu
            100                 105

<210> SEQ ID NO 34
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gln Pro Val Leu Thr Gln Pro Pro Ser Ala Ser Gly Thr Pro Gly Gln
1               5                   10                  15

```
Arg Val Thr Ile Ser Cys Ser Gly Ser Ser Asn Ile Gly Gly Asn
            20                  25                  30

Thr Val His Trp Tyr Gln Gln Leu Pro Gly Thr Ala Pro Lys Leu Leu
        35                  40                  45

Ile Tyr Ser Asp Asp Gln Arg Pro Ser Gly Val Pro Asp Arg Phe Ser
50                  55                  60

Gly Ser Lys Ser Gly Thr Ser Ala Ser Leu Val Ile Ser Gly Leu Gln
65                  70                  75                  80

Ser Asp Asp Glu Ala Asp Tyr Tyr Cys Ala Ala Trp Asp Glu Ser Leu
                85                  90                  95

Asn Gly Val Phe Gly Gly Gly Thr Lys Leu Thr Val Leu
            100                 105

<210> SEQ ID NO 35
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Gly Asn
            20                  25                  30

Thr Val His Trp Tyr Gln Gln Leu Pro Gly Thr Ala Pro Lys Leu Leu
        35                  40                  45

Ile Tyr Ser Asp Asp Gln Arg Pro Ser Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Glu Ser Leu
                85                  90                  95

Asn Gly Val Phe Gly Gly Gly Thr Lys Leu Thr Val Leu
            100                 105

<210> SEQ ID NO 36
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Arg

<210> SEQ ID NO 37
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly
```

<210> SEQ ID NO 38
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38

```
cagatccagc tggtgcagtc tgggggaggc gtggtccagc ctggaggtc cctgagactc        60
tcctgtgcag cgtctggatt caccttcagt agctatggca tgcactgggt ccgccaggct      120
ccaggcaagg ggctggagtg ggtggcagtt atatcatatg atggaagtaa taaatactat      180
gcagactccg tgaagggccg attcaccatc tccagagaca attccaagaa cacgctgtat      240
ctgcaaatga acagcctgag agccgaggac acggctgtgt attactgtgc gagagatctc      300
ctggtgcgat ttttggagtg gtcgcactac tacggtatgg acgtctgggg ccaagggacc      360
acggtcaccg tctcctca                                                    378
```

<210> SEQ ID NO 39
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39

```
caggtgcagc tggtggagtc tgggggaggc gtggtccagc ctggaggtc cctgagactc        60
tcctgtgcag cgtctggatt caccttcagt agctatggca tgcactgggt ccgccaggct      120
ccaggcaagg ggctggagtg ggtggcagtt atatcatatg atggaagtaa taaatactat      180
gcagactccg tgaagggccg attcaccatc tccagagaca attccaagaa cacgctgtat      240
ctgcaaatga acagcctgag agccgaggac acggctgtgt attactgtgc gagagatctc      300
```

```
ctggtgcgat ttttggagtg gtcgcactac tacggtatgg acgtctgggg ccaagggacc    360
acggtcaccg tctcctca                                                  378
```

<210> SEQ ID NO 40
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40

```
cagatccagc tggtgcagtc tggggaggc gtggtccagc ctgggaggtc cctgagactc     60
tcctgtgcag cgtctggatt cgccttcagt agctatggca tgcactgggt ccgccaggct   120
ccaggcaagg ggctggagtg ggtggcagtt atatcatatg atggaagtat caaatactat   180
gcagactccg tgaagggccg attcaccatc tccagagaca attccaagaa cacgctgtat   240
ctgcaaatga acagcctgag agccgaggac acggctgtgt attactgtgc gagagatctc   300
ctggtgcgat ttttggagtg gtcgcacaag tacggtatgg acgtctgggg ccaagggacc   360
acggtcaccg tctcctca                                                  378
```

<210> SEQ ID NO 41
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41

```
caggtgcagc tggtggagtc tggggaggc gtggtccagc ctgggaggtc cctgagactc     60
tcctgtgcag cgtctggatt cgccttcagt agctatggca tgcactgggt ccgccaggct   120
ccaggcaagg ggctggagtg ggtggcagtt atatcatatg atggaagtat caaatactat   180
gcagactccg tgaagggccg attcaccatc tccagagaca attccaagaa cacgctgtat   240
ctgcaaatga acagcctgag agccgaggac acggctgtgt attactgtgc gagagatctc   300
ctggtgcgat ttttggagtg gtcgcacaag tacggtatgg acgtctgggg ccaagggacc   360
acggtcaccg tctcctca                                                  378
```

<210> SEQ ID NO 42
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42

```
cagatccagc tggtgcagtc tggggaggc gtggtccagc ctgggaggtc cctgagactc     60
tcctgtgcag cgtctggatt cgccttcagt agctatggca tgcactgggt ccgccaggct   120
ccaggcaagg ggctggagtg ggtggcagtt atatcatatg atggaaataa taaatactat   180
gcagactccg tgaagggccg attcaccatc tccagagaca attccaagaa cacgctgtat   240
ctgcaaatga acagcctgag agccgaggac acggctgtgt attactgtgc gagagatctc   300
ctggtgcgat ttttggagtg gtcgcacaag tacggtatgg acgtctgggg ccaagggacc   360
acggtcaccg tctcctca                                                  378
```

<210> SEQ ID NO 43
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
caggtgcagc tggtggagtc tgggggaggc gtggtccagc ctggggaggtc cctgagactc      60 tcctgtgcag cgtctggatt cgccttcagt agctatggca tgcactgggt ccgccaggct     120
ccaggcaagg ggctggagtg ggtggcagtt atatcatatg atggaaataa taaatactat     180
gcagactccg tgaagggccg attcaccatc tccagagaca attccaagaa cacgctgtat     240
ctgcaaatga acagcctgag agccgaggac acggctgtgt attactgtgc gagagatctc     300
ctggtgcgat ttttggagtg gtcgcacaag tacggtatgg acgtctgggg ccaagggacc     360
acggtcaccg tctcctca                                                   378

<210> SEQ ID NO 44
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
cagcctgtgc tgactcagcc accctcagcg tctgggaccc ccgggcagag ggtcaccatc      60
tcttgttctg gaagcagctc caacatcgga agtaatactg tccactggta ccagcaactc     120
ccaggaacgg ccccccaaact cctcatctat agtgataatc agcgcccctc aggggtccct     180
gaccgattct ctggctccaa gtctggcacc tcagcctccc tggtcatcag tgggctccag     240
tctgacgatg aggctgatta ttactgtgca gcatgggatg acagcctgaa tggggtgttc     300
ggcggaggga ccaagctgac cgtccta                                          327

<210> SEQ ID NO 45
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45
cagtctgtgc tgactcagcc accctcagcg tctgggaccc ccgggcagag ggtcaccatc      60
tcttgttctg gaagcagctc caacatcgga agtaatactg tccactggta ccagcaactc     120
ccaggaacgg ccccccaaact cctcatctat agtgataatc agcgcccctc aggggtccct     180
gaccgattct ctggctccaa gtctggcacc tcagcctccc tggccatcag tgggctccag     240
tctgaggatg aggctgatta ttactgtgca gcatgggatg acagcctgaa tggggtgttc     300
ggcggaggga ccaagctgac cgtccta                                          327

<210> SEQ ID NO 46
<211> LENGTH: 327
<212> TYPE: DNA
<213> ORGANISM: Artificial Sequence
<220> FEATURE:
<223> OTHER INFORMATION: Description of Artificial Sequence: Synthetic -continued polynucleotide

<400> SEQUENCE: 46
cagcctgtgc tgactcagcc accctcagcg tctgggaccc ccgggcagag ggtcaccatc    60
tcttgttctg gaagcacctc caacatcgga agtaatactg tccactggta ccagcaactc   120
ccaggaacgg cccccaaact cctcatctat agtgatgatc agcgcccctc agggggtccct   180 gaccgattct ctggctccaa gtctggcacc tcagcctccc tggtcatcag tgggctccag   240
tctgacgatg aggctgatta ttactgtgca gcatgggatg agagcctgaa tggggtgttc   300
ggcggaggga ccaagctgac cgtccta                                       327

<210> SEQ ID NO 47
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
cagtctgtgc tgactcagcc accctcagcg tctgggaccc ccgggcagag ggtcaccatc    60
tcttgttctg gaagcacctc caacatcgga agtaatactg tccactggta ccagcaactc   120
ccaggaacgg cccccaaact cctcatctat agtgatgatc agcgcccctc agggggtccct   180 gaccgattct ctggctccaa gtctggcacc tcagcctccc tggccatcag tgggctccag   240
tctgaggatg aggctgatta ttactgtgca gcatgggatg agagcctgaa tggggtgttc   300
ggcggaggga ccaagctgac cgtccta                                       327

<210> SEQ ID NO 48
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48
cagcctgtgc tgactcagcc accctcagcg tctgggaccc ccgggcagag ggtcaccatc    60
tcttgttctg gaagcagctc caacatcgga ggaaatactg tccactggta ccagcaactc   120
ccaggaacgg cccccaaact cctcatctat agtgatgatc agcgcccctc agggggtccct   180 gaccgattct ctggctccaa gtctggcacc tcagcctccc tggtcatcag tgggctccag   240
tctgacgatg aggctgatta ttactgtgca gcatgggatg agagcctgaa tggggtgttc   300
ggcggaggga ccaagctgac cgtccta                                       327

<210> SEQ ID NO 49
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
cagtctgtgc tgactcagcc accctcagcg tctgggaccc ccgggcagag ggtcaccatc    60
tcttgttctg gaagcagctc caacatcgga ggaaatactg tccactggta ccagcaactc   120
ccaggaacgg cccccaaact cctcatctat agtgatgatc agcgcccctc agggggtccct   180

```
gaccgattct ctggctccaa gtctggcacc tcagcctccc tggccatcag tgggctccag    240
tctgaggatg aggctgatta ttactgtgca gcatgggatg agagcctgaa tggggtgttc    300
ggcggaggga ccaagctgac cgtccta                                        327
```

<210> SEQ ID NO 50
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Leu Val Arg Phe Leu Glu Trp Ser His Tyr Tyr Gly
            100                 105                 110

Met Asp Val Trp Gly Gln Gly Thr Thr Val Thr Val Ser Ser Ala Ser
        115                 120                 125

Thr Lys Gly Pro Ser Val Phe Pro Leu Ala Pro Cys Ser Arg Ser Thr
    130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Lys Thr Tyr Thr
        195                 200                 205

Cys Asn Val Asp His Lys Pro Ser Asn Thr Lys Val Asp Lys Arg Val
    210                 215                 220

Glu Ser Lys Tyr Gly Pro Pro Cys Pro Pro Cys Pro Ala Pro Glu Phe
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser Gln Glu Asp Pro Glu Val Gln Phe Asn Trp Tyr Val Asp Gly Val
        275                 280                 285

Glu Val His Asn Ala Lys Thr Lys Pro Arg Glu Glu Gln Phe Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
                325                 330                 335
```

```
Ser Ile Glu Lys Thr Ile Ser Lys Ala Lys Gly Gln Pro Arg Glu Pro
            340                 345                 350

Gln Val Tyr Thr Leu Pro Pro Ser Gln Glu Glu Met Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Arg Leu
            405                 410                 415

Thr Val Asp Lys Ser Arg Trp Gln Glu Gly Asn Val Phe Ser Cys Ser
            420                 425                 430

Val Met His Glu Ala Leu His Asn His Tyr Thr Gln Lys Ser Leu Ser
            435                 440                 445

Leu Ser Leu Gly
    450

<210> SEQ ID NO 51
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val His Trp Tyr Gln Gln Leu Pro Gly Thr Ala Pro Lys Leu Leu
        35                  40                  45

Ile Tyr Ser Asp Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215
```

<210> SEQ ID NO 52
<211> LENGTH: 352
<212> TYPE: PRT
<213> ORGANISM: Homo sapiens

<400> SEQUENCE: 52

```
Asn Glu Asn Ser Glu Gln Lys Glu Asn Val Glu Lys Glu Gly Leu Cys
1               5                   10                  15

Asn Ala Cys Thr Trp Arg Gln Asn Thr Lys Ser Ser Arg Ile Glu Ala
            20                  25                  30

Ile Lys Ile Gln Ile Leu Ser Lys Leu Arg Leu Glu Thr Ala Pro Asn
        35                  40                  45

Ile Ser Lys Asp Val Ile Arg Gln Leu Leu Pro Lys Ala Pro Pro Leu
    50                  55                  60

Arg Glu Leu Ile Asp Gln Tyr Asp Val Gln Arg Asp Asp Ser Ser Asp
65                  70                  75                  80

Gly Ser Leu Glu Asp Asp Asp Tyr His Ala Thr Thr Glu Thr Ile Ile
                85                  90                  95

Thr Met Pro Thr Glu Ser Asp Phe Leu Met Gln Val Asp Gly Lys Pro
            100                 105                 110

Lys Cys Cys Phe Phe Lys Phe Ser Ser Lys Ile Gln Tyr Asn Lys Val
        115                 120                 125

Val Lys Ala Gln Leu Trp Ile Tyr Leu Arg Pro Val Glu Thr Pro Thr
    130                 135                 140

Thr Val Phe Val Gln Ile Leu Arg Leu Ile Lys Pro Met Lys Asp Gly
145                 150                 155                 160

Thr Arg Tyr Thr Gly Ile Arg Ser Leu Lys Leu Asp Met Asn Pro Gly
                165                 170                 175

Thr Gly Ile Trp Gln Ser Ile Asp Val Lys Thr Val Leu Gln Asn Trp
            180                 185                 190

Leu Lys Gln Pro Glu Ser Asn Leu Gly Ile Glu Ile Lys Ala Leu Asp
        195                 200                 205

Glu Asn Gly His Asp Leu Ala Val Thr Phe Pro Gly Pro Gly Glu Asp
    210                 215                 220

Gly Leu Asn Pro Phe Leu Glu Val Lys Val Thr Asp Thr Pro Lys Arg
225                 230                 235                 240

Ser Arg Arg Asp Phe Gly Leu Asp Cys Asp Glu His Ser Thr Glu Ser
                245                 250                 255

Arg Cys Cys Arg Tyr Pro Leu Thr Val Asp Phe Glu Ala Phe Gly Trp
            260                 265                 270

Asp Trp Ile Ile Ala Pro Lys Arg Tyr Lys Ala Asn Tyr Cys Ser Gly
        275                 280                 285

Glu Cys Glu Phe Val Phe Leu Gln Lys Tyr Pro His Thr His Leu Val
    290                 295                 300

His Gln Ala Asn Pro Arg Gly Ser Ala Gly Pro Cys Cys Thr Pro Thr
305                 310                 315                 320

Lys Met Ser Pro Ile Asn Met Leu Tyr Phe Asn Gly Lys Glu Gln Ile
                325                 330                 335

Ile Tyr Gly Lys Ile Pro Ala Met Val Val Asp Arg Cys Gly Cys Ser
            340                 345                 350
```

<210> SEQ ID NO 53
<211> LENGTH: 352
<212> TYPE: PRT
<213> ORGANISM: Rattus norvegicus

```
<400> SEQUENCE: 53

Asn Glu Asp Ser Glu Arg Glu Ala Asn Val Glu Lys Glu Gly Leu Cys
1               5                   10                  15

Asn Ala Cys Ala Trp Arg Gln Asn Thr Arg Tyr Ser Arg Ile Glu Ala
            20                  25                  30

Ile Lys Ile Gln Ile Leu Ser Lys Leu Arg Leu Glu Thr Ala Pro Asn
        35                  40                  45

Ile Ser Lys Asp Ala Ile Arg Gln Leu Leu Pro Arg Ala Pro Pro Leu
    50                  55                  60

Arg Glu Leu Ile Asp Gln Tyr Asp Val Gln Arg Asp Asp Ser Ser Asp
65                  70                  75                  80

Gly Ser Leu Glu Asp Asp Tyr His Ala Thr Thr Glu Thr Ile Ile
                85                  90                  95

Thr Met Pro Thr Glu Ser Asp Phe Leu Met Gln Ala Asp Gly Lys Pro
            100                 105                 110

Lys Cys Cys Phe Phe Lys Phe Ser Ser Lys Ile Gln Tyr Asn Lys Val
                115                 120                 125

Val Lys Ala Gln Leu Trp Ile Tyr Leu Arg Ala Val Lys Thr Pro Thr
    130                 135                 140

Thr Val Phe Val Gln Ile Leu Arg Leu Ile Lys Pro Met Lys Asp Gly
145                 150                 155                 160

Thr Arg Tyr Thr Gly Ile Arg Ser Leu Lys Leu Asp Met Ser Pro Gly
                165                 170                 175

Thr Gly Ile Trp Gln Ser Ile Asp Val Lys Thr Val Leu Gln Asn Trp
            180                 185                 190

Leu Lys Gln Pro Glu Ser Asn Leu Gly Ile Glu Ile Lys Ala Leu Asp
        195                 200                 205

Glu Asn Gly His Asp Leu Ala Val Thr Phe Pro Gly Pro Gly Glu Asp
    210                 215                 220

Gly Leu Asn Pro Phe Leu Glu Val Lys Val Thr Asp Thr Pro Lys Arg
225                 230                 235                 240

Ser Arg Arg Asp Phe Gly Leu Asp Cys Asp Glu His Ser Thr Glu Ser
                245                 250                 255

Arg Cys Cys Arg Tyr Pro Leu Thr Val Asp Phe Glu Ala Phe Gly Trp
            260                 265                 270

Asp Trp Ile Ile Ala Pro Lys Arg Tyr Lys Ala Asn Tyr Cys Ser Gly
        275                 280                 285

Glu Cys Glu Phe Val Phe Leu Gln Lys Tyr Pro His Thr His Leu Val
    290                 295                 300

His Gln Ala Asn Pro Arg Gly Ser Ala Gly Pro Cys Cys Thr Pro Thr
305                 310                 315                 320

Lys Met Ser Pro Ile Asn Met Leu Tyr Phe Asn Gly Lys Glu Gln Ile
                325                 330                 335

Ile Tyr Gly Lys Ile Pro Ala Met Val Val Asp Arg Cys Gly Cys Ser
            340                 345                 350

<210> SEQ ID NO 54
<211> LENGTH: 352
<212> TYPE: PRT
<213> ORGANISM: Mus musculus

<400> SEQUENCE: 54

Asn Glu Gly Ser Glu Arg Glu Glu Asn Val Glu Lys Glu Gly Leu Cys
1               5                   10                  15
```

Asn Ala Cys Ala Trp Arg Gln Asn Thr Arg Tyr Ser Arg Ile Glu Ala
                20                  25                  30

Ile Lys Ile Gln Ile Leu Ser Lys Leu Arg Leu Glu Thr Ala Pro Asn
                35                  40                  45

Ile Ser Lys Asp Ala Ile Arg Gln Leu Leu Pro Arg Ala Pro Pro Leu
            50                  55                  60

Arg Glu Leu Ile Asp Gln Tyr Asp Val Gln Arg Asp Asp Ser Ser Asp
65                  70                  75                  80

Gly Ser Leu Glu Asp Asp Asp Tyr His Ala Thr Thr Glu Thr Ile Ile
                85                  90                  95

Thr Met Pro Thr Glu Ser Asp Phe Leu Met Gln Ala Asp Gly Lys Pro
                100                 105                 110

Lys Cys Cys Phe Phe Lys Phe Ser Ser Lys Ile Gln Tyr Asn Lys Val
            115                 120                 125

Val Lys Ala Gln Leu Trp Ile Tyr Leu Arg Pro Val Lys Thr Pro Thr
            130                 135                 140

Thr Val Phe Val Gln Ile Leu Arg Leu Ile Lys Pro Met Lys Asp Gly
145                 150                 155                 160

Thr Arg Tyr Thr Gly Ile Arg Ser Leu Lys Leu Asp Met Ser Pro Gly
                165                 170                 175

Thr Gly Ile Trp Gln Ser Ile Asp Val Lys Thr Val Leu Gln Asn Trp
            180                 185                 190

Leu Lys Gln Pro Glu Ser Asn Leu Gly Ile Glu Ile Lys Ala Leu Asp
            195                 200                 205

Glu Asn Gly His Asp Leu Ala Val Thr Phe Pro Gly Pro Gly Glu Asp
210                 215                 220

Gly Leu Asn Pro Phe Leu Glu Val Lys Val Thr Asp Thr Pro Lys Arg
225                 230                 235                 240

Ser Arg Arg Asp Phe Gly Leu Asp Cys Asp Glu His Ser Thr Glu Ser
                245                 250                 255

Arg Cys Cys Arg Tyr Pro Leu Thr Val Asp Phe Glu Ala Phe Gly Trp
            260                 265                 270

Asp Trp Ile Ile Ala Pro Lys Arg Tyr Lys Ala Asn Tyr Cys Ser Gly
        275                 280                 285

Glu Cys Glu Phe Val Phe Leu Gln Lys Tyr Pro His Thr His Leu Val
        290                 295                 300

His Gln Ala Asn Pro Arg Gly Ser Ala Gly Pro Cys Cys Thr Pro Thr
305                 310                 315                 320

Lys Met Ser Pro Ile Asn Met Leu Tyr Phe Asn Gly Lys Glu Gln Ile
                325                 330                 335

Ile Tyr Gly Lys Ile Pro Ala Met Val Val Asp Arg Cys Gly Cys Ser
                340                 345                 350

<210> SEQ ID NO 55
<211> LENGTH: 277
<212> TYPE: PRT
<213> ORGANISM: Macaca fascicularis

<400> SEQUENCE: 55

Asn Glu Asn Ser Glu Gln Lys Glu Asn Val Lys Glu Gly Leu Cys
1               5                   10                  15

Asn Ala Cys Thr Trp Arg Gln Asn Thr Lys Ser Ser Arg Ile Glu Ala
                20                  25                  30

Ile Lys Ile Gln Ile Leu Ser Lys Leu Arg Leu Glu Thr Ala Pro Asn
                35                  40                  45

```
Ile Ser Lys Asp Ala Ile Arg Gln Leu Leu Pro Lys Ala Pro Pro Leu
    50                  55                  60

Arg Glu Leu Ile Asp Gln Tyr Asp Val Gln Arg Asp Asp Ser Ser Asp
 65                  70                  75                  80

Gly Ser Leu Glu Asp Asp Tyr His Ala Thr Thr Glu Thr Ile Ile
                 85                  90                  95

Thr Met Pro Thr Glu Ser Asp Phe Leu Met Gln Val Asp Gly Lys Pro
                100                 105                 110

Lys Cys Cys Phe Phe Lys Phe Ser Ser Lys Ile Gln Tyr Asn Lys Val
                115                 120                 125

Val Lys Ala Gln Leu Trp Ile Tyr Leu Arg Pro Val Glu Thr Pro Thr
    130                 135                 140

Thr Val Phe Val Gln Ile Leu Arg Leu Ile Lys Pro Met Lys Asp Gly
145                 150                 155                 160

Thr Arg Tyr Thr Gly Ile Arg Ser Leu Lys Leu Asp Met Asn Pro Gly
                165                 170                 175

Thr Gly Ile Trp Gln Ser Ile Asp Val Lys Thr Val Leu Gln Asn Trp
                180                 185                 190

Leu Lys Gln Pro Glu Ser Asn Leu Gly Ile Glu Ile Lys Ala Leu Asp
            195                 200                 205

Glu Asn Gly His Asp Leu Ala Val Thr Phe Pro Gly Pro Gly Glu Asp
    210                 215                 220

Gly Leu Asn Pro Phe Leu Glu Val Lys Val Thr Asp Thr Pro Lys Arg
225                 230                 235                 240

Ser Arg Arg Asp Phe Gly Leu Asp Cys Asp Glu His Ser Thr Glu Ser
                245                 250                 255

Arg Cys Cys Arg Tyr Pro Leu Thr Val Asp Phe Glu Ala Phe Gly Trp
                260                 265                 270

Asp Trp Ile Ile Ala
            275

<210> SEQ ID NO 56
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Arg Ser Arg Arg
1

<210> SEQ ID NO 57
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Arg Val Arg Arg
1

<210> SEQ ID NO 58
<211> LENGTH: 5
<212> TYPE: PRT
<213> ORGANISM: Artificial Sequence
```

<220> FEATURE:
<223> OTHER INFORMATION: Description of Artificial Sequence: Synthetic
      peptide

<400> SEQUENCE: 58

Cys Pro Pro Cys Pro
1               5

<210> SEQ ID NO 59
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

His Tyr Tyr Gly Met Asp Val Trp Gly Gln Gly Thr Thr Val Thr Val
1               5                   10                  15

Ser

<210> SEQ ID NO 60
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
                20                  25                  30

Thr Val Asn Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys
                85

<210> SEQ ID NO 61
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Val Phe Gly Gly Gly Thr Lys Leu Thr Val Leu
1               5                   10

<210> SEQ ID NO 62
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

```
Pro Lys Ala Pro Pro Leu Arg Glu Leu Ile Asp Gln Tyr Asp Val Gln
1               5                   10                  15

Arg Asp Asp Ser Ser Asp Gly Ser Leu Glu Asp Asp Tyr His Ala
            20                  25                  30

Thr

<210> SEQ ID NO 63
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Gly Leu Asn Pro Phe Leu Glu Val Lys Val Thr Asp Thr Pro Lys Arg
1               5                   10                  15

Ser Arg Arg Asp Phe Gly Leu Asp Cys Asp Glu His Ser Thr Glu Ser
            20                  25                  30

Arg Cys

<210> SEQ ID NO 64
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Gln Val Gln Leu Gln Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Thr Trp Val Arg Gln Ala Pro Gly Lys Gly Leu Glu Trp Val
        35                  40                  45

Ser Ala Ile Ser Gly Gly Gly Ala Thr Tyr Tyr Ala Asp Ser Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Ser Pro Ala Gly His Ile Cys Ser Gly Gly Ser Cys Gln Tyr Tyr
            100                 105                 110

Tyr Tyr Gly Met Asp Val Trp Gly Gln Gly Thr Thr Val Thr Val Ser
        115                 120                 125

Ser Gly Ser
    130

<210> SEQ ID NO 65
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Gln Val Gln Leu Val Gln Ser Gly Ala Glu Val Lys Lys Pro Gly Ser
1               5                   10                  15
```

```
Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Arg His Leu Tyr Arg Arg Gly Tyr Ser Ser Val Asp Gly
            100                 105                 110

Met Asp Val Trp Gly Gln Gly Thr Thr Val Thr Val Ser Ser Gly Ser
            115                 120                 125

<210> SEQ ID NO 66
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Pro Ile Gly Ser Gly Tyr Asp Tyr Trp Gly Gln Gly Thr
            100                 105                 110

Leu Val Thr Val Ser Ser Gly Ser
            115                 120

<210> SEQ ID NO 67
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Gln Val Gln Leu Val Gln Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
            35                  40                  45

Ser Gly Ile Ser Trp Asn Ser Gly Ser Ile Gly Tyr Ala Asp Ser Val
        50                  55                  60
```

```
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Lys Glu Ile Ser Asp Thr Ala Met Gly Phe Asp Tyr Trp Gly Gln
            100                 105                 110

Gly Thr Leu Val Thr Val Ser Ser Gly Ser
        115                 120

<210> SEQ ID NO 68
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Gln Val Gln Leu Val Gln Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
             20                  25                  30

Trp Met Tyr Trp Val Arg Gln Ala Pro Gly Lys Gly Leu Val Trp Val
         35                  40                  45

Ser Asn Ile Asn Ser Asp Gly Ser Ser Thr Ser Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Asp Glu Asp Thr Ala Val Tyr Tyr Cys
                 85                  90                  95

Ala Arg Glu Gly Tyr Asn Ala His Tyr Phe Asp Tyr Trp Gly Gln Gly
            100                 105                 110

Thr Leu Val Thr Val Ser Ser Gly Ser
        115                 120

<210> SEQ ID NO 69
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Gln Ile Gln Leu Val Gln Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Val Ile Trp Tyr Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Leu Gly Tyr His Pro Leu Phe Asp Tyr Trp Gly Gln Gly
            100                 105                 110
```

Thr Leu Val Thr Val Ser Ser Gly Ser
        115                 120

<210> SEQ ID NO 70
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gly Phe Thr Phe Ser Ser Tyr Ala
1               5

<210> SEQ ID NO 71
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Phe Thr Phe Asp Asp Tyr Gly
1               5

<210> SEQ ID NO 72
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ile Ser Gly Gly Gly Gly Ala Thr
1               5

<210> SEQ ID NO 73
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ala Ser Pro Ala Gly His Ile Cys Ser Gly Gly Ser Cys Gln Tyr Tyr
1               5                   10                  15

Tyr Tyr Gly Met Asp Val
            20

<210> SEQ ID NO 74
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ala Arg Asp Arg His Leu Tyr Arg Arg Gly Tyr Ser Ser Val Asp Gly
1               5                   10                  15

Met Asp Val

```
<210> SEQ ID NO 75
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Ala Arg His Pro Ile Gly Ser Gly Tyr Asp Tyr
1               5                   10

<210> SEQ ID NO 76
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ala Lys Glu Ile Ser Asp Thr Ala Met Gly Phe Asp Tyr
1               5                   10

<210> SEQ ID NO 77
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gly Phe Thr Phe Ser Asn Tyr Trp
1               5

<210> SEQ ID NO 78
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Ile Asn Ser Asp Gly Ser Ser Thr
1               5

<210> SEQ ID NO 79
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Ala Arg Glu Gly Tyr Asn Ala His Tyr Phe Asp Tyr
1               5                   10

<210> SEQ ID NO 80
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80
```

```
Ala Lys Gly Leu Gly Tyr His Pro Leu Phe Asp Tyr
1               5                   10
```

```
<210> SEQ ID NO 81
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Asp Ile Gln Met Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Arg Val Asp Met Ala Arg Thr Val Ala Ala
            100                 105                 110

Pro Ser Val Phe
        115
```

```
<210> SEQ ID NO 82
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Gly
            20                  25                  30

Tyr Leu Ala Trp Tyr Gln Gln Lys Ala Gly Gln Ala Pro Arg Leu Leu
        35                  40                  45

Ile Tyr Gly Gly Ser Ala Arg Ala Pro Gly Ile Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Arg Ser Ile Trp Pro
                85                  90                  95

Leu Thr Phe Gly Gly Gly Thr Lys Val Glu Ile Lys Arg Thr Val Ala
            100                 105                 110

Ala Pro Ser Val Phe
        115
```

```
<210> SEQ ID NO 83
<211> LENGTH: 121
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 83

Asp Ile Val Met Thr Gln Ser Pro Val Ser Leu Pro Val Thr Leu Gly
1               5                   10                  15

Gln Pro Ala Ser Ile Ser Cys Arg Ser Ser Gln Ser Val Val Tyr Arg
            20                  25                  30

Asp Gly Asn Thr Tyr Leu Ser Trp Phe Leu Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Ala Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Ser Ser Trp Pro Tyr Thr Phe Gly Gln Gly Thr Lys Leu Glu Ile Lys
            100                 105                 110

Arg Thr Val Ala Ala Pro Ser Val Phe
        115                 120

<210> SEQ ID NO 84
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Ile Ser Trp Tyr Gln Gln Tyr Pro Gly Lys Ala Pro Lys Leu
        35                  40                  45

Met Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Asn Ser Tyr Thr Ser Ser
                85                  90                  95

Arg Thr Val Val Phe Gly Gly Gly Thr Lys Leu Thr Val Leu Gly Gln
            100                 105                 110

Pro Lys Ala Ala Pro Ser Val Thr Leu Phe Pro Pro Ser Ser
        115                 120                 125

<210> SEQ ID NO 85
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Gln Ser Ala Leu Thr Gln Pro Ala Ser Val Ser Gly Ser Pro Gly Gln
1               5                   10                  15
```

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Leu Ile Tyr Asp Val Thr Lys Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Val Val Phe Gly Gly Gly Thr Lys Leu Thr Val Leu Gly Gln
            100                 105                 110

Pro Lys Ala Ala Pro Ser Val Thr Leu Phe Pro Pro Ser Ser Lys Ala
        115                 120                 125

Ser Gly Ala
    130

<210> SEQ ID NO 86
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
                20                  25                  30

Ser Asp Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Ser Phe Gly Pro Gly Thr Lys Val Asp Ile Lys
            100                 105                 110

Arg Thr Val Ala Ala Pro Ser Val Phe Lys Ala Ser Gly Ala
        115                 120                 125

<210> SEQ ID NO 87
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Gln Gly Ile Ser Ser Tyr
1               5

<210> SEQ ID NO 88
<211> LENGTH: 7
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 88

Gln Ser Val Ser Ser Gly Tyr
1               5

<210> SEQ ID NO 89
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gln Ser Val Val Tyr Arg Asp Gly Asn Thr Tyr
1               5                   10

<210> SEQ ID NO 90
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Ala Ala Ser
1

<210> SEQ ID NO 91
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Gly Gly Ser
1

<210> SEQ ID NO 92
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Ser Asp Asn
1

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gln Gln Ser Tyr Ser Thr Pro Leu Thr
1               5

```
<210> SEQ ID NO 94
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gln Gln Arg Ser Ile Trp Pro Leu Thr
1               5

<210> SEQ ID NO 95
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Met Gln Gly Ser Ser Trp Pro Tyr Thr
1               5

<210> SEQ ID NO 96
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Ala Ala Trp Asp Asp Ser Leu Asn Gly Val
1               5                   10

<210> SEQ ID NO 97
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Asn Ser Tyr Thr Ser Ser Arg Thr Val Val
1               5                   10

<210> SEQ ID NO 98
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gln Ser Val Leu Tyr Ser Ser Asp Asn Lys Asn Tyr
1               5                   10

<210> SEQ ID NO 99
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99
```

```
Asp Val Thr
1

<210> SEQ ID NO 100
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ser Ser Tyr Thr Ser Ser Ser Thr Val Val
1               5                   10

<210> SEQ ID NO 101
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gln Gln Tyr Tyr Ser Thr Pro Ser
1               5
```

COMPOSITIONS FOR MAKING AND USING ANTI-MYOSTATIN ANTIBODIES

CROSS REFERENCE TO RELATED APPLICATIONS

This application is a divisional of U.S. patent application Ser. No. 16/374,854, filed Apr. 4, 2019, which is a continuation of U.S. patent application Ser. No. 15/524,651, filed May 5, 2017 which, in turn, is a 35 U.S.C. § 371 national stage filing of International Application No. PCT/US2015/059468, filed on Nov. 6, 2015, which in turn claims priority under 35 U.S.C. § 119(e) of U.S. Provisional Patent Application No. 62/076,230, filed on Nov. 6, 2014 and entitled "TRANSFORMING GROWTH FACTOR-RELATED ANTIBODIES AND USES THEREOF"; U.S. Provisional Patent Application No. 62/100,361, filed on Jan. 6, 2015 and entitled "TRANSFORMING GROWTH FACTOR-RELATED ANTIBODIES AND USES THEREOF"; U.S. Provisional Patent Application No. 62/187,348, filed on Jul. 1, 2015 and entitled "TRANSFORMING GROWTH FACTOR-RELATED ANTIBODIES AND USES THEREOF" and U.S. Provisional Patent Application No. 62/219,094, filed Sep. 15, 2015, and entitled "ANTI-PRO/LATENT-MYOSTATIN ANTIBODIES AND USES THEREOF". Each of these applications is incorporated herein by reference in its entirety for all purposes.

SEQUENCE LISTING

The instant application contains a Sequence Listing which has been submitted electronically in ASCII format and is hereby incorporated by reference in its entirety. Said ASCII copy, created on Apr. 2, 2019, is named 127036-00906_SL.txt and is 70,643 bytes in size.

FIELD OF THE DISCLOSURE

Embodiments of the present disclosure may include modulators of growth factor activity. In some embodiments, such modulators may include antibodies and may modulate TGF-β family member activity and/or biology.

BACKGROUND OF THE DISCLOSURE

Myostatin is a secreted growth factor which negatively regulates muscle mass. Loss of function mutations in the Myostatin gene, leading to a hypermuscular phenotype, have been described in cattle, sheep, fish, dogs and humans Myostatin expression is generally limited to skeletal muscle, with low levels of expression reported in adipose and cardiac tissues. Inhibition of Myostatin signaling leads to an increase in muscle size.

SUMMARY OF THE DISCLOSURE

Aspects of the disclosure relate, in some embodiments, to antibodies that bind specifically to forms of Myostatin (e.g., proMyostatin and/or latent Myostatin). For example, antibodies provided herein specifically bind to one or more of a pro-form, and/or a latent-form of Myostatin, such as pro-Myostatin and/or latent Myostatin. In some embodiments, such antibodies inhibit Myostatin signaling. In some embodiments, inhibition of Myostatin signaling is useful for increasing muscle mass or preventing muscle atrophy. In some embodiments, antibodies provided herein bind to and prevent cleavage of Myostatin by a proprotein convertase and/or a tolloid protease. Preventing cleavage of proMyostatin or latent Myostatin, in some embodiments, prevents Myostatin activation. Further aspects of the disclosure relate to antibodies having an affinity to an antigen that is sensitive to pH. In some embodiments, such pH sensitive antibodies are effective for clearing antigens from serum. Furthermore, in some embodiments, antibodies provided herein are sweeping antibodies that can efficiently clear antigens (e.g., proMyostatin and/or latent Myostatin) from serum.

Aspects of the present disclosure include an antibody that comprises a heavy chain variable domain and a light chain variable domain, in which the heavy chain variable domain comprises a complementarity determining region 3 (CDRH3) comprising a sequence as set forth in any one of SEQ ID NOs: 10-11. In some embodiments, an antibody specifically binds to pro/latent-Myostatin. In some embodiments, the light chain variable domain comprises a complementarity determining region 3 (CDRL3) comprising a sequence as set forth in any one of SEQ ID NO: 22-23. In another embodiment, said antibody comprises six complementarity determining regions (CDRs): CDRH1, CDRH2, CDRH3, CDRL1, CDRL2, and CDRL3, wherein CDRH1 comprises a sequence as set forth in any one of SEQ ID NOs: 1-3, CDRH2 comprises a sequence as set forth in any one of SEQ ID NOs: 4-9, CDRH3 comprises a sequence as set forth in any one of SEQ ID NOs: 10-11, CDRL1 comprises a sequence as set forth in any one of SEQ ID NOs: 12-17, CDRL2 comprises a sequence as set forth in any one of SEQ ID NOs: 18-21, and CDRL3 comprises a sequence as set forth in any one of SEQ ID NOs: 22-23.

In some embodiments, said CDRH1 comprises a sequence as set forth in SEQ ID NO: 1 or 2, CDRH2 comprises a sequence as set forth in SEQ ID NO: 4 or 5, CDRH3 comprises a sequence as set forth in SEQ ID NO: 10, CDRL1 comprises a sequence as set forth in SEQ ID NO: 12 or 13, CDRL2 comprises a sequence as set forth in SEQ ID NO: 18 or 19, and CDRL3 comprises a sequence as set forth in SEQ ID NO: 22.

In another embodiment, said CDRH1 comprises a sequence as set forth in SEQ ID NO: 1 or 3, CDRH2 comprises a sequence as set forth in SEQ ID NO: 6 or 7, CDRH3 comprises a sequence as set forth in SEQ ID NO: 11, CDRL1 comprises a sequence as set forth in SEQ ID NO: 14 or 15, CDRL2 comprises a sequence as set forth in SEQ ID NO: 20 or 21, and CDRL3 comprises a sequence as set forth in SEQ ID NO: 23.

In other embodiments, CDRH1 comprises a sequence as set forth in SEQ ID NO: 1 or 3, CDRH2 comprises a sequence as set forth in SEQ ID NO: 8 or 9, CDRH3 comprises a sequence as set forth in SEQ ID NO: 11, CDRL1 comprises a sequence as set forth in SEQ ID NO: 16 or 17, CDRL2 comprises a sequence as set forth in SEQ ID NO: 20 or 21, and CDRL3 comprises a sequence as set forth in SEQ ID NO: 23.

In another embodiment, said antibody comprises a heavy chain variable domain sequence as set forth in any one of SEQ ID NOs: 25-29. In some embodiments, said antibody comprises a light chain variable domain sequence of as set forth in any one of SEQ ID NOs: 30-35.

Other aspects of the disclosure include an antibody that specifically binds to pro/latent-Myostatin and that comprises a heavy chain variable domain and a light chain variable domain, in which the light chain variable domain comprises a complementarity determining region 3 (CDRL3) comprising a sequence as set forth in any one of SEQ ID NO: 22-23.

In some embodiments, said antibody comprises a light chain variable domain sequence of SEQ ID NO: 30.

Some aspects of the disclosure relate to a polypeptide having a sequence selected from the group consisting of SEQ ID NO: 24, SEQ ID NO: 25, SEQ ID NO: 26, SEQ ID NO: 27, SEQ ID NO: 28, and SEQ ID NO 29. In some embodiments, the polypeptide is a variable heavy chain domain. In some embodiments, the polypeptide is at least 75% (e.g., 80%, 85%, 90%, 95%, 98%, or 99%) identical to any one of the amino acid sequences set forth in SEQ ID NO: 24, SEQ ID NO: 25, SEQ ID NO: 26, SEQ ID NO: 27, SEQ ID NO: 28, or SEQ ID NO 29.

Some aspects of the disclosure relate to a polypeptide having a sequence selected from the group consisting of SEQ ID NO: 30, SEQ ID NO: 31, SEQ ID NO: 32, SEQ ID NO: 33, SEQ ID NO: 34, and SEQ ID NO 35. In some embodiments, the polypeptide is a variable light chain domain. In some embodiments, the polypeptide is at least 75% (e.g., 80%, 85%, 90%, 95%, 98%, or 99%) identical to any one of the amino acid sequences set forth in SEQ ID NO: 30, SEQ ID NO: 31, SEQ ID NO: 32, SEQ ID NO: 33, SEQ ID NO: 34, or SEQ ID NO 35.

Another aspect of the disclosure includes an antibody that competes for binding to pro/latent-Myostatin with an antibody described above. In some embodiments, said antibody binds to pro/latent-Myostatin at the same epitope as an antibody described above. In another embodiment, an antibody competes for binding to pro/latent-Myostatin with an equilibrium dissociation constant, Kd, between the antibody and pro/latent-Myostatin of is less than $10^{-6}$ M. In other embodiments, said antibody's Kd is in a range of $10^{-11}$M to $10^{-6}$M.

In some embodiments, an antibody is a humanized antibody, a diabody, a chimeric antibody, a Fab fragment, a F(ab')2 fragment, or an Fv fragment. In another embodiment, an antibody is a humanized antibody. In another embodiment, an antibody is a human antibody. In some embodiments, an antibody comprises a framework having a human germline sequence. In another embodiment, an antibody comprises a heavy chain constant domain selected from the group consisting of IgG, IgG1, IgG2, IgG2A, IgG2B, IgG2C, IgG3, IgG4, IgA1, IgA2, IgD, IgM, and IgE constant domains. In some embodiments, an antibody comprises a constant domain of IgG4. In other embodiments, an antibody comprises a constant domain of IgG4 having a backbone substitution of Ser to Pro that produces an IgG1-like hinge and permits formation of inter-chain disulfide bonds. In another embodiment, an antibody is conjugated to an agent selected from the group consisting of a fluorescent agent, a luminescent agent, an enzymatic agent and a radioactive agent.

In another embodiment, an antibody specifically binds to pro/latent-Myostatin compared with mature myostatin. In some embodiments, an antibody specifically binds to pro/latent-Myostatin compared with another member of the transforming growth factor Beta family. In another embodiment, said member is GDF11 or Activin.

A further aspect of the disclosure includes an antibody that specifically binds pro/latent-Myostatin and that inhibits proteolytic formation of mature myostatin by a tolloid protease. In some embodiments, said antibody inhibits proteolytic formation of mature myostatin by a tolloid protease with an IC50 of less than 1 µM. In some embodiments, an antibody is cross-reactive with human and murine pro/latent-Myostatin. In other embodiments, the antibody specifically binds to pro/latent-Myostatin compared with GDF11 or Activin. In another embodiment, an antibody specifically binds to pro/latent-Myostatin compared with mature myostatin.

Another aspect of the disclosure encompasses a method of reducing myostatin receptor activation in cells present in a medium comprising pro/latent-Myostatin, the method comprising delivering to the medium an antibody described above in an amount effective for inhibiting proteolytic activation of the pro/latent-Myostatin. In some embodiments, the medium further comprises a proprotein convertase. In other embodiments, the medium further comprises a tolloid protease. In another embodiment, an antibody is delivered to the medium in an amount effective for inhibiting proteolytic activation of the pro/latent-Myostatin by the tolloid protease. In some embodiments, the cell is in vitro. In other embodiments, the cell is in vivo.

Another aspect of the disclosure includes a method of treating a subject having a myopathy, the method comprising administering to the subject an effective amount of an antibody described above. In some embodiments, the myopathy is a primary myopathy. In another embodiment, the primary myopathy comprises disuse atrophy. In other embodiments, the disuse atrophy is associated with hip fracture, elective joint replacement, critical care myopathy, spinal cord injury or stroke. In some embodiments, the myopathy is a secondary myopathy, in which muscle loss is secondary to a disease pathology. In other embodiments, the secondary myopathy comprises denervation, genetic muscle weakness or cachexia. In another embodiment, the secondary myopathy is a denervation associated with amyotrophic lateral sclerosis or spinal muscular atrophy. In some embodiments, the secondary myopathy is a genetic muscle weakness associated with a muscular dystrophy. In other embodiments, the secondary myopathy is a cachexia associated with renal failure, AIDS, a cardiac condition, cancer or aging.

Another aspect of the disclosure includes a method of treating a subject having a disease or condition related to aging. Exemplary diseases and conditions related to ageing include, without limitation, sarcopenia (age-related muscle loss), frailty, and androgen deficiency.

Another aspect of the disclosure includes a method of treating a subject having a disease or condition related to disuse atrophy/trauma. Exemplary diseases and conditions related to disuse atrophy/trauma include, without limitation, muscle weakness related to time spent in an intensive care unit (ICU), hip/joint replacement, hip fracture, stroke, bed rest, SCI, rotator cuff injury, knee replacement, bone fracture, and burns.

Another aspect of the disclosure includes a method of treating a subject having a neurodegenerative disease or condition. Exemplary neurodegenerative diseases or conditions include, without limitation, spinal muscular atrophy and amyotrophic lateral sclerosis (ALS).

Another aspect of the disclosure includes a method of treating a subject having a disease or condition related to Cachexia. Exemplary diseases and conditions related to cachexia include, without limitation, cancer, chronic heart failure, acquired immune deficiency syndrome (AIDS), chronic obstructive pulmonary disease (COPD), and chronic kidney disease (CKD).

Another aspect of the disclosure includes a method of treating a subject having a disease or condition related to rare diseases. Exemplary rare diseases and conditions include, without limitation, osteogenesis imperfecta, sporadic Inclusion body myositis, and acute lymphoblastic leukemia.

Another aspect of the disclosure includes a method of treating a subject having a disease or condition related to a metabolic disorder and/or body composition. In some embodiments, the disease or condition is obesity (e.g., severe obesity), Prader-Willi, type II diabetes, or anorexia. However, additional diseases or conditions related to metabolic disorders and/or body composition are within the scope of this disclosure.

Another aspect of the disclosure includes a method of treating a subject having a disease or condition related to congenital myopathies. Exemplary congenital myopathies include, without limitation, X-linked myotubular myopathy, autosomal dominant centronuclear myopathy, autosomal recessive centronuclear myopathy, nemaline myopathy, and congenital fiber-type disproportion myopathy.

Another aspect of the disclosure includes a method of treating a subject having a disease or condition related to muscular dystrophies. Exemplary muscular dystrophies include, without limitation, Duchenne's, Becker's, facioscapulohumeral (FSH), and Limb-Girdle muscular dystrophies.

Another aspect of the disclosure includes a method of treating a subject having a urogynecological related disease or condition, glottic disorders (stenosis), extraocular myopathy, carpel tunnel, Guillain-Barré, or osteosarcoma.

In some embodiments, treatment results in improved muscle strength in the subject. In other embodiments, treatment results in improved metabolic status in the subject.

In some embodiments, an antibody is administered at a dose in a range of 0.1 mg/kg to 100 mg/kg. In another embodiment, an antibody is administered at a dose in a range of 0.3 mg/kg to 30 mg/kg.

In some embodiments, an antibody is administered to the subject intravenously. In other embodiments, an antibody is administered to the subject subcutaneously. In another embodiment, an antibody is administered to the subject on multiple occasions. In some embodiments, said multiple administrations are performed at least monthly. In another embodiment, said multiple administrations are performed at least weekly.

A further aspect of the disclosure includes a composition comprising any antibody described above and a carrier. In some embodiments, said carrier is a pharmaceutically acceptable carrier. In other embodiments, an antibody and carrier are in a lyophilized form. In another embodiment, an antibody and carrier are in solution. In some embodiments, an antibody and carrier are frozen. In other embodiments, an antibody and carrier are frozen at a temperature less than or equal to −65° C.

Other aspects of the disclosure include an isolated nucleic acid encoding a protein comprising three complementarity determining regions (CDRs): CDRH1, CDRH2, and CDRH3, in which CDRH3 comprises a sequence as set forth in SEQ ID NO: 10 or 11. In some embodiments, said CDRH1 comprises a sequence as set forth in SEQ ID NO: 1, 2 or 3. In other embodiments, CDRH2 comprises a sequence as set forth in any one of SEQ ID NOs: 4-9.

Another aspect of the present disclosure includes an isolated nucleic acid encoding a protein comprising three complementarity determining regions (CDRs): CDRL1, CDRL2, and CDRL3, in which CDRL3 comprises a sequence as set forth in SEQ ID NO: 22. In some embodiments, said CDRL1 comprises a sequence as set forth in any one of SEQ ID NOs: 12-17. In other embodiments, CDRL2 comprises a sequence as set forth in any one of SEQ ID NOs: 18-21.

Further aspects of the present disclosure include an isolated nucleic acid comprising a sequence as set forth in any one of SEQ ID NOs: 38-49.

Another aspect of the disclosure includes an isolated cell comprising an isolated nucleic acid described above.

The present disclosure, in some aspects, includes methods of assessing a biological sample obtained from a subject having a myopathy. In some embodiments, the method comprises: preparing an immunological reaction mixture that comprises protein of a biological sample obtained from the subject and an antibody that specifically binds pro/latent-Myostatin; maintaining the immunological reaction mixture under conditions that permit binding complexes to form between the antibody and a pro/latent-Myostatin; and determining the extent of binding complex formation. In some embodiments, the method comprises: preparing an immunological reaction mixture that comprises protein of a biological sample obtained from the subject and an antibody that specifically binds pro-Myostatin; maintaining the immunological reaction mixture under conditions that permit binding complexes to form between the antibody and a pro-Myostatin; and determining the extent of binding complex formation. In some embodiments, the method comprises: preparing an immunological reaction mixture that comprises protein of a biological sample obtained from the subject and an antibody that specifically binds latent-Myostatin;

maintaining the immunological reaction mixture under conditions that permit binding complexes to form between the antibody and a latent-Myostatin; and determining the extent of binding complex formation. In some embodiments, the method comprises: preparing an immunological reaction mixture that comprises protein of a biological sample obtained from the subject and an antibody that specifically binds mature-Myostatin; maintaining the immunological reaction mixture under conditions that permit binding complexes to form between the antibody and a mature-Myostatin; and determining the extent of binding complex formation.

BRIEF DESCRIPTION OF THE FIGURES

FIG. 1A shows Myostatin secreted as a proprotein, with an inhibitory prodomain followed by a C-terminal growth factor domain, which exists as a disulfide-linked dimer. FIG. 1B shows precursor protein assembled in an inactive conformation where the prodomain (purple) encloses the growth factor (cyan) with a "straight-jacket" assembly. This figure is an adaption from the structure of latent TGFβ1.

3A), samples were then run under reducing conditions and probed by western blot with an antibody raised towards the prodomain of Myostatin (FIG. 3B). An ~18 kDa band (box), corresponding to the N-terminal portion of the prodomain generated after tolloid cleavage, decreased proportionally with increasing doses of Ab1. The latent and proMyostatin standards (45 ng loaded) show the migration of proMyostatin at ~50 kDa, and the prodomain at ~37 kDa. FIG. 3C shows the activation of Myostatin involves two distinct protease events, generating three major Myostatin species. The biosynthetic precursor protein, proMyostatin, is processed by two separate proteases. Cleavage of proMyostatin (and proGDF11) is carried out by a proprotein convertase, such as Furin/PACE3 (Paired Basic Amino acid Cleaving Enzyme 3) or PCSK5 (Proprotein Convertase Subtilisin/Kexin type 5), which cuts at a conserved RXXR site between the prodomain and mature growth factor. This cleavage produces a latent complex, in which the mature growth factor is shielded from binding to its receptors by the prodomain. See FIG. 3B, which illustrates the potential inhibition of a tolloid protease, blocking further cleavage of proMyostatin. Activation and release of the active growth factor is accomplished after cleavage by an additional protease from the BMP/tolloid family, such as TLL-2 (Tolloid-like protein 2) or BMP1 (Bone Morphogenetic Protein 1).

FIG. 7A shows the mean gastrocnemius weight. FIG. 7B shows the mean pectoralis weight. FIG. 7C shows the mean soleus weight. FIG. 7D shows the mean triceps weight. Statistical evaluation was performed using a one-way ANOVA followed by Holm-Sidak's post hoc test in comparison to the Vehicle Control Group (Group 1). Data represent group means±SEM. **$p<0.01$. Bars indicate from left-to-right Groups 1-5.

FIG. 8A shows the mean tibialis anterior weight. FIG. 8B shows the mean diaphragm weight. FIG. 8C shows the mean quadriceps weight. Statistical evaluation was performed using a one-way ANOVA followed by Holm-Sidak's post hoc test in comparison to the Vehicle Control Group (Group 1). Data represent group means±SEM. *$p<0.05$. Bars indicate from left-to-right Groups 1-5.

FIG. 9A is a graph showing the calculated percent weight change from Day 0 in animals weighed twice weekly throughout the study. In FIG. 9B, animals underwent EchoMRI (QNMR) to measure body composition on days −4, 7, 14, 21, and 28 and percent lean mass change from Day 0 was calculated. Data represent group means±SEM. For both body weight and lean mass the mean percent change data for each group on day 28 of the study were analyzed using a one-way ANOVA followed by Holm-Sidak's post hoc test in comparison to the IgG Control Group (Group 2). *$p<0.0005$, $p<0.005$, *$p<0.05$, ns (not significant).

FIG. 10A shows the mean quadriceps weight, FIG. 10B shows the mean gastrocnemius weight, FIG. 10C shows the mean tibialis anterior weight, and FIG. 10D shows the mean diaphragm weight. Percent difference in mean muscle weights of the Ab1 treated groups compared to the IgG control group is noted above each bar. Statistical evaluation was performed using a one-way ANOVA followed by Holm-Sidak's post hoc test in comparison to the IgG Control Group (Group 2). Data represent group means±SEM. **$p<0.0001$, *$p<0.0005$, **$p<0.005$, *$p<0.05$, ns (not significant).

FIG. 11A shows the percent weight change from Day 0 calculated from animals weighed twice weekly throughout the study. (FIG. 11B) Animals underwent EchoMRI (QNMR) to measure body composition on days −1, 6, and 13 and percent lean mass change from Day −1 was calculated. PBS=phosphate buffered saline, Dex=dexamethasone, IgG (20)=IgG control antibody dosed at 20 mg/kg/wk, Ab1 (20)=Ab1 antibody dosed at 20 mg/kg/wk, and Ab1 (2)=Ab1 antibody dosed at 2 mg/kg/wk. Data represent group means±SEM. Mean percent change data for each group on day 14 (for body weight) and day 13 (for lean mass) were analyzed using a one-way ANOVA followed by a Dunnett's multiple comparisons test vs. group 1 (**$p<0.0001$, *$p<0.0005$, **$p<0.005$, *$p<0.05$) and vs. group 5 (++++$p<0.0001$, +++$p<0.0005$, ++$p<0.005$, +$p<0.05$). ns (not significant).

FIG. 12A shows the mean gastrocnemius weight (grams), FIG. 12B shows the mean quadriceps weight (grams), FIG. 12C shows the mean percent gastrocnemius weight change versus the control animals treated with PBS (IP) and normal drinking water (Group 1), and FIG. 12D shows the mean percent quadriceps weight change versus the control animals treated with PBS (IP) and normal drinking water (Group 1). PBS=phosphate buffered saline, Dex=dexamethasone, IgG (20)=IgG control antibody dosed at 20 mg/kg/wk, Ab1 (20)=Ab1 antibody dosed at 20 mg/kg/wk, and Ab1 (2)=Ab1 antibody dosed at 2 mg/kg/wk. For FIGS. 12A-12B, error bars represent standard deviation (SD). For FIGS. 12C-12D, error bars represent standard error of the mean (SEM). Statistical evaluation was performed using a one-way ANOVA followed by a Dunnett's multiple comparisons test vs. group 1 (**$p<0.0001$, *$p<0.0005$, **$p<0.005$, *$p<0.05$) and vs. group 5 (++++$p<0.0001$, +++$p<0.0005$, ++$p<0.005$, +$p<0.05$). ns (not significant). Bars indicate from left-to-right, PBS, water; PBS, dex; IgG Control; Ab1(20); and Ab1(2).

FIGS. 13A-13B show results of an assay evaluating the mean percent body weight and lean mass change. FIG. 13A shows the percent weight change from Day 0 calculated for animals who were weighed twice weekly throughout the study. FIG. 13B shows the percent lean mass change from Day −1 calculated from animals who underwent EchoMRI (QNMR) to measure body composition on days −1, 7, and 14. PBS=phosphate buffered saline, IgG (20)=IgG control antibody dosed at 20 mg/kg/wk, Ab1 (20)=Ab1 antibody dosed at 20 mg/kg/wk, and Ab1 (2)=Ab1 antibody dosed at 2 mg/kg/wk. Data represent group means±SEM.

FIG. 14A shows the mean gastrocnemius weight from the casted leg (grams), FIG. 14B shows the mean quadriceps weight from the casted leg (grams), FIG. 14C shows the mean percent gastrocnemius weight change versus the control animals treated with PBS (IP) and not casted (Group 1), and FIG. 14D shows the mean percent quadriceps weight change versus the control animals treated with PBS (IP) and not casted (Group 1). PBS=phosphate buffered saline, IgG (20)=IgG control antibody dosed at 20 mg/kg/wk, Ab1 (20)=Ab1 antibody dosed at 20 mg/kg/wk, and Ab1 (2)=Ab1 antibody dosed at 2 mg/kg/wk. For FIGS. 14A-14B, error bars represent standard deviation (SD). For FIGS. 14C-14D, error bars represent standard error of the mean (SEM). Statistical evaluation was performed using a one-way ANOVA followed by a Dunnett's multiple comparisons test vs. group 1 (**$p<0.0001$, *$p<0.0005$, **$p<0.005$, *$p<0.05$) and vs. group 5 (++++$p<0.0001$, +++$p<0.0005$, ++$p<0.005$, +$p<0.05$). ns (not significant). Bars indicate from left-to-right, PBS, no cast; PBS, casted; IgG Control; Ab1 (20); and Ab1(2).

FIG. 16A shows the domain structure of proMyostatin and latent Myostatin, with protease cleavage sites indicated. FIG. 16B shows partially proprotein convertase cleaved proMyostatin run on an SDS PAGE gel. Under reducing conditions, the protein bands consisted of the proMyostatin monomer (~50 kD), prodomain (~37 kD) and growth factor (12.5 kD).

FIG. 17A shows Ab1 binds specifically to proMyostatin and latent Myostatin, with no binding observed to other members of the TGFB superfamily, most notably the corresponding forms of GDF11. Ab1 was administered at a high concentration (50 ug/mL) to Forte-Bio BLI tips coated with the indicated antigen and the on and off rates were measured to obtain an approximate Kd value. The magnitude of biosensor response, indicating a binding event, is graphically represented by black bars, and the calculated Kd is indicated in orange. FIG. 17B shows that Ab1 blocks the activation of proMyostatin, but not proGDF11. Following an overnight proteolysis reaction with enzymes from both the proprotein-convertase and tolloid protease families, the release of mature growth factor was measured using a CAGA-based reporter assay in 293T cells. Results were compared to control reactions to calculate the fraction of proMyostatin or proGDF11 which was released in the assay.

FIGS. 18A-18C show the SCID dose response with the candidate antibodies. FIG. 18A shows the muscle weight of the gastrocnemius and FIG. 18B shows the muscle weight of the quadriceps. FIG. 18C shows the percent changes in mean muscle weight compared to the PBS control.

FIGS. 21A-21B show the heavy chain (FIG. 21A; SEQ ID NO: 50) and light chain (FIG. 21B; SEQ ID NO: 51) of a humanized monoclonal antibody (Ab2) of the IgG4 subtype with Proline substituted for Serine. This generates an IgG1-like hinge sequence and minimizes the incomplete formation of inter-chain disulfide bridges which is characteristic of IgG4. The complementarity-determining regions (CDRs) are underlined. purple: N-linked glycosylation consensus sequence site; light blue: potential cleavage site; red: potential deamidation site; light green: potential isomerization site; Dark blue: potential methionine oxidation site; Bold: expected N-terminal pyroglutamic acid.

FIG. 23C shows the affinity-matured variants have a slower off-rate by octet as well.

FIGS. 24A-24B show sequence alignments of the variable heavy regions (FIG. 24A) and variable light regions (FIG. 24B) of parental Ab1 with affinity optimized variants, Ab3 and Ab5. Sequence identifiers from top to bottom correspond to SEQ ID NOs.: 24, 26, 28 (FIG. 24A). Sequence identifiers from top to bottom correspond to SEQ ID NOs.: 30, 32, 34 (FIG. 24B). Complementarity-determining regions (CDRs) are defined using the Kabat (underlined) and IMGT nomenclature (bold). Substitutions from parental Ab1 are shown in red.

DETAILED DESCRIPTION

Figure 1A:
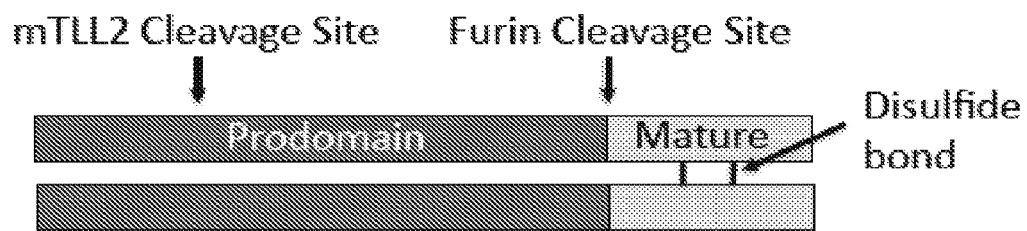
FIGS. 1A-1B show Myostatin domain structure and pro-Myostatin assembly.
Figure 1B:
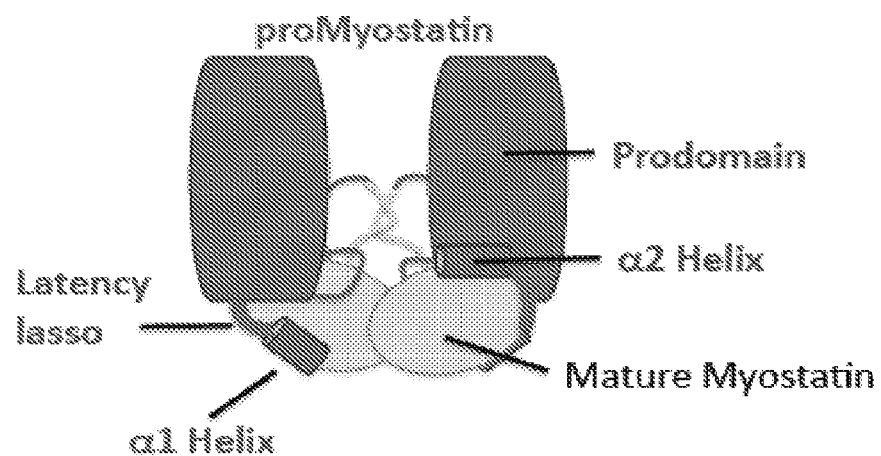

Myostatin is a member of the TGFβ superfamily, and belongs to a subfamily including two members: Myostatin (also known as GDF8) and GDF11. Like other members of the TGFβ superfamily, Myostatin and GDF11 are both initially expressed as inactive precursor polypeptides (termed proMyostatin and proGDF11, respectively). The domain structure and nomenclature are shown in FIG. 1A. FIG. 1B illustrates a cartoon model of the overall structure of proMyostatin, where the mature growth factor is held locked in a cage comprised of two alpha helices connected by a loop termed the "latency lasso".

Figure 2:
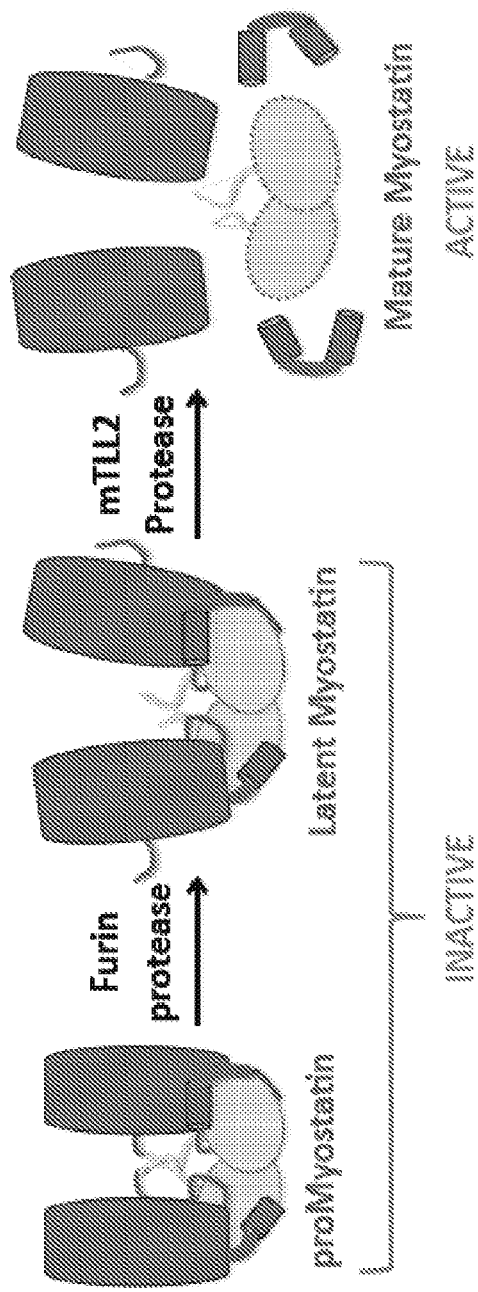
FIG. 2 shows that the activation of Myostatin involves two distinct protease events, generating at least three Myostatin species. The biosynthetic precursor protein, proMyostatin, is processed by two separate proteases. The first step shown in this schematic is performed by a member of the proprotein convertase family, such as Furin. This cleavage separates the prodomain from the mature growth factor. The second cleavage event, by the tolloid family of proteases, cleaves the prodomain. These cleavage events yield a mature form of Myostatin, which may be referred to as Active Myostatin or Mature Myostatin.

Activation and release of the mature growth factor is accomplished by several discrete protease cleavage events, outlined in FIG. 2. The first cleavage step of proMyostatin and proGDF11 is carried out by a proprotein convertase, which cuts at a conserved RXXR site between the prodomain and mature growth factor. This cleavage produces a latent complex, in which the mature growth factor is shielded from binding to its receptors by the prodomain Activation and release of the mature, active Myostatin growth factor is accomplished after cleavage by an additional protease from the BMP/tolloid family, such as mTLL-2 (FIG. 2).

Exemplary proGDF8 sequences in the human, rat, mouse and cynomolgus are provided below. In these proGDF8 sequences, a proprotein convertase cleavage site is indicated in bold and a tolloid protease site is indicated by underlining. In some embodiments, the proprotein convertase cleavage site comprises amino acid residues 240 to 243 of SEQ ID NOs: 52-55. In some embodiments, the tolloid protease site comprises amino acid residues 74-75 of SEQ ID NOs: 52-55. It should be appreciated that the exemplary proGDF8 sequences provided herein are not intended to be limiting and additional proGDF8 sequences from other species, including any isoforms thereof, are within the scope of this disclosure.

```
proGDF8 (human):
                                          (SEQ ID NO: 52)
NENSEQKENVEKEGLCNACTWRQNTKSSRIEAIKIQILSKLRLETAPNIS

KDVIRQLLPKAPPLRELIDQYDVQRDDSSDGSLEDDDYHATTETIITMPT

ESDFLMQVDGKPKCCFFKFSSKIQYNKVVKAQLWIYLRPVETPTTVFVQI

LRLIKPMKDGTRYTGIRSLKLDMNPGTGIWQSIDVKTVLQNWLKQPESNL

GIEIKALDENGHDLAVTFPGPGEDGLNPFLEVKVTDTPKRSRRDFGLDCD

EHSTESRCCRYPLTVDFEAFGWDWIIAPKRYKANYCSGECEFVFLQKYPH

THLVHQANPRGSAGPCCTPTKMSPINMLYFNGKEQIIYGKIPAMVVDRCG

CS.

proGDF8 (rat):
                                          (SEQ ID NO: 53)
NEDSEREANVEKEGLCNACAWRQNTRYSRIEAIKIQILSKLRLETAPNIS

KDAIRQLLPRAPPLRELIDQYDVQRDDSSDGSLEDDDYHATTETIITMPT

ESDFLMQADGKPKCCFFKFSSKIQYNKVVKAQLWIYLRAVKTPTTVFVQI

LRLIKPMKDGTRYTGIRSLKLDMSPGTGIWQSIDVKTVLQNWLKQPESNL

GIEIKALDENGHDLAVTFPGPGEDGLNPFLEVKVTDTPKRSRRDFGLDCD

EHSTESRCCRYPLTVDFEAFGWDWIIAPKRYKANYCSGECEFVFLQKYPH

THLVHQANPRGSAGPCCTPTKMSPINMLYFNGKEQIIYGKIPAMVVDRCG

CS.

pro GDF8 (mouse):
                                          (SEQ ID NO: 54)
NEGSEREENVEKEGLCNACAWRQNTRYSRIEAIKIQILSKLRLETAPNIS

KDAIRQLLPRAPPLRELIDQYDVQRDDSSDGSLEDDDYHATTETIITMPT

ESDFLMQADGKPKCCFFKFSSKIQYNKVVKAQLWIYLRPVKTPTTVFVQI

LRLIKPMKDGTRYTGIRSLKLDMSPGTGIWQSIDVKTVLQNWLKQPESNL

GIEIKALDENGHDLAVTFPGPGEDGLNPFLEVKVTDTPKRSRRDFGLDCD

EHSTESRCCRYPLTVDFEAFGWDWIIAPKRYKANYCSGECEFVFLQKYPH

THLVHQANPRGSAGPCCTPTKMSPINMLYFNGKEQIIYGKIPAMVVDRCG

CS.

proGDF8 (cynonnolgus):
                                          (SEQ ID NO: 55)
NENSEQKENVEKEGLCNACTWRQNTKSSRIEAIKIQILSKLRLETAPNIS

KDAIRQLLPKAPPLRELIDQYDVQRDDSSDGSLEDDDYHATTETIITMPT

ESDFLMQVDGKPKCCFFKFSSKIQYNKVVKAQLWIYLRPVETPTTVFVQI

LRLIKPMKDGTRYTGIRSLKLDMNPGTGIWQSIDVKTVLQNWLKQPESNL

GIEIKALDENGHDLAVTFPGPGEDGLNPFLEVKVTDTPKRSRRDFGLDCD

EHSTESRCCRYPLTVDFEAFGWDWIIA.
```

Myostatin and GDF11 share a relatively high degree of conservation between their mature growth factor domains, with ninety percent identity, but are much less well conserved in their prodomain regions with less than fifty percent amino acid identity between the two. Myostatin and GDF11 bind and signal through the same receptors consisting of a Type I receptor (ALK4/5) in association with a type II receptor (ACTRIIA/B). Engagement of Myostatin with Type I and Type II receptors initiates a signaling cascade leading to SMAD phosphorylation and transcriptional activation of muscle atrophy genes. The relatively high degree of conservation in the mature growth factors has made it challenging to identify reagents, such as monoclonal antibodies, that can differentiate between mature Myostatin and GDF11.

Role of Myostatin in Myopathies

Skeletal muscle accounts for approximately 40% of body mass and is a dynamic organ, turning over at a rate of 1-2% per day. Muscle atrophy is a highly regulated catabolic process which occurs during periods of disuse (e.g. disuse atrophy) and/or in response to heightened systemic inflammation (cachexia). In disuse atrophy, which can occur during prolonged periods of immobilization such as during bed rest, muscle loss occurs rapidly. For example, during a hospital stay of one week, an average patient loses ~1.3 kg of muscle mass.

Muscle atrophy causes significant morbidity in a wide range of clinical conditions. In diseases of denervation like amyotrophic lateral sclerosis (ALS) or spinal muscular atrophy (SMA) and genetic diseases including muscular dystrophies, loss of muscle strength and function are highly disabling clinical manifestations for which there are no adequate treatments. In cachexia syndromes due to renal failure, AIDS, cardiac conditions, or cancer, muscle wasting often undermines successful treatment of the primary condition. Muscle loss also results as a natural process of aging and in its most severe form is categorized as sarcopenia, a pervasive condition among the elderly that is increasingly being recognized as a pathology warranting intervention. Lastly, a major driver of muscle atrophy is disuse. Immobilization causes rapid and significant muscle loss in a large group of conditions such as hip fracture, elective joint replacement, spinal cord injury, critical care myopathy and stroke. While varied in their cause, these indications share a characteristic of muscle weakness, which leads to significant disability, lengthy physical rehabilitation and recovery times and impairment of quality of life.

There has been an unmet medical need in muscle atrophy conditions. Accordingly, in some embodiments, methods are provided herein for treating muscle atrophy. In some embodiments, methods provided herein relate to the treatment of a primary myopathy. In some embodiments, methods provided herein relate to the treatment of secondary myopathy, such as, for example, diseases of denervation, genetic muscle weakness and cachexia, conditions in which muscle loss is secondary to the disease pathology. In some embodiments, methods provided herein for the treatment of primary myopathies, such as disuse atrophy (e.g., associated with hip fracture or spinal cord injury (SCI)), result in increase in muscle mass, strength and function in a subject.

Myostatin Pathway Inhibition

There are several Myostatin pathway antagonists in various stages of clinical development towards the treatment of muscle-related conditions. Such pathway antagonists target either the mature growth factor or its type II receptor, and most antagonize the signaling of multiple TGFβ family members. For example, a number of current clinical candidates block additional growth factors such as Activin A, GDF11, and BMPs 9 and 10, which are regulators of reproductive biology, wound healing, erythropoiesis and blood vessel formation, respectively. Aspects of this disclosure relate to a recognition that blocking these factors in addition to Myostatin will potentially limit the population of patients who can safely undergo therapy due to unacceptable side-effects.

Accordingly, provided herein are antibodies capable of binding to proMyostatin and/or latent Myostatin, thereby inhibiting Myostatin activity, and uses thereof for treating diseases and disorders associated with myopathy. In some embodiments, given the prevalence of the latent complex in circulation, treatments are provided herein that specifically target more abundant and longer-lived Myostatin precursors e.g., proMyostatin and latent Myostatin, rather than the mature growth factor. Without wishing to be bound by any particular theory, antibodies provided herein may prevent the proteolytic activation of proMyostatin and/or latent Myostatin into mature Myostatin which is considered the "active" form of Myostatin, capable of activating the Myostatin pathway, e.g., by binding Type I (ALK4/5) and Type II (ACTRIIA/B) receptors. As used herein, the term "pro/latent-Myostatin" refers to proMyostatin, latent Myostatin, or both. In some embodiments, an anti-pro/latent Myostatin antibody binds specifically to proMyostatin. In some embodiments, an anti-pro/latent Myostatin antibody binds specifically to latentMyostatin. In some embodiments, an anti-pro/latent Myostatin antibody binds specifically to both latentMyostatin and proMyostatin.

Antibodies that Bind Pro/Latent-Myostatin

The present disclosure is based, at least in part, on the surprising discovery that certain pro/latent-Myostatin-specific antibodies (e.g., an antibody referred to herein as Ab1), prevented proteolytic activation of pro/latent-Myostatin into mature Myostatin. Furthermore, inhibition of Myostatin activation using such antibodies was effective for increasing muscle mass in both dexamethasone and casting induced muscle atrophy mouse models. Aspects of the disclosure provide antibodies (e.g., antibodies and antigen binding fragments) that bind to pro/latent-Myostatin and inhibit proteolytic activation of pro/latent-Myostatin into mature Myostatin.

An antibody (interchangeably used in plural form) is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody" encompasses not only intact (e.g., full-length) polyclonal or monoclonal antibodies, but also antigen-binding fragments thereof (such as Fab, Fab', F(ab')2, Fv), single chain (scFv), mutants thereof, fusion proteins comprising an antibody portion, humanized antibodies, chimeric antibodies, diabodies, linear antibodies, single chain antibodies, multispecific antibodies (e.g., bispecific antibodies) and any other modified configuration of the immunoglobulin molecule that comprises an antigen recognition site of the required specificity, including glycosylation variants of antibodies, amino acid sequence variants of antibodies, and covalently modified antibodies. An antibody includes an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

Antibodies described herein are capable of binding to a pro/latent-Myostatin, thereby inhibiting the proteolytic activation of pro/latent-Myostatin into mature Myostatin. In some instances, antibodies described herein can inhibit the proteolytic activation of pro/latent-Myostatin by at least 20%, e.g., 30%, 40%, 50%, 60%, 70%, 80%, 90%, 95%, or higher. In some instances, antibodies described herein can inhibit the proteolytic cleavage of proMyostatin by a proprotein convertase (e.g., furin) by at least 20%, e.g., 30%, 40%, 50%, 60%, 70%, 80%, 90%, 95%, or higher. In some instances antibodies described herein can inhibit the proteolytic cleavage of proMyostatin or latent Myostatin by a tolloid protease (e.g., mTLL2) by at least 20%, e.g., 30%, 40%, 50%, 60%, 70%, 80%, 90%, 95%, or higher. The inhibitory activity of an anti-pro/latent-Myostatin antibody can be measured by routine methods, for example, by Western blot analysis as described in Example 1 and FIG. 3. However, it should be appreciated that additional methods may be used for measuring the inhibitory activity of an anti-pro/latent-Myostatin antibody on proteolytic cleavage of pro/latent-Myostatin. In some embodiments, inhibition of pro/latent-Myostatin cleavage (e.g., by a proprotein convertase and/or tolloid protease) may be reflected as an inhibition constant (Ki), which provides a measure of inhibitor potency, and which it is the concentration of inhibitor (e.g., an anti-pro/latent-Myostatin antibody) required to reduce protease activity (e.g., of a proprotein convertase or tolloid protease) by half and is not dependent on enzyme or substrate concentrations.

In some embodiments, a proprotein convertase comprises (i) a catalytic domain that hydrolyzes a peptide bond of a protein containing a proprotein convertase cleavage site, and (ii) a binding pocket that binds to an rTGF with a proprotein convertase cleavage site. Examples of proprotein convertases for use in accordance with the present disclosure include, without limitation, PCSK5/6, PACE4, PACE7 and PACE3 (e.g., furin). A proprotein convertase, in some embodiments, is obtained from any mammal including, without limitation, humans, monkeys or rodents (e.g., mice, rats, hamsters).

In some embodiments, a proprotein convertase is homologous to a proprotein convertase selected from the group consisting of: PCSK5/6, PACE4, PACE7 and PACE3 (e.g., furin). For example a proprotein convertase may be at least 70% identical, at least 80% identical, at least 90% identical, at least 95% identical, at least 96% identical, at least 97% identical, at least 98% identical, at least 99% identical, at least 99.5% identical, or at least about 99.9% identical to PCSK5/6, PACE4, PACE7 or PACE3 (e.g., furin).

A proprotein convertase cleavage site, in some embodiments, is an amino sequence that can be cleaved by a proprotein convertase (e.g., PCSK5/6, PACE4, PACE7 and PACE3). In some embodiments, the proprotein convertase cleavage site comprises the amino acid sequence R-X-X-R, where R is arginine and X is any amino acid. In some embodiments, the proprotein convertase cleavage site comprises the amino acid sequence R-X-(K/R)-R, where R is arginine, K is lysine and X is any amino acid. In some embodiments, the proprotein convertase cleavage site comprises the amino acid sequence is R-V-R-R (SEQ ID NO:

57), where R is arginine and V is valine. Exemplary proprotein convertase cleavage sites for human, rat, mouse, and cynomolgus myostatin are shown, in bold, in SEQ ID NOs: 52-55. In some embodiments, the proprotein convertase cleavage site comprises the amino acid sequence RSRR (SEQ ID NO: 56).

In some embodiments, tolloid proteases for use in accordance with the present disclosure include, without limitation, BMP-1, mTLL-1 and mTLL-2. A tolloid protease may be obtained from any mammal including, without limitation, humans, monkeys, or rodents (e.g., mice, rats, hamsters). In some embodiments, a tolloid protease is homologous to a tolloid protease selected from the group consisting of: BMP-1, mTLL-1 and mTLL-2. For example a tolloid protease may be at least 70% identical, at least 80% identical, at least 90% identical, at least 95% identical, at least 96% identical, at least 97% identical, at least 98% identical, at least 99% identical, at least 99.5% identical, or at least about 99.9% identical to BMP-1, mTLL-1 and mTLL-2.

A tolloid protease cleavage site, in some embodiments, is an amino sequence that can be cleaved by a tolloid (e.g., BMP-1, mTLL-1 and mTLL-2). Exemplary tolloid protease cleavage sites for human, rat, mouse, and cynomolgus myostatin are shown, in underlining, in SEQ ID NOs: 52-55. In some embodiments, the tolloid cleavage site comprises the amino acid sequence QR, where Q is glutamine and R is arginine.

In some embodiments, antibodies described herein are capable of binding to a pro/latent-Myostatin, thereby inhibiting Myostatin activity. In some instances, the antibodies described herein can inhibit Myostatin signaling by at least 20%, e.g., 30%, 40%, 50%, 60%, 70%, 80%, 90%, 95%, or higher. In some embodiments, inhibition of Myostatin signaling can be measured by routine methods, for example, using a Myostatin activation assay as described in Example 1. However, it should be appreciated that additional methods may be used for measuring Myostatin signaling activity.

It should be appreciated that the extent of proteolytic cleavage of myostatin, e.g., by a proprotein convertase and/or a tolloid protease, can be measured and/or quantified using any suitable method. In some embodiments, the extent of proteolytic cleavage of myostatin is measured and/or quantified using an enzyme-linked immunosorbent assay (ELISA). For example, an ELISA may be used to measure the level of released growth factor (e.g., mature myostatin). As another example, an antibody that specifically binds to proMyostatin, latent Myostatin and/or mature Myostatin can be used in an ELISA to measure the level of a specific form of myostatin (e.g., pro/latent/mature-Myostatin), to quantify the extent of proteolytic cleavage of myostatin. In some embodiments, the extent of proteolytic cleavage of myostatin is measured and/or quantified using immunoprecipitation followed by SDS-PAGE or mass spectrometry of tryptic peptides, fluorescence anisotropy-based techniques, FRET assays, hydrogen-deuterium-exchange mass spectrometry, and/or NMR spectroscopy.

In some embodiments, antibodies, also known as immunoglobulins, are tetrameric glycosylated proteins composed of two light (L) chains of approximately 25 kDa each and two heavy (H) chains of approximately 50 kDa each. Two types of light chain, termed lambda and kappa, may be found in antibodies. Depending on the amino acid sequence of the constant domain of heavy chains, immunoglobulins can be assigned to five major classes: A, D, E, G, and M, and several of these may be further divided into subclasses (isotypes), e.g., $IgG_1$, $IgG_2$, $IgG_3$, $IgG_4$, $IgA_1$, and $IgA_2$. Each light chain typically includes an N-terminal variable (V) domain ($V_L$) and a constant (C) domain ($C_L$). Each heavy chain typically includes an N-terminal V domain ($V_H$), three or four C domains ($C_H$1-3), and a hinge region. The $C_H$ domain most proximal to $V_H$ is designated as $C_H$1. The $V_H$ and $V_L$ domains consist of four regions of relatively conserved sequences called framework regions (FR1, FR2, FR3, and FR4), which form a scaffold for three regions of hypervariable sequences (complementarity determining regions, CDRs). The CDRs contain most of the residues responsible for specific interactions of the antibody with the antigen. CDRs are referred to as CDR1, CDR2, and CDR3. Accordingly, CDR constituents on the heavy chain are referred to as CDRH1, CDRH2, and CDRH3, while CDR constituents on the light chain are referred to as CDRL1, CDRL2, and CDRL3. The CDRs typically refer to the Kabat CDRs, as described in Sequences of Proteins of Immunological Interest, US Department of Health and Human Services (1991), eds. Kabat et al. Another standard for characterizing the antigen binding site is to refer to the hypervariable loops as described by Chothia. See, e.g., Chothia, D. et al. (1992) J. Mol. Biol. 227:799-817; and Tomlinson et al. (1995) EMBO J. 14:4628-4638. Still another standard is the AbM definition used by Oxford Molecular's AbM antibody modeling software. See, generally, e.g., Protein Sequence and Structure Analysis of Antibody Variable Domains. In: Antibody Engineering Lab Manual (Ed.: Duebel, S, and Kontermann, R., Springer-Verlag, Heidelberg). Embodiments described with respect to Kabat CDRs can alternatively be implemented using similar described relationships with respect to Chothia hypervariable loops or to the AbM-defined loops, or combinations of any of these methods.

In some embodiments, anti-pro/latent-Myostatin antibodies of the present disclosure and the nucleic acid molecules of the present disclosure that encode the antibodies include the CDR amino acid sequences shown in Table 1.

TABLE 1

| Antibody | CDRH1 (SEQ ID NOs: 1-3) | CDRH2 (SEQ ID NOs: 4-9) | CDRH3 (SEQ ID NOs: 10-11) | CDRL1 (SEQ ID NOs: 12-17) | CDRL2 (SEQ ID NOs: 18-21) | CDRL3 (SEQ ID NOs: 22-23) |
|---|---|---|---|---|---|---|
| Ab1 Kabat: IMGT: | SSYGMH (SEQ ID NO: 1) GFTFSSYGMH (SEQ ID NO: 2) | VISYDGSNKYY ADSVKG (SEQ ID NO: 4) ISYDGSN (SEQ ID NO: 5) | DLLVRFLEWSH YYGMDV (SEQ ID NO: 10) | SGSSSNIGSNTV H (SEQ ID NO: 12) SSNIGSNT (SEQ ID NO: 13) | SDNQRPS (SEQ ID NO: 18) SDN (SEQ ID NO: 19) | AAWDDSLNGV (SEQ ID NO: 22) |
| Ab3 Kabat: IMGT: | SSYGMH (SEQ ID NO: 1) GFAFSSYGMH (SEQ ID NO: 3) | VISYDGSIKYYA DSVKG (SEQ ID NO: 6) ISYDGSI (SEQ ID NO: 7) | DLLVRFLEWSH KYGMDV (SEQ ID NO: 11) | SGSTSNIGSNTV H (SEQ ID NO: 14) TSNIGSNT (SEQ ID NO: 15) | SDDQRPS (SEQ ID NO: 20) SDD (SEQ ID NO: 21) | AAWDESLNGV (SEQ ID NO: 23) |

TABLE 1-continued

| Antibody | CDRH1 (SEQ ID NOs: 1-3) | CDRH2 (SEQ ID NOs: 4-9) | CDRH3 (SEQ ID NOs: 10-11) | CDRL1 (SEQ ID NOs: 12-17) | CDRL2 (SEQ ID NOs: 18-21) | CDRL3 (SEQ ID NOs: 22-23) |
|---|---|---|---|---|---|---|
| Ab5 Kabat: IMGT: | SSYGMH (SEQ ID NO: 1) GFAFSSYGMH (SEQ ID NO: 3) | VISYDGNNKYY ADSVKG (SEQ ID NO: 8) ISYDGNN (SEQ ID NO: 9) | DLLVRFLEWSH KYGMDV (SEQ ID NO: 11) | SGSSSNIGGNTV H (SEQ ID NO: 16) SSNIGGNT (SEQ ID NO: 17) | SDDQRPS (SEQ ID NO: 20) SDD (SEQ ID NO: 21) | AAWDESLNGV (SEQ ID NO: 23) |

In Table 1, the single sequences of CDRH3 and CDRL3 reflect Kabat and IMGT.

In some embodiments, anti-pro/latent-Myostatin binding agents (e.g., antibodies) of the disclosure include any antibody (including antigen binding fragments) that includes a CDRH1, CDRH2, CDRH3, CDRL1, CDRL2, or CDRL3, or combinations thereof, as provided for any one of the antibodies shown in Table 1. In some embodiments, anti-pro/latent-Myostatin binding agents include the CDRH1, CDRH2, CDRH3, CDRL1, CDRL2, and CDRL3 of any one of the antibodies shown in Table 1. The disclosure also includes any nucleic acid sequence that encodes a molecule comprising a CDRH1, CDRH2, CDRH3, CDRL1, CDRL2, or CDRL3 as provided for any one of the antibodies shown in Table 1. Antibody heavy and light chain CDR3 domains may play a particularly important role in the binding specificity/affinity of an antibody for an antigen. Accordingly, the anti-pro/latent-Myostatin binding agents of the disclosure, or the nucleic acid molecules thereof, may include at least the heavy and/or light chain CDR3s of antibodies as shown in Table 1.

Aspects of the disclosure relate to a monoclonal antibody or antigen binding fragment, that binds to pro/latent-Myostatin protein and that comprises six complementarity determining regions (CDRs): CDRH1, CDRH2, CDRH3, CDRL1, CDRL2, and CDRL3.

In some embodiments, CDRH1 comprises a sequence as set forth in any one of SEQ ID NOs: 1-3. In some embodiments, CDRH2 comprises a sequence as set forth in any one of SEQ ID NOs: 4-9. In some embodiments, CDRH3 comprises a sequence as set forth in any one of SEQ ID NOs: 10-11. CDRL1 comprises a sequence as set forth in any one of SEQ ID NOs: 12-17. In some embodiments, CDRL2 comprises a sequence as set forth in any one of SEQ ID NOs: 18-21. In some embodiments, CDRL3 comprises a sequence as set forth in any one of SEQ ID NOs: 22-23.

In some embodiments (e.g., as for anti-pro/latent-Myostatin antibody Ab1, shown in Table 1), CDRH1 comprises a sequence as set forth in SEQ ID NO: 1 or 2, CDRH2 comprises a sequence as set forth in SEQ ID NO: 4 or 5, CDRH3 comprises a sequence as set forth in SEQ ID NO: 10, CDRL1 comprises a sequence as set forth in SEQ ID NO: 12, or 13, CDRL2 comprises a sequence as set forth in SEQ ID NO: 18 or 19, and CDRL3 comprises a sequence as set forth in SEQ ID NO: 22, and the antibody binds to pro/latent-Myostatin.

In some embodiments (e.g., as for anti-pro/latent-Myostatin antibody Ab3, shown in Table 1), CDRH1 comprises a sequence as set forth in SEQ ID NO: 1 or 3, CDRH2 comprises a sequence as set forth in SEQ ID NO: 6 or 7, CDRH3 comprises a sequence as set forth in SEQ ID NO: 11, CDRL1 comprises a sequence as set forth in SEQ ID NO: 14, or 15, CDRL2 comprises a sequence as set forth in SEQ ID NO: 20 or 21, and CDRL3 comprises a sequence as set forth in SEQ ID NO: 23, and the antibody binds to pro/latent-Myostatin.

In some embodiments (e.g., as for anti-pro/latent-Myostatin antibody Ab5, shown in Table 1), CDRH1 comprises a sequence as set forth in SEQ ID NO: 1 or 3, CDRH2 comprises a sequence as set forth in SEQ ID NO: 8 or 9, CDRH3 comprises a sequence as set forth in SEQ ID NO: 11, CDRL1 comprises a sequence as set forth in SEQ ID NO: 16, or 17, CDRL2 comprises a sequence as set forth in SEQ ID NO: 20 or 21, and CDRL3 comprises a sequence as set forth in SEQ ID NO: 23, and the antibody binds to pro/latent-Myostatin. In some examples, any of the anti-pro/latent-Myostatin binding agents (e.g., antibodies) of the disclosure include any antibody (including antigen binding fragments) having one or more CDR (e.g., CDRH or CDRL) sequences substantially similar to CDRH1, CDRH2, CDRH3, CDRL1, CDRL2, and/or CDRL3. For example, the antibodies may include one or more CDR sequences as shown in Table 1 (SEQ ID NOs: 1-23) containing up to 5, 4, 3, 2, or 1 amino acid residue variations as compared to the corresponding CDR region in any one of SEQ ID NOs: 1-23. The complete amino acid and nucleic acid sequences for the heavy chain variable region and light chain variable region of the antibodies listed in Table 1 are provided below.

Heavy chain variable region - Ab1 parental
(SEQ ID NO: 24)
QIQLVQSGGGVVQPGRSLRLSCAASGFTFSSYGMHWVRQAPGKGLEWVAV

ISYDGSNKYYADSVKGRFTISRDNSKNTLYLQMNSLRAEDTAVYYCARDL

LVRFLEWSHYYGMDVWGQGTTVTVSS (SEQ ID NO: 38)
CAGATCCAGCTGGTGCAGTCTGGGGGAGGCGTGGTCCAGCCTGGGAGGTC

CCTGAGACTCTCCTGTGCAGCGTCTGGATTCACCTTCAGTAGCTATGGCA

TGCACTGGGTCCGCCAGGCTCCAGGCAAGGGGCTGGAGTGGGTGGCAGTT

ATATCATATGATGGAAGTAATAAATACTATGCAGACTCCGTGAAGGGCCG

ATTCACCATCTCCAGAGACAATTCCAAGAACACGCTGTATCTGCAAATGA

ACAGCCTGAGAGCCGAGGACACGGCTGTGTATTACTGTGCGAGAGATCTC

CTGGTGCGATTTTTGGAGTGGTCGCACTACTACGGTATGGACGTCTGGGG

CCAAGGGACCACGGTCACCGTCTCCTCA

Heavy chain variable region - Ab2 germline
(SEQ ID NO: 25)
QVQLVESGGGVVQPGRSLRLSCAASGFTFSSYGMHWVRQAPGKGLEWVAV

ISYDGSNKYYADSVKGRFTISRDNSKNTLYLQMNSLRAEDTAVYYCARDL

LVRFLEWSHYYGMDVWGQGTTVTVSS

-continued

```
                                               (SEQ ID NO: 39)
CAGGTGCAGCTGGTGGAGTCTGGGGGAGGCGTGGTCCAGCCTGGGAGGTC

CCTGAGACTCTCCTGTGCAGCGTCTGGATTCACCTTCAGTAGCTATGGCA

TGCACTGGGTCCGCCAGGCTCCAGGCAAGGGGCTGGAGTGGGTGGCAGTT

ATATCATATGATGGAAGTAATAAATACTATGCAGACTCCGTGAAGGGCCG

ATTCACCATCTCCAGAGACAATTCCAAGAACACGCTGTATCTGCAAATGA

ACAGCCTGAGAGCCGAGGACACGGCTGTGTATTACTGTGCGAGAGATCTC

CTGGTGCGATTTTTGGAGTGGTCGCACTACTACGGTATGGACGTCTGGGG

CCAAGGGACCACGGTCACCGTCTCCTCA

Heavy chain variable region - Ab3 parental
                                               (SEQ ID NO: 26)
QIQLVQSGGGVVQPGRSLRLSCAASGFAFSSYGMHWVRQAPGKGLEWVAV

ISYDGSIKYYADSVKGRFTISRDNSKNTLYLQMNSLRAEDTAVYYCARDL

LVRFLEWSHKYGMDVWGQGTTVTVSS
                                               (SEQ ID NO: 40)
CAGATCCAGCTGGTGCAGTCTGGGGGAGGCGTGGTCCAGCCTGGGAGGTC

CCTGAGACTCTCCTGTGCAGCGTCTGGATTCGCCTTCAGTAGCTATGGCA

TGCACTGGGTCCGCCAGGCTCCAGGCAAGGGGCTGGAGTGGGTGGCAGTT

ATATCATATGATGGAAGTATCAAATACTATGCAGACTCCGTGAAGGGCCG

ATTCACCATCTCCAGAGACAATTCCAAGAACACGCTGTATCTGCAAATGA

ACAGCCTGAGAGCCGAGGACACGGCTGTGTATTACTGTGCGAGAGATCTC

CTGGTGCGATTTTTGGAGTGGTCGCACAAGTACGGTATGGACGTCTGGGG

CCAAGGGACCACGGTCACCGTCTCCTCA

Heavy chain variable region - Ab4 germline
                                               (SEQ ID NO: 27)
QVQLVESGGGVVQPGRSLRLSCAASGFAFSSYGMHWVRQAPGKGLEWVAV

ISYDGSIKYYADSVKGRFTISRDNSKNTLYLQMNSLRAEDTAVYYCARDL

LVRFLEWSHKYGMDVWGQGTTVTVSS
                                               (SEQ ID NO: 41)
CAGGTGCAGCTGGTGGAGTCTGGGGGAGGCGTGGTCCAGCCTGGGAGGTC

CCTGAGACTCTCCTGTGCAGCGTCTGGATTCGCCTTCAGTAGCTATGGCA

TGCACTGGGTCCGCCAGGCTCCAGGCAAGGGGCTGGAGTGGGTGGCAGTT

ATATCATATGATGGAAGTATCAAATACTATGCAGACTCCGTGAAGGGCCG

ATTCACCATCTCCAGAGACAATTCCAAGAACACGCTGTATCTGCAAATGA

ACAGCCTGAGAGCCGAGGACACGGCTGTGTATTACTGTGCGAGAGATCTC

CTGGTGCGATTTTTGGAGTGGTCGCACAAGTACGGTATGGACGTCTGGGG

CCAAGGGACCACGGTCACCGTCTCCTCA

Heavy chain variable region - Ab5 parental
                                               (SEQ ID NO: 28)
QIQLVQSGGGVVQPGRSLRLSCAASGFAFSSYGMHWVRQAPGKGLEWVAV

ISYDGNNKYYADSVKGRFTISRDNSKNTLYLQMNSLRAEDTAVYYCARDL

LVRFLEWSHKYGMDVWGQGTTVTVSS
                                               (SEQ ID NO: 42)
CAGATCCAGCTGGTGCAGTCTGGGGGAGGCGTGGTCCAGCCTGGGAGGTC

CCTGAGACTCTCCTGTGCAGCGTCTGGATTCGCCTTCAGTAGCTATGGCA

TGCACTGGGTCCGCCAGGCTCCAGGCAAGGGGCTGGAGTGGGTGGCAGTT

ATATCATATGATGGAAATAATAAATACTATGCAGACTCCGTGAAGGGCCG

ATTCACCATCTCCAGAGACAATTCCAAGAACACGCTGTATCTGCAAATGA

ACAGCCTGAGAGCCGAGGACACGGCTGTGTATTACTGTGCGAGAGATCTC

CTGGTGCGATTTTTGGAGTGGTCGCACAAGTACGGTATGGACGTCTGGGG

CCAAGGGACCACGGTCACCGTCTCCTCA

Heavy chain variable region - Ab6 germline
                                               (SEQ ID NO: 29)
QVQLVESGGGVVQPGRSLRLSCAASGFAFSSYGMHWVRQAPGKGLEWVAV

ISYDGNNKYYADSVKGRFTISRDNSKNTLYLQMNSLRAEDTAVYYCARDL

LVRFLEWSHKYGMDVWGQGTTVTVSS
                                               (SEQ ID NO: 43)
CAGGTGCAGCTGGTGGAGTCTGGGGGAGGCGTGGTCCAGCCTGGGAGGTC

CCTGAGACTCTCCTGTGCAGCGTCTGGATTCGCCTTCAGTAGCTATGGCA

TGCACTGGGTCCGCCAGGCTCCAGGCAAGGGGCTGGAGTGGGTGGCAGTT

ATATCATATGATGGAAATAATAAATACTATGCAGACTCCGTGAAGGGCCG

ATTCACCATCTCCAGAGACAATTCCAAGAACACGCTGTATCTGCAAATGA

ACAGCCTGAGAGCCGAGGACACGGCTGTGTATTACTGTGCGAGAGATCTC

CTGGTGCGATTTTTGGAGTGGTCGCACAAGTACGGTATGGACGTCTGGGG

CCAAGGGACCACGGTCACCGTCTCCTCA

Light chain variable region - Ab1 parental
                                               (SEQ ID NO: 30)
QPVLTQPPSASGTPGQRVTISCSGSSSNIGSNTVHWYQQLPGTAPKLLIY

SDNQRPSGVPDRFSGSKSGTSASLVISGLQSDDEADYYCAAWDDSLNGVF

GGGTKLTVL
                                               (SEQ ID NO: 44)
CAGCCTGTGCTGACTCAGCCACCCTCAGCGTCTGGGACCCCGGGCAGAG

GTCACCATCTCTTGTTCTGGAAGCAGCTCCAACATCGGAAGTAATACTG

TCCACTGGTACCAGCAACTCCCAGGAACGGCCCCCAAACTCCTCATCTAT

AGTGATAATCAGCGCCCCTCAGGGGTCCCTGACCGATTCTCTGGCTCCAA

GTCTGGCACCTCAGCCTCCCTGGTCATCAGTGGGCTCCAGTCTGACGATG

AGGCTGATTATTACTGTGCAGCATGGGATGACAGCCTGAATGGGGTGTTC

GGCGGAGGGACCAAGCTGACCGTCCTA

Light chain variable region - Ab2 germline
                                               (SEQ ID NO: 31)
QSVLTQPPSASGTPGQRVTISCSGSSSNIGSNTVHWYQQLPGTAPKLLIY

SDNQRPSGVPDRFSGSKSGTSASLAISGLQSEDEADYYCAAWDDSLNGVF

GGGTKLTVL
                                               (SEQ ID NO: 45)
CAGTCTGTGCTGACTCAGCCACCCTCAGCGTCTGGGACCCCGGGCAGAG

GTCACCATCTCTTGTTCTGGAAGCAGCTCCAACATCGGAAGTAATACTG

TCCACTGGTACCAGCAACTCCCAGGAACGGCCCCCAAACTCCTCATCTAT

AGTGATAATCAGCGCCCCTCAGGGGTCCCTGACCGATTCTCTGGCTCCAA

GTCTGGCACCTCAGCCTCCCTGGCCATCAGTGGGCTCCAGTCTGAGGATG

AGGCTGATTATTACTGTGCAGCATGGGATGACAGCCTGAATGGGGTGTTC

GGCGGAGGGACCAAGCTGACCGTCCTA
```

Light chain variable region - Ab3 parental
(SEQ ID NO: 32)
QPVLTQPPSASGTPGQRVTISCSGSTSNIGSNTVHWYQQLPGTAPKLLIY
SDDQRPSGVPDRFSGSKSGTSASLVISGLQSDDEADYYCAAWDESLNGVF
GGGTKLTVL (SEQ ID NO: 46)
CAGCCTGTGCTGACTCAGCCACCCTCAGCGTCTGGGACCCCGGGCAGAG
GGTCACCATCTCTTGTTCTGGAAGCACCTCCAACATCGGAAGTAATACTG
TCCACTGGTACCAGCAACTCCCAGGAACGGCCCCCAAACTCCTCATCTAT
AGTGATGATCAGCGCCCCTCAGGGGTCCCTGACCGATTCTCTGGCTCCAA
GTCTGGCACCTCAGCCTCCCTGGTCATCAGTGGGCTCCAGTCTGACGATG
AGGCTGATTATTACTGTGCAGCATGGGATGAGAGCCTGAATGGGGTGTTC
GGCGGAGGGACCAAGCTGACCGTCCTA Light chain variable region - Ab4 germline
(SEQ ID NO: 33)
QSVLTQPPSASGTPGQRVTISCSGSTSNIGSNTVHWYQQLPGTAPKLLIY
SDDQRPSGVPDRFSGSKSGTSASLAISGLQSEDEADYYCAAWDESLNGVF
GGGTKLTVL (SEQ ID NO: 47)
CAGTCTGTGCTGACTCAGCCACCCTCAGCGTCTGGGACCCCGGGCAGAG
GGTCACCATCTCTTGTTCTGGAAGCACCTCCAACATCGGAAGTAATACTG
TCCACTGGTACCAGCAACTCCCAGGAACGGCCCCCAAACTCCTCATCTAT
AGTGATGATCAGCGCCCCTCAGGGGTCCCTGACCGATTCTCTGGCTCCAA
GTCTGGCACCTCAGCCTCCCTGGCCATCAGTGGGCTCCAGTCTGAGGATG
AGGCTGATTATTACTGTGCAGCATGGGATGAGAGCCTGAATGGGGTGTTC
GGCGGAGGGACCAAGCTGACCGTCCTA Light chain variable region - Ab5 parental
(SEQ ID NO: 34)
QPVLTQPPSASGTPGQRVTISCSGSSSNIGGNTVHWYQQLPGTAPKLLIY
SDDQRPSGVPDRFSGSKSGTSASLVISGLQSDDEADYYCAAWDESLNGVF
GGGTKLTVL (SEQ ID NO: 48)
CAGCCTGTGCTGACTCAGCCACCCTCAGCGTCTGGGACCCCGGGCAGAG
GGTCACCATCTCTTGTTCTGGAAGCAGCTCCAACATCGGAGGAAATACTG
TCCACTGGTACCAGCAACTCCCAGGAACGGCCCCCAAACTCCTCATCTAT
AGTGATGATCAGCGCCCCTCAGGGGTCCCTGACCGATTCTCTGGCTCCAA
GTCTGGCACCTCAGCCTCCCTGGTCATCAGTGGGCTCCAGTCTGACGATG
AGGCTGATTATTACTGTGCAGCATGGGATGAGAGCCTGAATGGGGTGTTC
GGCGGAGGGACCAAGCTGACCGTCCTA Light chain variable region - Ab6 germline
(SEQ ID NO: 35)
QSVLTQPPSASGTPGQRVTISCSGSSSNIGGNTVHWYQQLPGTAPKLLIY
SDDQRPSGVPDRFSGSKSGTSASLAISGLQSEDEADYYCAAWDESLNGVF
GGGTKLTVL (SEQ ID NO: 49)
CAGTCTGTGCTGACTCAGCCACCCTCAGCGTCTGGGACCCCGGGCAGAG
GGTCACCATCTCTTGTTCTGGAAGCAGCTCCAACATCGGAGGAAATACTG
TCCACTGGTACCAGCAACTCCCAGGAACGGCCCCCAAACTCCTCATCTAT
AGTGATGATCAGCGCCCCTCAGGGGTCCCTGACCGATTCTCTGGCTCCAA
GTCTGGCACCTCAGCCTCCCTGGCCATCAGTGGGCTCCAGTCTGAGGATG
AGGCTGATTATTACTGTGCAGCATGGGATGAGAGCCTGAATGGGGTGTTC
GGCGGAGGGACCAAGCTGACCGTCCTA Ab2-Heavy Chain
(SEQ ID NO: 50)
QVQLVESGGGVVQPGRSLRLSCAASGFTFSSYGMHWVRQAPGKGLEWVAV
ISYDGSNKYYADSVKGRFTISRDNSKNTLYLQMNSLRAEDTAVYYCARDL
LVRFLEWSHYYGMDVWGQGTTVTVSSASTKGPSVFPLAPCSRSTSESTAA
LGCLVKDYFPEPVTVSWNSGALTSGVHTFPAVLQSSGLYSLSSVVTVPSS
SLGTKTYTCNVDHKPSNTKVDKRVESKYGPPCPPCPAPEFLGGPSVFLFP
PKPKDTLMISRTPEVTCVVVDVSQEDPEVQFNWYVDGVEVHNAKTKPREE
QFNSTYRVVSVLTVLHQDWLNGKEYKCKVSNKGLPSSIEKTISKAKGQPR
EPQVYTLPPSQEEMTKNQVSLTCLVKGFYPSDIAVEWESNGQPENNYKTT
PPVLDSDGSFFLYSRLTVDKSRWQEGNVFSCSVMHEALHNHYTQKSLSLS
LG Ab2-Light Chain
(SEQ ID NO: 51)
QSVLTQPPSASGTPGQRVTISCSGSSSNIGSNTVHWYQQLPGTAPKLLIY
SDNQRPSGVPDRFSGSKSGTSASLAISGLQSEDEADYYCAAWDDSLNGVF
GGGTKLTVLGQPKAAPSVTLFPPSSEELQANKATLVCLISDFYPGAVTVA
WKADSSPVKAGVETTTPSKQSNNKYAASSYLSLTPEQWKSHRSYSCQVTH
EGSTVEKTVAPTECS In some embodiments, anti-pro/latent-Myostatin antibodies of the disclosure include any antibody that includes a heavy chain variable domain of any one of SEQ ID NOs: 24-29 or a light chain variable domain of any one of SEQ ID NOs: 30-35. In some embodiments, anti-pro/latent-Myostatin antibodies of the disclosure include any antibody that includes the heavy chain variable and light chain variable pairs of SEQ ID NOs: 24 and 30; 25 and 31; 26 and 32; 27 and 33; 28 and 34; or 29 and 35).

Aspects of the disclosure provide anti-pro/latent-Myostatin antibodies having a heavy chain variable and/or a light chain variable amino acid sequence homologous to any of those described herein. In some embodiments, the anti-pro/latent-Myostatin antibody comprises a heavy chain variable sequence or a light chain variable sequence that is at least 75% (e.g., 80%, 85%, 90%, 95%, 98%, or 99%) identical to the heavy chain variable sequence of any of SEQ ID NOs: 24-29 or a light chain variable sequence of any one of SEQ ID NOs: 30-35. In some embodiments, the homologous heavy chain variable and/or a light chain variable amino acid sequences do not vary within any of the CDR sequences provided herein. For example, in some embodiments, the degree of sequence variation (e.g., 75%, 80%, 85%, 90%, 95%, 98%, or 99%) may occur within a heavy chain variable and/or a light chain variable sequence excluding any of the CDR sequences provided herein.

The "percent identity" of two amino acid sequences is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, word length=3 to obtain amino acid sequences homologous to the protein molecules of interest. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used.

Recombinant GDF-modulating antibodies of the invention may comprise or be developed using any of the VH sequences listed in Table 2. Some recombinant GDF-modulating antibodies of the invention may comprise or be developed using VH sequences that comprise at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, at least about 99.5% or at least about 99.9% sequence identity to any of the VH sequences listed in Table 2. Recombinant GDF-modulating antibodies may, in some cases, comprise VH domains presented, but with different combinations of CDRs (e.g. CDR-H1, CDR-H2 or CDR-H3).

TABLE 2

VH domains

| Clone ID | scFv sequence | SEQ ID NO |
|---|---|---|
| 14B7 | QVQLQQSGGGLVQPGGSLRLSCAASGFTFSSYAMTWVR QAPGKGLEWVSAISGGGGATYYADSVEGRFTISRDNSK NTLYLQMNSLRAEDTAIYYCASPAGHICSGGSCQYYYY GMDVWGQGTTVTVSSGS | 64 |
| 17C1 | QVQLVQSGAEVKKPGSSVKVSCKASGGTFSSYAISWVR QAPGQGLEWMGGIIPIFGTANYAQKFQGRVTITADEST STAYMELSSLRSEDTAVYYCARDRHLYRRGYSSVDGMD VWGQGTTVTVSSGS | 65 |
| 22A8 | QVQLVQSGAEVKKPGESLKISCKGSGYSFTSYWIGWVR QMPGKGLEWMGIIYPGDSDTRYSPSFQGQVTISADKSI STAYLQWSSLKASDTAMYYCARHPIGSGYDYWGQGTLV TVSSGS | 66 |
| 34H2 | QVQLVQSGGGVVRPGGSLRLSCAASGFTFDDYGMSWVR QAPGKGLEWVSGISWNSGSIGYADSVKGRFTISRDNAK NSLYLQMNSLRAEDTALYYCAKEISDTAMGFDYWGQGT LVTVSSGS | 67 |
| 59B11 | QVQLVQSGGGLVQPGGSLRLSCAASGFTFSNYWMYWV RQAPGKGLVWVSNINSDGSSTSYADSVKGRFTISRDNA KNSLYLQMNSLRDEDTAVYYCAREGYNAHYFDYWGQGT LVTVSSGS | 68 |
| 70F9 | QIQLVQSGGGVVQPGRSLRLSCAASGFTFSSYGMHWVR QAPGKGLEWVAVIWYDGSNKYYADSVKGRFTISRDNSK NTLYLQMNSLRAEDTAVYYCAKGLGYHPLFDYWGQGTL VTVSSGS | 69 |

Recombinant GDF-modulating antibodies of the invention may comprise or be developed using any of the CDR-H sequences (CDR-H1, CDR-H2 and/or CDR-H3) listed in Table 3. Some recombinant GDF-modulating antibodies of the invention may comprise or be developed using CDR-H sequences that comprise at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, at least about 99.5% or at least about 99.9% sequence identity to any of the CDR-H sequences listed in Table 3. Recombinant GDF-modulating antibodies may, in some cases, comprise CDR-H domains presented, but with different combinations of CDRs from other clones listed.

TABLE 3

CDR-H domains

| CDR Region | Clone ID | CDR amino acid sequence | SEQ ID NO |
|---|---|---|---|
| CDR-H1 | 14B7 | GFTFSSYA | 70 |
| CDR-H1 | 34H2 | GFTFDDYG | 71 |
| CDR-H2 | 14B7 | ISGGGGAT | 72 |
| CDR-H3 | 14B7 | ASPAGHICSGGSCQYYYYGMDV | 73 |
| CDR-H3 | 17C1 | ARDRHLYRRGYSSVDGMDV | 74 |
| CDR-H3 | 22A8 | ARHPIGSGYDY | 75 |
| CDR-H3 | 34H2 | AKEISDTAMGFDY | 76 |
| CDR-H1 | 59B11 | GFTFSNYW | 77 |
| CDR-H2 | 59B11 | INSDGSST | 78 |
| CDR-H3 | 59B11 | AREGYNAHYFDY | 79 |
| CDR-H3 | 70F9 | AKGLGYHPLFDY | 80 |

Recombinant GDF-modulating antibodies of the invention may comprise or be developed using any of the VL sequences listed in Table 4. Some recombinant GDF-modulating antibodies of the invention may comprise or be developed using VL sequences that comprise at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, at least about 99.5% or at least about 99.9% sequence identity to any of the VL sequences listed in Table 4. Recombinant GDF-modulating antibodies may, in some cases, comprise VL domains presented, but with different combinations of CDRs (e.g. CDR-L1, CDR-L2 or CDR-L3).

TABLE 4

VL domains

| Clone ID | VL amino acid sequence | SEQ ID NO |
|---|---|---|
| 14B7 | DIQMTQSPSFLSASVGDRVTITCRASQGI SSYLAWYQQKPGKAPKLLIYAASSLQSGV PSRFSGSGSGTDFTLTISSLQPEDFATYY CQQSYSTPLTFGGGTRVDMARTVAAPSVF | 81 |
| 17C1 | EIVMTQSPGTLSLSPGERATLSCRASQSV SSGYLAWYQQKAGQAPRLLIYGGSARAPG IPARFSGSGSGTDFTLTISSLEPEDFAVY YCQQRSIWPLTFGGGTKVEIKRTVAAPSV F | 82 |

TABLE 4-continued

VL domains

| Clone ID | VL amino acid sequence | SEQ ID NO |
|---|---|---|
| 22A8 | DIVMTQSPVSLPVTLGQPASISCRSSQSV VYRDGNTYLSWFLQRPGQSPRRLIYKVSN RDSGVPDRFSGSGSATDFTLKISRVEAED VGVYYCMQGSSWPYTFGQGTKLEIKRTVA APSVF | 83 |
| 34H2 | QSALTQPASVSGSPGQSITISCTGTSSDV GGYNYISWYQQYPGKAPKLMIYDVSKRPS GVSNRFSGSKSGNTASLTISGLQAEDEAD YYCNSYTSSRTVVFGGGTKLTVLGQPKAA PSVTLFPPSS | 84 |
| 59B11 | QSALTQPASVSGSPGQSITISCTGTSSDV GGYNYVSWYQQHPGKAPKLLIYDVTKRPS GVSNRFSGSKSGNTASLTISGLQAEDEAD YYCSSYTSSTVVFGGGTKLTVLGQPKAA PSVTLFPPSSKASGA | 85 |
| 70F9 | DIVMTQSPDSLAVSLGERATINCKSSQSV LYSSDNKNYLAWYQQKPGQPPKLLIYWAS TRESGVPDRFSGSGSGTDFTLTISSLQAE DVAVYYCQQYYSTPSFGPGTKVDIKRTVAA PSVFKASGA | 86 |

Recombinant GDF-modulating antibodies of the invention may comprise or be developed using any of the CDR-L sequences (CDR-L1, CDR-L2 and/or CDR-L3) listed in Table 5. Some recombinant GDF-modulating antibodies of the invention may comprise or be developed using CDR-L sequences that comprise at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, at least about 99.5% or at least about 99.9% sequence identity to any of the CDR-L sequences listed in Table 5. Recombinant GDF-modulating antibodies may, in some cases, comprise CDR-L domains presented, but with different combinations of CDRs from other clones listed.

TABLE 5

CDR-L domains

| CDR Region | Clone ID | CDR amino acid sequence | SEQ ID NO |
|---|---|---|---|
| CDR-L1 | 14B7 | QGISSY | 87 |
| CDR-L1 | 17C1 | QSVSSGY | 88 |
| CDR-L1 | 22A8 | QSVVYRDGNTY | 89 |
| CDR-L2 | 14B7 | AAS | 90 |
| CDR-L2 | 17C1 | GGS | 91 |
| CDR-L2 | 29H4 | SDN | 92 |
| CDR-L3 | 14B7 | QQSYSTPLT | 93 |
| CDR-L3 | 17C1 | QQRSIWPLT | 94 |
| CDR-L3 | 22A8 | MQGSSWPYT | 95 |
| CDR-L3 | 29H4 | AAWDDSLNGV | 96 |
| CDR-L3 | 34H2 | NSYTSSRTVV | 97 |
| CDR-L1 | 70F9 | QSVLYSSDNKNY | 98 |
| CDR-L2 | 59B11 | DVT | 99 |
| CDR-L3 | 59B11 | SSYTSSSTVV | 100 |
| CDR-L3 | 70F9 | QQYYSTPS | 101 |

In some embodiments, conservative mutations can be introduced into the CDRs or framework sequences at positions where the residues are not likely to be involved in interacting with pro/latent-Myostatin as determined based on the crystal structure. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g. Molecular Cloning: A Laboratory Manual, J. Sambrook, et al., eds., Second Edition, Cold Spring Harbor Laboratory Press, Cold Spring Harbor, New York, 1989, or Current Protocols in Molecular Biology, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

In some embodiments, the antibodies provided herein comprise mutations that confer desirable properties to the antibodies. For example, to avoid potential complications due to Fab-arm exchange, which is known to occur with native IgG4 mAbs, the antibodies provided herein may comprise a stabilizing 'Adair' mutation (Angal S., et al., "A single amino acid substitution abolishes the heterogeneity of chimeric mouse/human (IgG4) antibody," *Mol Immunol* 30, 105-108; 1993), where serine 228 (EU numbering; residue 241 Kabat numbering) is converted to proline resulting in an IgG1-like (CPPCP (SEQ ID NO: 58)) hinge sequence. Accordingly, any of the antibodies may include a stabilizing 'Adair' mutation or the amino acid sequence CPPCP (SEQ ID NO: 58).

Anti-pro/latent-Myostatin binding agents of this disclosure may optionally comprise antibody constant regions or parts thereof. For example, a $V_L$ domain may be attached at its C-terminal end to a light chain constant domain like Cκ or Cλ. Similarly, a $V_H$ domain or portion thereof may be attached to all or part of a heavy chain like IgA, IgD, IgE, IgG, and IgM, and any isotype subclass. Antibodies may include suitable constant regions (see, for example, Kabat et al., Sequences of Proteins of Immunological Interest, No. 91-3242, National Institutes of Health Publications, Bethesda, Md. (1991)). Therefore, antibodies within the scope of this may disclosure include $V_H$ and $V_L$ domains, or an antigen binding portion thereof, combined with any suitable constant regions.

In certain embodiments, the $V_H$ and/or $V_L$ domains may be reverted to germline sequence, e.g., the FR of these domains are mutated using conventional molecular biology techniques to match those produced by the germline cells. For example, the $V_H$ and/or $V_L$ domains may be reverted to germline sequence of IgHV3-30 (SEQ ID NO: 36) and/or IgLV1-44 (SEQ ID NO: 37), respectively. It should be appreciated that any of the $V_H$ and/or $V_L$ domains may be reverted to any suitable germline sequence. In other embodiments, the FR sequences remain diverged from the consensus germline sequences.

IgHV3-30
(SEQ ID NO: 36)
QVQLVESGGGVVQPGRSLRLSCAASGFTFSSYGMHWVRQAPGKGLEWVAV

ISYDGSNKYYADSVKGRFTISRDNSKNTLYLQMNSLRAEDTAVYYCAR

IgLV1-44
(SEQ ID NO: 37)
QSVLTQPPSASGTPGQRVTISCSGSSSNIGSNTVNWYQQLPGTAPKLLIY

SNNQRPSGVPDRFSGSKSGTSASLAISGLQSEDEADYYCAAWDDSLNG

In some embodiments, anti-pro/latent-Myostatin antibodies or antigen binding fragments may or may not include the framework region of the antibodies shown in SEQ ID NOs: 24-35. In some embodiments, anti-pro-latent-Myostatin antibodies are murine antibodies and include murine framework region sequences.

In some embodiments, an anti-pro/latent-Myostatin antibodies of the disclosure can bind to pro/latent-Myostatin with relatively high affinity, e.g., with a Kd less than $10^{-6}$M, $10^{-7}$ M, $10^{-8}$M, $10^{-9}$M, $10^{-10}$M, $10^{-11}$ M or lower. For example, anti-pro/latent-Myostatin antibodies can bind to pro/latent-Myostatin with an affinity between 5 pM and 500 nM, e.g., between 50 pM and 100 nM, e.g., between 500 pM and 50 nM. The disclosure also includes antibodies or antigen binding fragments that compete with any of the antibodies described herein for binding to pro/latent-Myostatin and that have an affinity of 50 nM or lower (e.g., 20 nM or lower, 10 nM or lower, 500 pM or lower, 50 pM or lower, or 5 pM or lower). The affinity and binding kinetics of the anti-pro/latent-Myostatin antibody can be tested using any suitable method including but not limited to biosensor technology (e.g., OCTET or BIACORE).

An antibody that "specifically binds" to a target antigen, binds to the target antigen with greater affinity, avidity, more readily, and/or with greater duration than it binds to non-target antigens. In some embodiments, antibodies are disclosed herein that specifically binds pro/latent-Myostatin. in some embodiments any of the antibodies provided herein bind at or near a tolloid cleavage site or at or near a tolloid docking site of pro/latent-Myostatin. In some embodiments, an antibody binds near a tolloid cleavage site or near a tolloid docking site if it binds within 15 or fewer amino acid residues of the tolloid cleavage site or tolloid docking site. In some embodiments, any of the antibodies provided herein bind within 1, 2, 3, 4, 5, 6, 7, 8, 9, 10, 11, 12, 13, 14 or 15 amino acid residues of a tolloid cleavage site or tolloid docking site. In some embodiments, an antibody binds at or near a tolloid cleavage site of GDF8. For example, an antibody may bind an amino acid sequence as set forth in SEQ ID NO: 62 PKAPPL-RELIDQYDVQRDDSSDGSLEDDDYHAT (SEQ ID NO: 62). In other embodiments, any of the antibodies provided herein bind at or near a proprotein convertase cleavage site or at or near a proprotein convertase docking site of pro/latent-Myostatin. In some embodiments, an antibody binds near a proprotein convertase cleavage site or near a proprotein convertase docking site if it binds within 15 or fewer amino acid residues of the proprotein convertase cleavage site or proprotein convertase docking site. In some embodiments, any of the antibodies provided herein bind within 1, 2, 3, 4, 5, 6, 7, 8, 9, 10, 11, 12, 13, 14 or 15 amino acid residues of a proprotein convertase cleavage site or proprotein convertase docking site. In some embodiments, an antibody binds at or near a proprotein convertase cleavage site of GDF8. For example, an antibody may bind an amino acid sequence as set forth in SEQ ID NO: 63. GLNPFLEVKVTDTPKRSRRDFGLDCDEHSTESRC (SEQ ID NO: 63).

In one example, the anti-pro/latent-Myostatin antibodies described herein specifically bind pro/latent-Myostatin as compared to other forms of Myostatin and/or other members of the TGFβ family of growth factors. Members of the TGFβ family of growth factors include, without limitation AMH, ARTN, BMP10, BMP15, BMP2, BMP3, BMP4, BMP5, BMP6, BMP7, BMP8A, BMP8B, GDF1, GDF10, GDF11, GDF15, GDF2, GDF3, GDF3A, GDF5, GDF6, GDF7, GDF8, GDF9, GDNF, INHA, INHBA, INHBB, INHBC, INHBE, LEFTY1, LEFTY2, NODAL, NRTN, PSPN, TGFβ1, TGFβ2, and TGFβ3 protein. Such antibodies may bind pro/latent-Myostatin at a much higher affinity as compared to other members of the TGFβ family of growth factors (e.g., at least 2-fold, 5-fold, 10-fold, 50-fold, 100-fold, 200-fold, 500-fold, or 1,000-fold higher). In some embodiments, such antibodies may bind pro/latent-Myostatin with an affinity of at least 1,000 greater as compared to other members of the TGFβ family of growth factors. In some embodiments, antibodies provided herein may bind to pro/latent-Myostatin at a much higher affinity as compared to one or more forms of GDF11 or mature Myostatin (e.g., at least 2-fold, 5-fold, 10-fold, 50-fold, 100-fold, 200-fold, 500-fold, or 1,000-fold higher). In some embodiments, antibodies provided herein may bind to pro/latent-Myostatin with an affinity of at least 1,000 greater as compared to one or more forms of GDF11 (e.g., proGDF11, latent GDF11 or mature GDF11) or mature Myostatin Alternatively, or in addition, antibodies may exhibit a much higher inhibitory activity against proteolytic cleavage of pro/latent-Myostatin (e.g., by a proprotein convertase or tolloid protease) as compared with other members of the TGFβ family, such as pro/latent GDF11 (e.g., at least 2-fold, 5-fold, 10-fold, 50-fold, 100-fold, 200-fold, 500-fold, 1,000-fold higher).

In some embodiments, antibodies bind an antigen but cannot effectively eliminate the antigen from the plasma. Thus, in some embodiments, the concentration of the antigen in the plasma may be increased by reducing the clearance of the antigen. However, in some embodiments, antibodies (e.g., sweeping antibodies) provided herein have an affinity to an antigen that is sensitive to pH. Such pH sensitive antibodies may bind to the antigen in plasma at neutral pH and dissociate from the antigen in an acidic endosome, thus reducing antibody-mediated antigen accumulation and/or promoting antigen clearance from the plasma.

Aspects of the disclosure relate to sweeping antibodies. As used herein "sweeping antibodies" refer to antibodies having both pH-sensitive antigen binding and at least a threshold level of binding to cell surface neonatal Fc receptor (FcRn) at neutral or physiological pH. In some embodiments, sweeping antibodies bind to the neonatal Fc receptor FcRn at neutral pH. For example sweeping antibodies may bind to the FcRn at a pH ranging from 7.0 to 7.6. In some embodiments, sweeping antibodies can bind to an antigen at an antigen binding site and bind to a cellular FcRn via an Fc portion of the antibody. In some embodiments, sweeping antibodies may then be internalized, releasing antigen in an acidic endosome, which may be degraded. In some embodiments, a sweeping antibody, no longer bound to the antigen, may then be released (e.g., by exocytosis) by the cell back into the serum.

In some embodiments, FcRn in the vascular endothelia (e.g., of a subject) extends the half-life of a sweeping antibody. In some embodiments, vascular endothelial cells internalize sweeping antibodies, which in some embodiments are bound to an antigen such as Myostatin (e.g., proMyostatin, latent Myostatin or primed Myostatin). In some embodiments, a sweeping antibody is recycled back into the bloodstream. In some embodiments, a sweeping antibody has an increased half-life (e.g., in the serum of a subject) as compared to its conventional counterpart. In some embodiments, a conventional counterpart of a sweeping antibody refers the antibody from which the sweeping antibody was derived (e.g., prior to engineering the Fc portion of the conventional antibody to bind FcRn with greater affinity at pH 7). In some embodiments, a sweeping antibody has a half-life in the serum of a subject that is at least 1%, 5%, 10%, 15%, 20%, 25%, 35%, 50%, 75%, 100%, 150%, 200% or 250% longer as compared to its conventional counterpart.

In some embodiments, an Fc portion of a sweeping antibody binds FcRn. In some embodiments, the Fc portion of a sweeping antibody binds to FcRn at a pH of 7.4 with a Kd ranging from $10^{-3}$ M to $10^{-8}$ M. In some embodiments, a sweeping antibody binds to FcRn at a pH of 7.4 with a Kd ranging from $10^{-3}$ M to $10^{-7}$ M, from $10^{-3}$ M to $10^{-6}$ M, from $10^{-3}$ M to $10^{-5}$ M, from $10^{-3}$ M to $10^{-4}$ M, from $10^{-4}$ M to $10^{-8}$ M, from $10^{-4}$ M to $10^{-7}$ M, from $10^{-4}$ M to $10^{-6}$ M, from $10^{-4}$ M to $10^{-5}$ M, from $10^{-5}$ M to $10^{-8}$ M, from $10^{-5}$ M to $10^{-7}$ M, from $10^{-5}$ M to $10^{-6}$ M, from $10^{-6}$ M to $10^{-8}$ M, from $10^{-6}$ M to $10^{-7}$ M, or from $10^{-7}$M to $10^{-8}$ M. In some embodiments, FcRn binds to the CH2-CH3 hinge region of a sweeping antibody. In some embodiments, FcRn binds to the same region as protein A or protein G. In some embodiments, FcRn binds to a different binding site from FcγRs. In some embodiments, the amino acid residues AA of a sweeping antibody Fc region are required for binding to FcRn. In some embodiments, the amino acid residues AA of a sweeping antibody Fc region affect binding to FcRn.

In some embodiments, any of the antibodies provided herein are engineered to bind FcRn with greater affinity. In some embodiments, any of the antibodies provided herein are engineered to bind FcRn with greater affinity at pH 7.4. In some embodiments, the affinity of sweeping antibodies to FcRn is increased to extend their pharmacokinetic (PK) properties as compared to their conventional counterparts. For example, in some embodiments, sweeping antibodies elicit less adverse reactions due to their efficacy at lower doses. In some embodiments, sweeping antibodies are administered less frequently. In some embodiments, transcytosis of sweeping antibodies to certain tissue types are increased. In some embodiments, sweeping antibodies enhance efficiency of trans-placental delivery. In some embodiments, sweeping antibodies are less costly to produce.

In some embodiments, any of the antibodies provided herein are engineered to bind FcRn with lower affinity. In some embodiments, any of the antibodies provided herein are engineered to bind FcRn with lower affinity at pH 7.4. In some embodiments, the affinity of sweeping antibodies to FcRn is decreased to shorten their pharmacokinetic (PK) properties as compared to their conventional counterparts. For example, in some embodiments, sweeping antibodies are more rapidly cleared for imaging and/or radioimmunotherapy. In some embodiments, sweeping antibodies promote clearance of endogenous pathogenic antibodies as a treatment for autoimmune diseases. In some embodiments, sweeping antibodies reduce the risk of adverse pregnancy outcome, which may be caused by trans-placental transport of material fetus-specific antibodies.

In some embodiments, sweeping antibodies have decreased affinity to an antigen at low pH as compared to a neutral or physiological pH (e.g., pH 7.4). In some embodiments, sweeping antibodies have a decreased affinity to an antigen at an acidic pH (e.g. a pH ranging from 5.5 to 6.5) as compared to a physiological pH (e.g., pH 7.4). It should be appreciated that any of the antibodies provided herein can be engineered to dissociate from the antigen depending on changes in pH (e.g., pH sensitive antibodies). In some embodiments, sweeping antibodies provided herein are engineered to bind antigen dependent on pH. In some embodiments, sweeping antibodies provided herein are engineered to bind FcRn dependent on pH. In some embodiments, sweeping antibodies provided herein are internalized by endocytosis. In some embodiments, sweeping antibodies provided here are internalized by FcRn binding. In some embodiments, endocytosed sweeping antibodies release antigen in an endosome. In some embodiments, sweeping antibodies are recycled back to the cell surface. In some embodiments, sweeping antibodies remain attached to cells. In some embodiments, endocytosed sweeping antibodies are recycled back to the plasma. It should be appreciated that the Fc portion of any of the antibodies provided herein may be engineered to have different FcRn binding activity. In some embodiments, FcRn binding activity affects the clearance time of an antigen by a sweeping antibody. In some embodiments, sweeping antibodies may be long-acting or rapid-acting sweeping antibodies.

In some embodiments, converting a conventional therapeutic antibody into a sweeping antibody reduces the efficacious dose. In some embodiments, converting a conventional therapeutic antibody into a sweeping antibody reduces the efficacious dose by at least 1%, 2%, 5%, 10%, 20%, 30%, 40%, 50%, 60%, 70%, 80%, 90%, 95%, or 99%. In some embodiments, converting a conventional therapeutic antibody into a sweeping antibody reduces the efficacious dose by at least 1.5 fold, 2 fold, 3 fold, 4 fold, 5 fold, 6 fold, 8 fold, 10 fold, 15 fold, 20 fold, 50 fold or 100 fold.

In some embodiments, selecting an appropriate dose of a sweeping antibody for therapy may be performed empirically. In some embodiments, a high dose of a sweeping antibody may saturate FcRn, resulting in antibodies which stabilize antigen in serum without being internalized. In some embodiments, a low dose of a sweeping antibody may not be therapeutically effective. In some embodiments, sweeping antibodies are administered once a day, once a week, once every two weeks, once every three weeks, once every four weeks, once every 6 weeks, once every 8 weeks, once every 10 weeks, once every 12 weeks, once every 16 weeks, once every 20 weeks, or once every 24 weeks.

In some embodiments, any of the antibodies provided herein may be modified or engineered to be sweeping antibodies. In some embodiments, any of the antibodies provided herein may be converted into a sweeping antibody using any suitable method. For example, suitable methods for making sweeping antibodies have been previously described in Igawa et al., (2013) "Engineered Monoclonal Antibody with Novel Antigen-Sweeping Activity In Vivo," *PLoS ONE* 8(5): e63236; and Igawa et al., "pH-dependent antigen-binding antibodies as a novel therapeutic modality,"

Biochimica et Biophysica Acta 1844 (2014) 1943-1950; the contents of each of which are hereby incorporated by reference. It should be appreciated, however, that the methods for making sweeping antibodies as provided herein are not meant to be limiting. Thus, additional methods for making sweeping antibodies are within the scope of this disclosure.

Some aspects of the disclosure are based on the recognition that the affinity (e.g., as expressed as Kd) of any of the anti-pro/latent-Myostatin antibodies provided herein are sensitive to changes in pH. In some embodiments, the antibodies provided herein have an increased Kd of binding to pro/latent-Myostatin at a relatively low pH (e.g., a pH ranging from 4.0-6.5) as compared to a relatively high pH (e.g., a pH ranging from 7.0-7.4). In some embodiments, the antibodies provided herein have a Kd of binding to pro/latent-Myostatin ranging from $10^{-3}$ M, $10^{-4}$ M, $10^{-5}$ M, $10^{-6}$ M, $10^{-7}$ M, $10^{-8}$ M when the pH is between 4.0 and 6.5. In some embodiments, the antibodies provided herein have a Kd of binding to pro/latent-Myostatin ranging from $10^{-6}$ M, $10^{-7}$ M, $10^{8}$ M, $10^{-9}$ M, $10^{-10}$ M, $10^{-11}$ M when the pH is between 7.0 and 7.4. In some embodiments, the antibodies provided herein have a Kd of binding to pro/latent-Myostatin that is at least 2 fold, at least 10 fold, at least 50 fold, at least 100 fold, at least 500 fold, at least 1000 fold, at least 5000 fold, or at least 10000 fold greater at a pH between 4.0 and 6.5 as compared to a pH between 7.0 and 7.4.

Polypeptides

Some aspects of the disclosure relate to a polypeptide having a sequence selected from the group consisting of SEQ ID NO: 24, SEQ ID NO: 25, SEQ ID NO: 26, SEQ ID NO: 27, SEQ ID NO: 28, and SEQ ID NO 29. In some embodiments, the polypeptide is a variable heavy chain domain. In some embodiments, the polypeptide is at least 75% (e.g., 80%, 85%, 90%, 95%, 98%, or 99%) identical to any one of the amino acid sequences set forth in SEQ ID NO: 24, SEQ ID NO: 25, SEQ ID NO: 26, SEQ ID NO: 27, SEQ ID NO: 28, or SEQ ID NO 29.

Some aspects of the disclosure relate to a polypeptide having a sequence selected from the group consisting of SEQ ID NO: 30, SEQ ID NO: 31, SEQ ID NO: 32, SEQ ID NO: 33, SEQ ID NO: 34, and SEQ ID NO 35. In some embodiments, the polypeptide is a variable light chain domain. In some embodiments, the polypeptide is at least 75% (e.g., 80%, 85%, 90%, 95%, 98%, or 99%) identical to any one of the amino acid sequences set forth in SEQ ID NO: 30, SEQ ID NO: 31, SEQ ID NO: 32, SEQ ID NO: 33, SEQ ID NO: 34, or SEQ ID NO 35.

Antibodies that Compete with Anti-Pro/Latent-Myostatin Antibodies

Aspects of the disclosure relate to antibodies that compete or cross-compete with any of the antibodies provided herein. The term "compete", as used herein with regard to an antibody, means that a first antibody binds to an epitope of a protein (e.g., latentMyostatin) in a manner sufficiently similar to the binding of a second antibody, such that the result of binding of the first antibody with its epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its epitope or ligand, whether to the same, greater, or lesser extent, the antibodies are said to "cross-compete" with each other for binding of their respective epitope(s). Both competing and cross-competing antibodies are within the scope of this disclosure. Regardless of the mechanism by which such competition or cross-competition occurs (e.g., steric hindrance, conformational change, or binding to a common epitope, or portion thereof), the skilled artisan would appreciate that such competing and/or cross-competing antibodies are encompassed and can be useful for the methods and/or compositions provided herein.

Aspects of the disclosure relate to antibodies that compete or cross-compete with any of the antibodies provided herein. In some embodiments, an antibody binds at or near the same epitope as any of the antibodies provided herein. In some embodiments, an antibody binds near an epitope if it binds within 15 or fewer amino acid residues of the epitope. In some embodiments, any of the antibodies provided herein bind within 1, 2, 3, 4, 5, 6, 7, 8, 9, 10, 11, 12, 13, 14 or 15 amino acid residues of an epitope that is bound by any of the antibodies provided herein.

In another embodiment, an antibody competes or cross-competes for binding to any of the antigens provided herein (e.g., pro/latent-Myostatin) with an equilibrium dissociation constant, Kd, between the antibody and the protein of less than $10^{-6}$ M. In other embodiments, an antibody competes or cross-competes for binding to any of the antigens provided herein with a Kd in a range from $10^{-11}$ M to $10^{-6}$ M.

Aspects of the disclosure relate to antibodies that compete for binding to pro/latent-Myostatin with any of the antibodies provided herein. In some embodiments, the antibody binds to pro/latent-Myostatin at the same epitope as any of the antibodies provided herein. For example, in some embodiments any of the antibodies provided herein bind at or near a tolloid cleavage site or at or near a tolloid docking site of pro/latent-Myostatin. In other embodiments, any of the antibodies provided herein bind at or near a proprotein convertase cleavage site or at or near a proprotein convertase docking site of pro/latent-Myostatin. In another embodiment, an antibody competes for binding to pro/latent-Myostatin with an equilibrium dissociation constant, Kd, between the antibody and pro/latent-Myostatin of less than $10^{-6}$ M. In other embodiments, the an antibody that competes with any of the antibodies provided herein binds to pro/latent-Myostatin with a Kd in ranging from $10^{-11}$ M to $10^{-6}$ M.

Any of the antibodies provided herein can be characterized using any suitable methods. For example, one method is to identify the epitope to which the antigen binds, or "epitope mapping." There are many suitable methods for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which an antibody binds. The epitope can be a linear epitope, i.e., contained in a single stretch of amino acids, or a conformational epitope formed by a three-dimensional interaction of amino acids that may not necessarily be contained in a single stretch (primary structure linear sequence). Peptides of varying lengths (e.g., at least 4-6 amino acids long) can be isolated or synthesized (e.g., recombinantly) and used for binding assays with an antibody. In another example, the epitope to which the antibody binds can be determined in a systematic screen by using overlapping peptides derived from the target antigen sequence and determining binding by the antibody. According to the gene fragment expression assays, the open reading frame encoding the target antigen is fragmented either randomly or by specific genetic constructions and the reactivity of the expressed fragments of the antigen with the antibody to be tested is determined. The gene fragments may, for example, be produced by PCR and then transcribed and translated into protein in vitro, in the presence of radioactive amino acids. The binding of the antibody to the radioactively labeled antigen fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. In an additional example, mutagenesis of an antigen binding domain, domain swapping experiments and alanine scanning mutagenesis can be performed to identify residues required, sufficient, and/or necessary for epitope binding. For example, domain swapping experiments can be performed using a mutant of a target antigen in which various fragments of the pro/latent-Myostatin polypeptide have been replaced (swapped) with sequences from a closely related, but antigenically distinct protein, such as another member of the TGFβ protein family (e.g., GDF11). By assessing binding of the antibody to the mutant pro/latent-Myostatin, the importance of the particular antigen fragment to antibody binding can be assessed.

Alternatively, competition assays can be performed using other antibodies known to bind to the same antigen to determine whether an antibody binds to the same epitope as the other antibodies. Competition assays are well known to those of skill in the art. Any of the suitable methods, e.g., the epitope mapping methods as described herein, can be applied to determine whether an anti-pro/latent-Myostatin antibody binds one or more of the specific residues/segments in pro/latent-Myostatin as described herein. Further, the interaction of the antibody with one or more of those defined residues in pro/latent-Myostatin can be determined by routine technology. For example, a crystal structure can be determined, and the distances between the residues in pro/latent-Myostatin and one or more residues in the antibody can be determined accordingly. Based on such distance, whether a specific residue in pro/latent-Myostatin interacts with one or more residues in the antibody can be determined. Further, suitable methods, such as competition assays and target mutagenesis assays can be applied to determine the preferential binding of a candidate anti-pro/latent-Myostatin antibody to pro/latent-Myostatin as compared to another target such as a mutant pro/latent-Myostatin.

Production of Antibodies that Bind Pro/Latent-Myostatin

Numerous methods may be used for obtaining antibodies, or antigen binding fragments thereof, of the disclosure. For example, antibodies can be produced using recombinant DNA methods. Monoclonal antibodies may also be produced by generation of hybridomas (see e.g., Kohler and Milstein (1975) Nature, 256: 495-499) in accordance with known methods. Hybridomas formed in this manner are then screened using standard methods, such as enzyme-linked immunosorbent assay (ELISA) and surface plasmon resonance (e.g., OCTET or BIACORE) analysis, to identify one or more hybridomas that produce an antibody that specifically binds to a specified antigen. Any form of the specified antigen may be used as the immunogen, e.g., recombinant antigen, naturally occurring forms, any variants or fragments thereof, as well as antigenic peptide thereof (e.g., any of the epitopes described herein as a linear epitope or within a scaffold as a conformational epitope). One exemplary method of making antibodies includes screening protein expression libraries that express antibodies or fragments thereof (e.g., scFv), e.g., phage or ribosome display libraries. Phage display is described, for example, in Ladner et al., U.S. Pat. No. 5,223,409; Smith (1985) Science 228:1315-1317; Clackson et al. (1991) Nature, 352: 624-628; Marks et al. (1991) J. Mol. Biol., 222: 581-597WO92/18619; WO 91/17271; WO 92/20791; WO 92/15679; WO 93/01288; WO 92/01047; WO 92/09690; and WO 90/02809.

In addition to the use of display libraries, the specified antigen (e.g., proMyostatin) can be used to immunize a non-human animal, e.g., a rodent, e.g., a mouse, hamster, or rat. In one embodiment, the non-human animal is a mouse.

In another embodiment, a monoclonal antibody is obtained from the non-human animal, and then modified, e.g., chimeric, using suitable recombinant DNA techniques. A variety of approaches for making chimeric antibodies have been described. See e.g., Morrison et al., Proc. Natl. Acad. Sci. U.S.A. 81:6851, 1985; Takeda et al., Nature 314:452, 1985, Cabilly et al., U.S. Pat. No. 4,816,567; Boss et al., U.S. Pat. No. 4,816,397; Tanaguchi et al., European Patent Publication EP171496; European Patent Publication 0173494, United Kingdom Patent GB 2177096B.

For additional antibody production techniques, see Antibodies: A Laboratory Manual, eds. Harlow et al., Cold Spring Harbor Laboratory, 1988. The present disclosure is not necessarily limited to any particular source, method of production, or other special characteristics of an antibody.

Some aspects of the present disclosure relate to host cells transformed with a polynucleotide or vector. Host cells may be a prokaryotic or eukaryotic cell. The polynucleotide or vector which is present in the host cell may either be integrated into the genome of the host cell or it may be maintained extrachromosomally. The host cell can be any prokaryotic or eukaryotic cell, such as a bacterial, insect, fungal, plant, animal or human cell. In some embodiments, fungal cells are, for example, those of the genus *Saccharomyces*, in particular those of the species *S. cerevisiae*. The term "prokaryotic" includes all bacteria which can be transformed or transfected with a DNA or RNA molecules for the expression of an antibody or the corresponding immunoglobulin chains. Prokaryotic hosts may include gram negative as well as gram positive bacteria such as, for example, *E. coli, S. typhimurium, Serratia marcescens* and *Bacillus subtilis*. The term "eukaryotic" includes yeast, higher plants, insects and vertebrate cells, e g, mammalian cells, such as NSO and CHO cells. Depending upon the host employed in a recombinant production procedure, the antibodies or immunoglobulin chains encoded by the polynucleotide may be glycosylated or may be non-glycosylated. Antibodies or the corresponding immunoglobulin chains may also include an initial methionine amino acid residue.

In some embodiments, once a vector has been incorporated into an appropriate host, the host may be maintained under conditions suitable for high level expression of the nucleotide sequences, and, as desired, the collection and purification of the immunoglobulin light chains, heavy chains, light/heavy chain dimers or intact antibodies, antigen binding fragments or other immunoglobulin forms may follow; see, Beychok, Cells of Immunoglobulin Synthesis, Academic Press, N.Y., (1979). Thus, polynucleotides or vectors are introduced into the cells which in turn produce the antibody or antigen binding fragments. Furthermore, transgenic animals, preferably mammals, comprising the aforementioned host cells may be used for the large scale production of the antibody or antibody fragments.

The transformed host cells can be grown in fermenters and cultured using any suitable techniques to achieve optimal cell growth. Once expressed, the whole antibodies, their dimers, individual light and heavy chains, other immunoglobulin forms, or antigen binding fragments, can be purified according to standard procedures of the art, including ammonium sulfate precipitation, affinity columns, column chromatography, gel electrophoresis and the like; see, Scopes, "Protein Purification", Springer Verlag, N.Y. (1982). The antibody or antigen binding fragments can then be isolated from the growth medium, cellular lysates, or cellular membrane fractions. The isolation and purification of the, e.g., microbially expressed antibodies or antigen binding fragments may be by any conventional means such as, for example, preparative chromatographic separations and immunological separations such as those involving the use of monoclonal or polyclonal antibodies directed, e.g., against the constant region of the antibody.

Aspects of the disclosure relate to a hybridoma, which provides an indefinitely prolonged source of monoclonal antibodies. As an alternative to obtaining immunoglobulins directly from the culture of hybridomas, immortalized hybridoma cells can be used as a source of rearranged heavy chain and light chain loci for subsequent expression and/or genetic manipulation. Rearranged antibody genes can be reverse transcribed from appropriate mRNAs to produce cDNA. In some embodiments, heavy chain constant region can be exchanged for that of a different isotype or eliminated altogether. The variable regions can be linked to encode single chain Fv regions. Multiple Fv regions can be linked to confer binding ability to more than one target or chimeric heavy and light chain combinations can be employed. Any appropriate method may be used for cloning of antibody variable regions and generation of recombinant antibodies.

In some embodiments, an appropriate nucleic acid that encodes variable regions of a heavy and/or light chain is obtained and inserted into an expression vectors which can be transfected into standard recombinant host cells. A variety of such host cells may be used. In some embodiments, mammalian host cells may be advantageous for efficient processing and production. Typical mammalian cell lines useful for this purpose include CHO cells, 293 cells, or NSO cells. The production of the antibody or antigen binding fragment may be undertaken by culturing a modified recombinant host under culture conditions appropriate for the growth of the host cells and the expression of the coding sequences. The antibodies or antigen binding fragments may be recovered by isolating them from the culture. The expression systems may be designed to include signal peptides so that the resulting antibodies are secreted into the medium; however, intracellular production is also possible.

The disclosure also includes a polynucleotide encoding at least a variable region of an immunoglobulin chain of the antibodies described herein. In some embodiments, the variable region encoded by the polynucleotide comprises at least one complementarity determining region (CDR) of the VH and/or VL of the variable region of the antibody produced by any one of the above described hybridomas.

Polynucleotides encoding antibody or antigen binding fragments may be, e.g., DNA, cDNA, RNA or synthetically produced DNA or RNA or a recombinantly produced chimeric nucleic acid molecule comprising any of those polynucleotides either alone or in combination. In some embodiments, a polynucleotide is part of a vector. Such vectors may comprise further genes such as marker genes which allow for the selection of the vector in a suitable host cell and under suitable conditions.

In some embodiments, a polynucleotide is operatively linked to expression control sequences allowing expression in prokaryotic or eukaryotic cells. Expression of the polynucleotide comprises transcription of the polynucleotide into a translatable mRNA. Regulatory elements ensuring expression in eukaryotic cells, preferably mammalian cells, are well known to those skilled in the art. They may include regulatory sequences that facilitate initiation of transcription and optionally poly-A signals that facilitate termination of transcription and stabilization of the transcript. Additional regulatory elements may include transcriptional as well as translational enhancers, and/or naturally associated or heterologous promoter regions. Possible regulatory elements permitting expression in prokaryotic host cells include, e.g., the PL, Lac, Trp or Tac promoter in *E. coli*, and examples of regulatory elements permitting expression in eukaryotic host cells are the AOX1 or GAL1 promoter in yeast or the CMV-promoter, SV40-promoter, RSV-promoter (Rous sarcoma virus), CMV-enhancer, SV40-enhancer or a globin intron in mammalian and other animal cells.

Beside elements which are responsible for the initiation of transcription such regulatory elements may also include transcription termination signals, such as the SV40-poly-A site or the tk-poly-A site, downstream of the polynucleotide. Furthermore, depending on the expression system employed, leader sequences capable of directing the polypeptide to a cellular compartment or secreting it into the medium may be added to the coding sequence of the polynucleotide and have been described previously. The leader sequence(s) is (are) assembled in appropriate phase with translation, initiation and termination sequences, and preferably, a leader sequence capable of directing secretion of translated protein, or a portion thereof, into, for example, the extracellular medium. Optionally, a heterologous polynucleotide sequence can be used that encode a fusion protein including a C- or N-terminal identification peptide imparting desired characteristics, e.g., stabilization or simplified purification of expressed recombinant product.

In some embodiments, polynucleotides encoding at least the variable domain of the light and/or heavy chain may encode the variable domains of both immunoglobulin chains or only one. Likewise, a polynucleotides may be under the control of the same promoter or may be separately controlled for expression. Furthermore, some aspects relate to vectors, particularly plasmids, cosmids, viruses and bacteriophages used conventionally in genetic engineering that comprise a polynucleotide encoding a variable domain of an immunoglobulin chain of an antibody or antigen binding fragment; optionally in combination with a polynucleotide that encodes the variable domain of the other immunoglobulin chain of the antibody.

In some embodiments, expression control sequences are provided as eukaryotic promoter systems in vectors capable of transforming or transfecting eukaryotic host cells, but control sequences for prokaryotic hosts may also be used. Expression vectors derived from viruses such as retroviruses, vaccinia virus, adeno-associated virus, herpes viruses, or bovine papilloma virus, may be used for delivery of the polynucleotides or vector into targeted cell population (e.g., to engineer a cell to express an antibody or antigen binding fragment). A variety of appropriate methods can be used to construct recombinant viral vectors. In some embodiments, polynucleotides and vectors can be reconstituted into liposomes for delivery to target cells. The vectors containing the polynucleotides (e.g., the heavy and/or light variable domain(s) of the immunoglobulin chains encoding sequences and expression control sequences) can be transferred into the host cell by suitable methods, which vary depending on the type of cellular host.

Modifications

Antibodies or antigen binding fragments of the disclosure may be modified with a detectable label, including, but not limited to, an enzyme, prosthetic group, fluorescent material, luminescent material, bioluminescent material, radioactive material, positron emitting metal, nonradioactive paramagnetic metal ion, and affinity label for detection and isolation of pro/latent-Myostatin. The detectable substance may be coupled or conjugated either directly to the polypeptides of the disclosure or indirectly, through an intermediate (such as, for example, a linker) using suitable techniques. Non-limiting examples of suitable enzymes include horseradish peroxidase, alkaline phosphatase, β-galactosidase, glucose oxidase, or acetylcholinesterase; non-limiting examples of suitable prosthetic group complexes include streptavidin/biotin and avidin/biotin; non-limiting examples of suitable fluorescent materials include biotin, umbelliferone, fluorescein, fluorescein isothiocyanate, rhodamine, dichlorotriazinylamine fluorescein, dansyl chloride, or phycoerythrin; an example of a luminescent material includes luminol; non-limiting examples of bioluminescent materials include luciferase, luciferin, and aequorin; and examples of suitable radioactive material include a radioactive metal ion, e.g., alpha-emitters or other radioisotopes such as, for example, iodine ($^{131}$I, $^{125}$I, $^{123}$I, $^{121}$I) carbon ($^{14}$C), sulfur ($^{35}$S), tritium ($^{3}$H), indium ($^{115}$mIn, $^{113}$mIn, $^{112}$In, $^{111}$In), and technetium ($^{99}$Tc, $^{99}$mTc), thallium gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, Lu, $^{159}$Gd, $^{149}$Pm, $^{140}$La, $^{175}$Yb, $^{166}$Ho, $^{90}$Y, $^{47}$Cc, $^{86}$R, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, and tin ($^{113}$Sn, $^{117}$Sn). The detectable substance may be coupled or conjugated either directly to the anti-pro/latent-Myostatin antibodies of the disclosure or indirectly, through an intermediate (such as, for example, a linker) using suitable techniques. Anti-pro/latent-Myostatin antibodies conjugated to a detectable substance may be used for diagnostic assays as described herein.

Pharmaceutical Compositions

One or more of the anti-pro/latent-Myostatin antibodies can be mixed with a pharmaceutically acceptable carrier (excipient), including buffer, to form a pharmaceutical composition for use in alleviating a disease or disorder that is associated with myopathy. "Acceptable" means that the carrier must be compatible with the active ingredient of the composition (and preferably, capable of stabilizing the active ingredient) and not deleterious to the subject to be treated. Examples of pharmaceutically acceptable excipients (carriers), including buffers, would be apparent to the skilled artisan and have been described previously. See, e.g., Remington: The Science and Practice of Pharmacy 20th Ed. (2000) Lippincott Williams and Wilkins, Ed. K. E. Hoover. In one example, a pharmaceutical composition described herein contains more than one anti-pro/latent-Myostatin antibodies that recognize different epitopes/residues of the target antigen.

The pharmaceutical compositions to be used in the present methods can comprise pharmaceutically acceptable carriers, excipients, or stabilizers in the form of lyophilized formulations or aqueous solutions. (Remington: The Science and Practice of Pharmacy 20th Ed. (2000) Lippincott Williams and Wilkins, Ed. K. E. Hoover). Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Pharmaceutically acceptable excipients are further described herein.

In some examples, the pharmaceutical composition described herein comprises liposomes containing the anti-pro/latent-Myostatin antibody, which can be prepared by any suitable method, such as described in Epstein, et al., Proc. Natl. Acad. Sci. USA 82:3688 (1985); Hwang, et al., Proc. Natl. Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The anti-pro/latent-Myostatin antibody may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Exemplary techniques have been described previously, see, e.g., Remington, The Science and Practice of Pharmacy 20th Ed. Mack Publishing (2000).

In other examples, the pharmaceutical composition described herein can be formulated in sustained-release format. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The pharmaceutical compositions to be used for in vivo administration must be sterile. This is readily accomplished by, for example, filtration through sterile filtration membranes. Therapeutic antibody compositions are generally placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient can be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the present disclosure, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 mg to about 500 mg of the active ingredient of the present disclosure. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate. Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%.

The emulsion compositions can be those prepared by mixing an anti-proMyostatin antibody with Intralipid™ or the components thereof (soybean oil, egg phospholipids, glycerol and water).

Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect. Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner Use of Anti-Pro/Latent-Myostatin Antibodies for Treating Diseases/Disorders The anti-pro/latent-Myostatin antibodies described herein are effective in treating a disease or disorder associated with myopathy. As used herein, the term "myopathy" refers to a muscular disease in which the muscle fibers do not function properly, typically resulting in muscular weakness. Myopathies include muscular diseases that are neuromuscular or musculoskeletal in nature. In some embodiments, the myopathy is an inherited myopathy. Inherited myopathies include, without limitation, dystrophies, myotonias, congenital myopathies (e.g., nemaline myopathy, multi/mini-core myopathy, and centronuclear myopathy), mitochondrial myopathies, familial periodic myopathies, inflammatory myopathies and metabolic myopathies (e.g., glycogen storage diseases and lipid storage disorder). In some embodiments, the myopathy is an acquired myopathy. Acquired myopathies include, without limitation, external substance induced myopathy (e.g., drug-induced myopathy and glucocorticoid myopathy, alcoholic myopathy, and myopathy due to other toxic agents), myositis (e.g., dermatomyositis, polymositis and inclusion body myositis), myositis ossificans, rhabdomyolysis, and myoglobinurias, and disuse atrophy. In some embodiments, the myopathy is disuse atrophy, which may be caused by bone fracture (e.g. a hip fracture) or by nerve injury (e.g., spinal cord injury (SCI)). In some embodiments the myopathy is related to a disease or disorder such as amyotrophic lateral sclerosis (ALS), spinal muscular atrophy (SMA), cachexia syndromes due to renal failure, AIDS, cardiac conditions and/or cancer. In some embodiments the myopathy is related to ageing.

An aspect of the disclosure includes a method of treating a subject having a myopathy, the method comprising administering to the subject an effective amount of an antibody described above. In some embodiments, the myopathy is a primary myopathy. In another embodiment, the primary myopathy comprises disuse atrophy. In other embodiments, the disuse atrophy is associated with hip fracture, elective joint replacement, critical care myopathy, spinal cord injury or stroke. In some embodiments, the myopathy is a secondary myopathy, in which muscle loss is secondary to a disease pathology. In other embodiments, the secondary myopathy comprises denervation, genetic muscle weakness or cachexia. In another embodiment, the secondary myopathy is a denervation associated with amyotrophic lateral sclerosis or spinal muscular atrophy. In some embodiments, the secondary myopathy is a genetic muscle weakness associated with a muscular dystrophy. In other embodiments, the secondary myopathy is a cachexia associated with renal failure, AIDS, a cardiac condition, cancer or aging.

Another aspect of the disclosure includes a method of treating a subject having a disease or condition related to aging. Exemplary diseases and conditions related to ageing include, without limitation, sarcopenia (age-related muscle loss), frailty, and androgen deficiency.

Another aspect of the disclosure includes a method of treating a subject having a disease or condition related to disuse atrophy/trauma. Exemplary diseases and conditions related to disuse atrophy/trauma include, without limitation, muscle weakness related to time spent in an intensive care unit (ICU), hip/joint replacement, hip fracture, stroke, bed rest, SCI, rotator cuff injury, knee replacement, bone fracture, and burns.

Another aspect of the disclosure includes a method of treating a subject having a neurodegenerative disease or condition. Exemplary neurodegenerative diseases or conditions include, without limitation, spinal muscular atrophy and amyotrophic lateral sclerosis (ALS).

Another aspect of the disclosure includes a method of treating a subject having a disease or condition related to Cachexia. Exemplary diseases and conditions related to cachexia include, without limitation, cancer, chronic heart failure, acquired immune deficiency syndrome (AIDS), chronic obstructive pulmonary disease (COPD), and chronic kidney disease (CKD).

Another aspect of the disclosure includes a method of treating a subject having a disease or condition related to rare diseases. Exemplary rare diseases and conditions include, without limitation, osteogenesis imperfecta, sporadic Inclusion body myositis, and acute lymphoblastic leukemia.

Another aspect of the disclosure includes a method of treating a subject having a disease or condition related to a metabolic disorder and/or body composition. In some embodiments, the disease or condition is obesity (e.g., severe obesity), Prader-Willi, type II diabetes, or anorexia. However, additional diseases or conditions related to metabolic disorders and/or body composition would be apparent to the skilled artisan and are within the scope of this disclosure.

Another aspect of the disclosure includes a method of treating a subject having a disease or condition related to congenital myopathies. Exemplary congenital myopathies include, without limitation, X-linked myotubular myopathy, autosomal dominant centronuclear myopathy, autosomal recessive centronuclear myopathy, nemaline myopathy, and congenital fiber-type disproportion myopathy.

Another aspect of the disclosure includes a method of treating a subject having a disease or condition related to muscular dystrophies. Exemplary muscular dystrophies include, without limitation, Duchenne's, Becker's, facioscapulohumeral (FSH), and Limb-Girdle muscular dystrophies.

Another aspect of the disclosure includes a method of treating a subject having a urogynecological related disease or condition, glottic disorders (stenosis), extraocular myopathy, carpel tunnel, Guillain-Barré, or osteosarcoma.

To practice the method disclosed herein, an effective amount of the pharmaceutical composition described above can be administered to a subject (e.g., a human) in need of the treatment via a suitable route, such as intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes. Commercially available nebulizers for liquid formulations, including jet nebulizers and ultrasonic nebulizers are useful for administration. Liquid formulations can be directly nebulized and lyophilized powder can be nebulized after reconstitution. Alternatively, anti-pro/latent-Myostatin antibodies can be aerosolized using a fluorocarbon formulation and a metered dose inhaler, or inhaled as a lyophilized and milled powder.

The subject to be treated by the methods described herein can be a mammal, more preferably a human Mammals include, but are not limited to, farm animals, sport animals, pets, primates, horses, dogs, cats, mice and rats. A human subject who needs the treatment may be a human patient having, at risk for, or suspected of having a disease/disorder associated with myopathy, such as those noted above. A subject having a pro/latent-Myostatin-associated disease or disorder can be identified by routine medical examination, e.g., laboratory tests, organ functional tests, CT scans, or ultrasounds. A subject suspected of having any of such disease/disorder might show one or more symptoms of the disease/disorder. A subject at risk for the disease/disorder can be a subject having one or more of the risk factors for that disease/disorder.

"An effective amount" as used herein refers to the amount of each active agent required to confer therapeutic effect on the subject, either alone or in combination with one or more other active agents. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of a disease/disorder associated with myopathy. Alternatively, sustained continuous release formulations of an anti-pro/latent-Myostatin may be appropriate. Various formulations and devices for achieving sustained release would be apparent to the skilled artisan and are within the scope of this disclosure.

In one example, dosages for an anti-pro/latent-Myostatin antibody as described herein may be determined empirically in individuals who have been given one or more administration(s) of the antibody. Individuals are given incremental dosages of the antagonist. To assess efficacy of the antagonist, an indicator of the disease/disorder can be followed.

Generally, for administration of any of the antibodies described herein, an initial candidate dosage can be about 2 mg/kg. For the purpose of the present disclosure, a typical daily dosage might range from about any of 0.1 μg/kg to 3 μg/kg to 30 μg/kg to 300 μg/kg to 3 mg/kg, to 30 mg/kg to 100 mg/kg or more, depending on the factors mentioned above. For repeated administrations over several days or longer, depending on the condition, the treatment is sustained until a desired suppression of symptoms occurs or until sufficient therapeutic levels are achieved to alleviate a disease or disorder associated with pro/latent-Myostatin, or a symptom thereof. An exemplary dosing regimen comprises administering an initial dose of about 2 mg/kg, followed by a weekly maintenance dose of about 1 mg/kg of the antibody, or followed by a maintenance dose of about 1 mg/kg every other week. However, other dosage regimens may be useful, depending on the pattern of pharmacokinetic decay that the practitioner wishes to achieve. For example, dosing from one-four times a week is contemplated. In some embodiments, dosing ranging from about 3 µg/mg to about 2 mg/kg (such as about 3 µg/mg, about 10 µg/mg, about 30 µg/mg, about 100 µg/mg, about 300 µg/mg, about 1 mg/kg, and about 2 mg/kg) may be used. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the antibody used) can vary over time.

In some embodiments, for an adult patient of normal weight, doses ranging from about 0.3 to 5.00 mg/kg may be administered. The particular dosage regimen, e.g., dose, timing and repetition, will depend on the particular individual and that individual's medical history, as well as the properties of the individual agents (such as the half-life of the agent, and other relevant considerations).

For the purpose of the present disclosure, the appropriate dosage of an anti-pro/latent-Myostatin antibody will depend on the specific antibody (or compositions thereof) employed, the type and severity of the disease/disorder, whether the antibody is administered for preventive or therapeutic purposes, previous therapy, the patient's clinical history and response to the antagonist, and the discretion of the attending physician. In some embodiments, a clinician will administer an anti-pro/latent-Myostatin antibody, until a dosage is reached that achieves the desired result. Administration of an anti-pro/latent-Myostatin antibody can be continuous or intermittent, depending, for example, upon the recipient's physiological condition, whether the purpose of the administration is therapeutic or prophylactic, and other factors known to skilled practitioners. The administration of an anti-pro/latent-Myostatin antibody may be essentially continuous over a preselected period of time or may be in a series of spaced dose, e.g., either before, during, or after developing a disease or disorder associated with pro/latent-Myostatin.

As used herein, the term "treating" refers to the application or administration of a composition including one or more active agents to a subject, who has a disease/disorder associated with myopathy, a symptom of the disease/disorder, or a predisposition toward the disease/disorder, with the purpose to cure, heal, alleviate, relieve, alter, remedy, ameliorate, improve, or affect the disorder, the symptom of the disease, or the predisposition toward the disease/disorder.

Alleviating a disease/disorder associated with pro/latent-Myostatin includes delaying the development or progression of the disease, or reducing disease severity. Alleviating the disease does not necessarily require curative results. As used therein, "delaying" the development of a disease/disorder associated with pro/latent-Myostatin means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques. However, development also refers to progression that may be undetectable. For purpose of this disclosure, development or progression refers to the biological course of the symptoms. "Development" includes occurrence, recurrence, and onset. As used herein "onset" or "occurrence" of a disease/disorder associated with myopathy includes initial onset and/or recurrence.

In some embodiments, the anti-pro/latent-Myostatin antibody described herein is administered to a subject in need of the treatment at an amount sufficient to inhibit the proteolytic activation of pro/latent-Myostatin to active Myostatin by at least 20% (e.g., 30%, 40%, 50%, 60%, 70%, 80%, 90% or greater) in vivo. In other embodiments, an antibody is administered in an amount effective in reducing the pro/latent-Myostatin or latent Myostatin level by at least 20% (e.g., 30%, 40%, 50%, 60%, 70%, 80%, 90% or greater).

Conventional methods, known to those of ordinary skill in the art of medicine, can be used to administer the pharmaceutical composition to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the antibody and a physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of the antibody, can be dissolved and administered in a pharmaceutical excipient such as Water-for-Injection, 0.9% saline, or 5% glucose solution.

In one embodiment, an anti-pro/latent-Myostatin antibody is administered via site-specific or targeted local delivery techniques. Examples of site-specific or targeted local delivery techniques include various implantable depot sources of the anti-pro/latent-Myostatin antibody or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568.

Targeted delivery of therapeutic compositions containing a polynucleotide, or expression vector can also be used. Receptor-mediated DNA delivery techniques are described in, for example, Findeis et al., Trends Biotechnol. (1993) 11:202; Chiou et al., Gene Therapeutics: Methods And Applications Of Direct Gene Transfer (J. A. Wolff, ed.) (1994); Wu et al., J. Biol. Chem. (1988) 263:621; Wu et al., J. Biol. Chem. (1994) 269:542; Zenke et al., Proc. Natl. Acad. Sci. USA (1990) 87:3655; Wu et al., J. Biol. Chem. (1991) 266:338.

Therapeutic compositions containing a polynucleotide (e.g., those encoding the anti-pro/latent-Myostatin antibodies described herein) are administered in a range of about 100 ng to about 200 mg of DNA for local administration in a gene therapy protocol. In some embodiments, concentration ranges of about 500 ng to about 50 mg, about 1 µg to about 2 mg, about 5 µg to about 500 µg, and about 20 µg to about 100 µg of DNA or more can also be used during a gene therapy protocol.

The therapeutic polynucleotides and polypeptides described herein can be delivered using gene delivery vehicles. The gene delivery vehicle can be of viral or non-viral origin (see generally, Jolly, Cancer Gene Therapy (1994) 1:51; Kimura, Human Gene Therapy (1994) 5:845; Connelly, Human Gene Therapy (1995) 1:185; and Kaplitt, Nature Genetics (1994) 6:148). Expression of such coding sequences can be induced using endogenous mammalian or heterologous promoters and/or enhancers. Expression of the coding sequence can be either constitutive or regulated.

Suitable viral-based vectors for delivery of a desired polynucleotide (e.g., encoding an antibody disclosed herein) and expression in a desired cell are within the scope of this disclosure. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther. (1992) 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther. (1992) 3:147); ligand-linked DNA (see, e.g., Wu, J. Biol. Chem. (1989) 264: 16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP Patent No. 0524968. Additional approaches are described in Philip, Mol. Cell. Biol. (1994) 14:2411, and in Woffendin, Proc. Natl. Acad. Sci. (1994) 91:1581.

The particular dosage regimen, e.g., dose, timing and repetition, used in the method described herein will depend on the particular subject and that subject's medical history.

In some embodiments, more than one anti-pro/latent-Myostatin antibodies, or a combination of an anti-pro/latent-Myostatin antibody and another suitable therapeutic agent, may be administered to a subject in need of the treatment. The antagonist can be the same type or different from each other. The anti-pro/latent-Myostatin antibody can also be used in conjunction with other agents that serve to enhance and/or complement the effectiveness of the agents.

Treatment efficacy for a disease/disorder associated with myopathy can be assessed using any suitable methods. For example, treatment efficacy for a disease/disorder associated with myopathy can be assessed by evaluating muscle weakness (e.g., assessing the pattern and severity of weakness), electromyography, evaluating blood chemistries (e.g., assessing electrolytes, assessing endocrine causes, measuring creatinine kinase level, determining erythrocyte sedimentation rate and performing antinuclear antibody assays), and evaluating biopsies (e.g., by histologic, histochemical, electron microscopic, biochemical, and genetic analysis).

Kits for Use in Alleviating Diseases/Disorders Associated with Myopathy

The present disclosure also provides kits for use in alleviating diseases/disorders associated with myopathy. Such kits can include one or more containers comprising an anti-pro/latent-Myostatin antibody, e.g., any of those described herein.

In some embodiments, the kit can comprise instructions for use in accordance with any of the methods described herein. The included instructions can comprise a description of administration of the anti-pro/latent-Myostatin antibody to treat, delay the onset, or alleviate a target disease as those described herein. The kit may further comprise a description of selecting an individual suitable for treatment based on identifying whether that individual has the target disease. In still other embodiments, the instructions comprise a description of administering an antibody to an individual at risk of the target disease.

The instructions relating to the use of an anti-pro/latent-Myostatin antibody generally include information as to dosage, dosing schedule, and route of administration for the intended treatment. The containers may be unit doses, bulk packages (e.g., multi-dose packages) or sub-unit doses. Instructions supplied in the kits of the disclosure are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, delaying the onset and/or alleviating a disease or disorder associated with myopathy. Instructions may be provided for practicing any of the methods described herein.

The kits of this disclosure are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an anti-pro/latent-Myostatin antibody as those described herein.

Kits may optionally provide additional components such as buffers and interpretive information. Normally, the kit comprises a container and a label or package insert(s) on or associated with the container. In some embodiments, the disclosure provides articles of manufacture comprising contents of the kits described above.

Assays for Detecting Pro/Latent-Myostatin

In some embodiments, methods and compositions provided herein relate to a method for detecting pro/latent-Myostatin in a sample obtained from a subject. As used herein, a "subject" refers to an individual organism, for example, an individual mammal. In some embodiments, the subject is a human. In some embodiments, the subject is a non-human mammal. In some embodiments, the subject is a non-human primate. In some embodiments, the subject is a rodent. In some embodiments, the subject is a sheep, a goat, a cattle, a cat, or a dog. In some embodiments, the subject is a vertebrate, an amphibian, a reptile, a fish, an insect, a fly, or a nematode. In some embodiments, the subject is a research animal. In some embodiments, the subject is genetically engineered, e.g., a genetically engineered non-human subject. The subject may be of either sex and at any stage of development. In some embodiments, the subject is a patient or a healthy volunteer.

In some embodiments, a method for detecting a pro/latent-Myostatin in a sample obtained from a subject involves (a) contacting the sample with the anti-pro/latent-Myostatin antibody under conditions suitable for binding of the antibody to the antigen, if the antigen is present in the sample, thereby forming binding complexes; and (b) determining the level of the antibody or antigen binding fragment bound to the antigen (e.g., determining the level of the binding complexes).

As used herein a binding complex refers to a biomolecular complex of antibody (including antigen binding fragments) bound to antigen (e.g., pro/latent-Myostatin protein). Binding complexes may comprise antibodies with a single specificity or two or more antibodies or antigen binding fragments with different specificities. In one embodiment, a binding complex comprises two or more antibodies recognizing different antigenic sites on the same antigen. In some instances, an antibody may be bound to an antigen, having bound to it other biomolecules such as RNA, DNA, polysaccharides or proteins. In one embodiment, a binding complex comprises two or more antibodies recognizing different antigens. In some embodiments, an antibody in a binding complex (e.g., an immobilized antibody bound to antigen), may itself by bound, as an antigen, to an antibody (e.g., a detectably labeled antibody). Thus, binding complexes may, in some instances, comprise multiple antigens and multiple antibodies or antigen binding fragments.

Antigens present in binding complexes may or may not be in their native in situ conformation. In some embodiments, a binding complex is formed between an antibody and a purified protein antigen, or isolated proteins comprising antigen, in which the antigen is not in its native in situ conformation. In some embodiments, a binding complex is formed between an antibody and a purified protein antigen, in which the antigen is not in its native in situ conformation and is immobilized on solid support (e.g., a PVDF membrane). In some embodiments, a binding complex is formed with an antibody and, for example, a cell surface protein that is present in situ in a native confirmation (e.g., on the surface of a cell).

Antibodies in binding complexes may or may not be detectably labeled. In some embodiments, binding complexes comprise detectably labeled antibodies and non-labeled antibodies. In some embodiments, binding complexes comprise detectably labeled antigen. In some embodiments, antibodies, in binding complexes, are immobilized to one or more solid supports. In some embodiments, antigens, in binding complexes, are immobilized to one or more solid supports. Exemplary solid supports are disclosed herein and will be apparent to one of ordinary skill in the art. The foregoing examples of binding complexes are not intended to be limiting. Other examples of binding complexes will be apparent to one or ordinary skill in the art.

In any of the detection, diagnosis, and monitoring methods, the antibody, (including antigen binding fragments) or antigen may be conjugated to a solid support surface, either directly or indirectly. Methods for conjugation to solid supports are standard and can be accomplished via covalent and non-covalent interactions. Non-limiting examples of conjugation methods include: adsorption, cross-linking, protein A/G-antibody interactions, and streptavidin-biotin interactions. Other methods of conjugation will be readily apparent to one of ordinary skill in the art.

In some aspects, detection, diagnosis, and monitoring methods include comparing the level of the antibody (including antigen binding fragments) bound to the antigen (e.g., pro/latent-Myostatin) to one or more reference standards. The reference standard may be, for example, the level of a corresponding pro/latent-Myostatin in a subject that does or does not have a pro/latent-Myostatin. In one embodiment, the reference standard is the level of pro/latent-Myostatin detected in a sample that does not contain pro/latent-Myostatin (e.g., a background level). Alternatively, a background level can be determined from a sample that contains a particular pro/latent-Myostatin, by contacting the sample with non-specific antibodies (e.g., antibodies obtained from non-immune serum). Then again, the reference standard may be the level of pro/latent-Myostatin detected in a sample that does contain pro/latent-Myostatin (e.g., a positive control). In some cases, the reference standard may be a series of levels associated with varying concentrations of pro/latent-Myostatin in a sample and useful for quantifying the concentration of pro/latent-Myostatin in the test sample. The foregoing examples of reference standards are not limiting and other suitable reference standard will be readily apparent to one of ordinary skill in the art. In some embodiments, the level of the antibody bound to pro/latent-Myostatin is compared to the level of mature Myostatin. In some instances the level of pro/latent-Myostatin is compared to mature Myostatin to determine the ratio of inactive to active Myostatin in the sample.

The level of pro/latent-Myostatin may be measured, as provided herein, from a biological sample. A biological sample refers to any biological material which may be obtained from a subject or cell. For example, a biological sample may be whole blood, plasma, serum, saliva, cerebrospinal fluid, urine, cells (or cell lysate) or tissue (e.g., normal tissue or tumor tissue). In some embodiments, a biological sample is a fluid sample. In some embodiments, a biological sample is a solid tissue sample. For example, a tissue sample may include, without limitation skeletal muscle, cardiac muscle, adipose tissue as well as tissue from other organs. In some embodiments, a biological sample is a biopsy sample. In some embodiments, a solid tissue sample may be made into a fluid sample using routine methods in the art.

A biological sample may also include one or more cells of a cell line. In some embodiments, a cell line includes human cells, primate cells (e.g., vero cells), rat cells (e.g., GH3 cells, OC23 cells) or mouse cells (e.g., MC3T3 cells). There are a variety of human cell lines, including, without limitation, human embryonic kidney (HEK) cells, HeLa cells, cancer cells from the National Cancer Institute's 60 cancer cell lines (NCI60), DU145 (prostate cancer) cells, Lncap (prostate cancer) cells, MCF-7 (breast cancer) cells, MDA-MB-438 (breast cancer) cells, PC3 (prostate cancer) cells, T47D (breast cancer) cells, THP-1 (acute myeloid leukemia) cells, U87 (glioblastoma) cells, SHSY5Y human neuroblastoma cells (cloned from a myeloma) and Saos-2 (bone cancer) cells.

A further embodiment relates to a method for monitoring a disease, a condition, or any treatment thereof (e.g., myopathy or myopathy treatment) in a subject having, or at risk of having, the disease or condition comprising: (a) obtaining a biological sample from the subject, (b) determining the level of a pro/latent-Myostatin in the biological sample using an antibody that detects pro/latent-Myostatin, and (c) repeating steps (a) and (b) on one or more occasions. Myostatin has been used as a biomarker for muscle atrophy, however, the currently available commercial methods and reagents (e.g., antibodies used in ELISAs and Western Blots) are either not specific for Myostatin, detect only mature myostatin or do not detect myostatin at all. Thus, provided herein are methods and reagents (e.g., antibodies) for detecting pro/latent-Myostatin in the context of diseases and/or conditions (e.g., muscle atrophy) for diagnostic purposes. As one example, the level of pro/latent-Myostatin may be measured in a subject, or biological sample therefrom, to detect or monitor the progression of a disease or condition. As another example, the level of pro/latent-Myostatin may be measured in a subject, or biological sample therefrom, to monitor the response to a treatment for a disease or condition. It should be appreciated that the level of pro/latent-Myostatin may be monitored over any suitable period of time, which may differ depending on the disease or condition, the subject has or any treatment regimen that the subject may be subject to.

Another embodiment relates to a diagnostic composition comprising any one of the above described antibodies, antigen binding fragments, polynucleotides, vectors or cells and optionally suitable means for detection. The antibodies are, for example, suited for use in immunoassays in which they can be utilized in liquid phase or bound to a solid phase carrier. Examples of immunoassays which can utilize the antibody are competitive and non-competitive immunoassays in either a direct or indirect format. Examples of such immunoassays are the Enzyme Linked Immunoassay (ELISA), radioimmunoassay (RIA), the sandwich (immunometric assay), flow cytometry, the western blot assay, immunoprecipitation assays, immunohistochemistry, immuno-microscopy, lateral flow immuno-chromatographic assays, and proteomics arrays. The antigens and antibodies can be bound to many different solid supports (e.g., carriers, membrane, columns, proteomics array, etc.). Examples of solid support materials include glass, polystyrene, polyvinyl chloride, polyvinylidene difluoride, polypropylene, polyethylene, polycarbonate, dextran, nylon, amyloses, natural and modified celluloses, such as nitrocellulose, polyacrylamides, agaroses, and magnetite. The nature of the support can be either fixed or suspended in a solution (e.g., beads).

By a further embodiment, antibodies (including antigen binding fragments) provided herein may also be used in a method for evaluating pro/latent-Myostatin expression in a subject by obtaining a biological sample from the subject which may be a tissue sample, a blood sample or any other appropriate body fluid sample. The procedure may comprise contacting the blood sample (whole blood, serum, plasma), a tissue sample, or protein sample isolated therefrom, with an antibody, under conditions enabling the formation of binding complexes between antibody and antigen. The level of such binding complexes may then be determined by any suitable method. In some embodiments, the biological sample is contacted with the antibody under conditions suitable for binding of the antibody to a pro/latent-Myostatin protein, if the antigen is present in the sample, and formation of binding complexes consisting of antibody, bound to the antigen. This contacting step is typically performed in a reaction chamber, such as a tube, plate well, membrane bath, cell culture dish, microscope slide, and the like. In some embodiments, an antibody is immobilized on a solid support. In some embodiments, the antigen is immobilized on a solid support. In some embodiments, the solid support is the surface of a the reaction chamber. In some embodiments, the solid support is of a polymeric membrane (e.g., nitrocellulose strip, Polyvinylidene Difluoride (PVDF) membrane, etc.). Other appropriate solid supports may be used.

In some embodiments, an antibody is immobilized on the solid support prior to contacting with the antigen. In other embodiments, immobilization of the antibody is performed after formation of binding complexes. In still other embodiments, antigen is immobilized on a solid support prior to formation of binding complexes. A detection reagent is added to the reaction chamber to detect immobilized binding complexes. In some embodiments, the detection reagent comprises a detectably labeled secondary antibody directed against the antigen. In some embodiments, the primary antibody is itself detectable labeled, and is thereby the detection reagent.

In one aspect, detection methods comprise the steps of immobilizing antibodies to a solid support; applying a sample (e.g., a biological sample or isolated protein sample) to the solid support under conditions that permit binding of antigen to the antibodies, if present in the sample; removing the excess sample from the solid support; applying detectably labeled antibodies under conditions that permit binding of the detectably labeled antibodies to the antigen-bound immobilized antibodies; washing the solid support and assaying for the presence of label on the solid support.

In some embodiments, the antigen is immobilized on the solid support, such as a PVDF membrane, prior to contacting with the antibody in a reaction chamber (e.g., a membrane bath). A detection reagent is added to the reaction chamber to detect immobilized binding complexes. In some embodiments, the detection reagent comprises a detectably labeled secondary antibody directed against the antigen. In some embodiments, the detection reagent comprises a detectably labeled secondary antibody directed against the primary antibody. As disclosed herein, the detectable label may be, for example, a radioisotope, a fluorophore, a luminescent molecule, an enzyme, a biotin-moiety, an epitope tag, or a dye molecule. In some embodiments, the primary antibody is itself detectable labeled, and is thereby the detection reagent. Suitable detectable labels are described herein, and will be readily apparent to one of ordinary skill in the art.

Accordingly, diagnostic kits, suitable for home or clinical use (point of care service), are provided that comprise (a)

detectably labeled and/or non-labeled antibodies, as antigen binding reagents (e.g., pro/latent-Myostatin binding reagents); (b) a detection reagent; and, optionally, (c) complete instructions for using the reagents to detect antigens in a sample. In some embodiments, the diagnostic kit includes the antibody, and/or pro/latent-Myostatin immobilized on a solid support. Any of the solid supports described herein are suitable for incorporation in the diagnostic kits. In a preferred embodiment, the solid support is the surface of a reaction chamber of a plate well. Typically, the plate well is in a multi-well plate having a number of wells selected from: 6, 12, 24, 96, 384, and 1536, but it is not so limited. In other embodiments, the diagnostic kits provide a detectably labeled antibody. Diagnostic kits are not limited to these embodiments and other variations in kit composition will be readily apparent to one of ordinary skill in the art.

The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1: Generation and Selection of Antibodies

Antibody Summary

Ab2 is a fully human anti-pro/latent-Myostatin monoclonal antibody of the IgG4/lambda isotype that binds to human pro- and latent-myostatin with high affinity (Kd=3420 pM by ForteBio BLI). The antibody is capable of inhibiting the proteolytic activation of pro/latent-Myostatin with IC50 values in the 0.5 micromolar range (which is at or near the limit of the assay). The theoretical molecular weight of the polypeptide is 144,736 Da and its theoretical pI is 6.7. Affinity optimization using antibody display was performed to identify higher affinity variants Ab4 and Ab6. The affinity optimized variants are similarly constructed on the human IgG4/lambda isotype frameworks.

TABLE 6

Biochemical properties of candidate anti-Pro/latent-Myostatin antibodies

| Antibody | Affinity (Octet) pM | Theoretical MW (Da) *aglycosylated | Calculated pI |
|---|---|---|---|
| Ab1 | 4760 | 144809.8 | 6.9 |
| Ab2 | 3420 | 144735.6 | 6.7 |
| Ab4 | 472 | 144661.7 | 6.7 |
| Ab6 | 331 | 144629.5 | 6.7 |

Platform and Identification of Parental Antibody

The parental Ab1 antibody was identified via selection of a naïve phage display library using pro- and latent-myostatin as the primary antigens for selection. Phage selection and initial screening were performed using a library displaying conventional scFv in a format similar to that described by McCafferty et al. (McCafferty et. al., 1990). Each round of selection consisted of pre-clearing (for removal of nonspecific phage antibodies), incubation with antigen, washing, elution and amplification. Selections were performed via multiple rounds using both solid phase (biotinylated antigens coated on immunotubes) and solution phase (biotinylated antigens, captured using streptavidin coated beads) panning strategies.

In total, 10,000 individual scFv clones were screened for binding to pro- or latent-myostatin through two separate campaigns. The first program utilized pro/latent-Myostatin as an antigen, while a second campaign used latent Myostatin as an antigen. DNA for scFv clones of interest were sequenced and 216 unique clones were identified. Positive binding scFv clones were counter-screened for binding to proGDF11 as well as to a panel of unrelated proteins to confirm specificity for pro/latent-Myostatin. From the panel of unique scFv clones, 101 (of 134 GDF8 specific clones) were converted to full length IgG (IgG1 isotype) for additional characterization.

Full-length IgG antibodies were further characterized by ELISA for binding to the human and murine pro- and latent-forms of myostatin and GDF11. Antibodies were also screened for binding to the Myostatin prodomain, proTGFβ (human and murine), the mature growth factor of Myostatin, the GDF11 mature growth factor, the Activin A growth factor, and proActivin A. Lead antibodies were selected based on their cross-reactivity with pro- and latent human and murine Myostatin, with no interactions with GDF11, Activin, or TGFβ proteins.

Two forms of epitope binning were employed. First, chimeric constructs which swapped portions of the prodomains of Myostatin and GDF11 were designed and produced. These chimeric proteins were assayed for interaction with screening antibodies by ELISA. Epitope binning was carried out using a ForteBio BLI instrument, in which the biotinylated pro/latent-Myostatin antibody was immobilized on a streptavidin coated biosensor chip, and cross-blocking of antibodies was evaluated by sensor response. These epitope binning experiments, along with data from the ELISA binding experiments, allowed for the segregation of our functionally active lead antibodies (see below) into three distinct epitope groups (see Table 7).

TABLE 7

Ranking of five anti-pro/latent-Myostatin IgG1 antibodies

| Clone ID | proGDF8 Kd (μM) (octet) | Human proGDF8 IC50$^2$ (μM) Reporter assay | Murine proGDF8 IC50$^2$ (μM) Reporter assay | % body weight increase in 6 weeks 25 mg/kg/week | % lean mass increase in 4 weeks 20 mg/kg/week | Epitope bin |
|---|---|---|---|---|---|---|
| Ab1 | 11.5 | 0.996 | 1.46 | 14.58* | 14.1* | 1 |
| Ab7 | 28 | 0.983 | 1.68 | 12.42* | ND | 1 |
| Ab8 | 0.5 | 6.037 | 139$^1$ | 10.33* | 7.4 | 2 |

TABLE 7-continued

Ranking of five anti-pro/latent-Myostatin IgG1 antibodies

| Clone ID | proGDF8 Kd (μM) (octet) | Human proGDF8 IC50$^2$ (μM) Reporter assay | Murine proGDF8 IC50$^2$ (μM) Reporter assay | % body weight increase in 6 weeks 25 mg/kg/week | % lean mass increase in 4 weeks 20 mg/kg/week | Epitope bin |
|---|---|---|---|---|---|---|
| Ab9 | 22 | 12.16 | 19.86 | 7.44 | ND | 3 |
| Ab10 | 0.3 | 0.772 | ND | ND | 14.3* | 1 |

*Statistical significance by one-way ANOVA with Dunnett.
Ab8 does not bind latent myostatin, only pro/Myostatin. Murine pro/latent-Myostatin preparations have ~40% latent material which reduces the apparent efficacy in functional assays.
ND: Not determined.

In order to evaluate the ability of antibodies to bind and inhibit the activation of pro/latent-Myostatin, a number of biochemical and cellular assays were established. Binding kinetics to pro- and latent-Myostatin was measured by ForteBio Octet, in which the biotinylated substrate protein was immobilized on streptavidin coated sensor chips. The equilibrium dissociation constants of candidates from screening are shown in Table 7.

To measure the ability of the IgGs to inhibit Myostatin signaling, a Myostatin activation assay was developed. Conditioned medium from cells overexpressing either mT112 (the tolloid protease require for Myostatin activation) or Furin (the proprotein convertase which cleaves the mature growth factor from the prodomain) were produced. Following pre-incubation with the test antibody, pro/latent-Myostatin or latent Myostatin was incubated with either a mixture of mT112 and Furin conditioned media (proMyostatin) or mT112 conditioned media (latent Myostatin). Following an overnight proteolysis reaction, the release of mature growth factor was measured using a CAGA-based reporter assay in 293T cells. Antibodies were further validated by dose response, in the same assay, the results of which are shown in Table 7.

Five parental antibodies (Table 7) demonstrated consistently potent selectivity and activity in all of the above assays and were further chosen for further characterization in vivo (discussed in Example 2). For consistency, the binding and activity of these antibodies towards pro/latent-Myostatin is summarized, as Ab8 does not recognize latent myostatin.

Figure 3A:
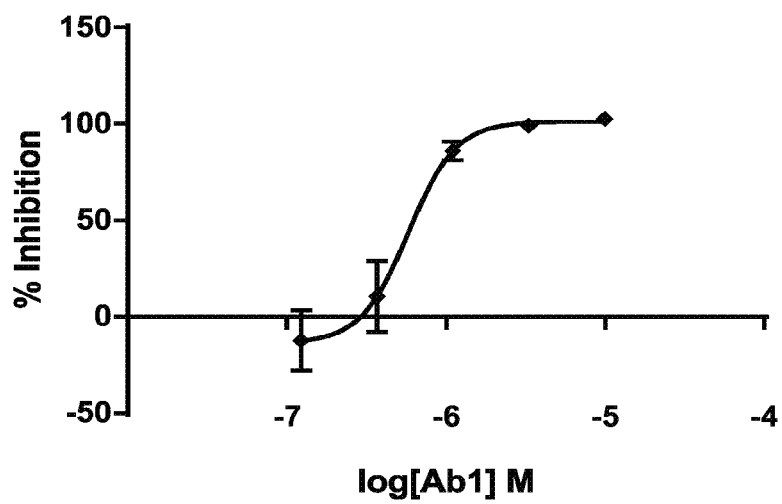
FIGS. 3A-3C show that Ab1 blocks cleavage of proMyostatin by members of the tolloid family of proteases. Pro-Myostatin samples, preincubated with increasing amounts of Ab1, were analyzed in a myostatin activation assay. Following analysis of myostatin release by reporter assay (FIG.
Figure 3B:
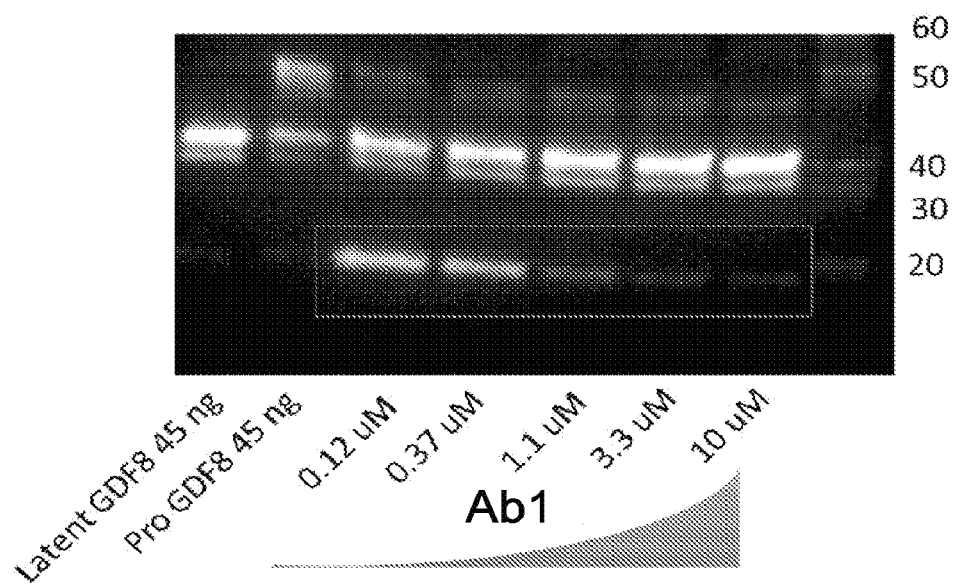
Figure 3C:
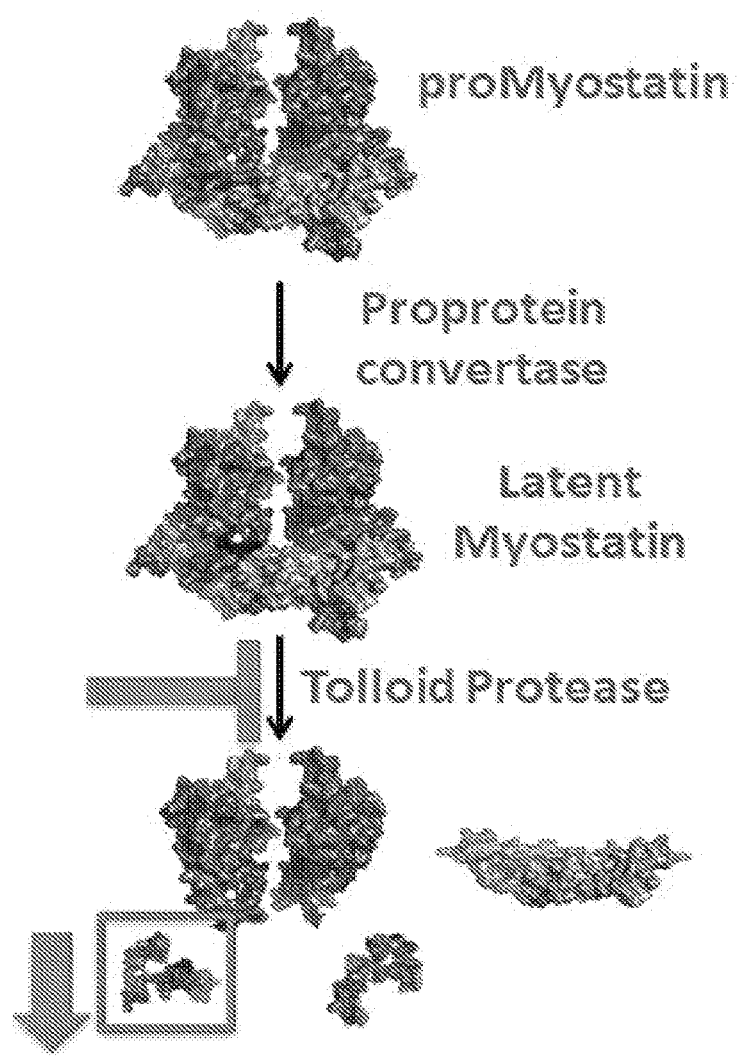

To determine the mechanism of action of antibody candidates, samples were analyzed by western blotting using a polyclonal antibody raised against the prodomain of myostatin, as shown in FIG. 3. This allowed for tracking of a fragment (boxed) of the myostatin prodomain which is generated after mT112 cleavage. A dose-dependent decrease was seen in the generation of this fragment as the concentration of Ab1 is increased. This experiment indicates that the antibodies in epitope bin 1 act by blocking the cleavage of pro- and latent-myostatin by the tolloid family of proteases.

Based on the in vitro and in vivo activity of the active anti-pro/latent-Myostatin antibodies, Ab1 was selected as the lead for further optimization, including affinity maturation, germlining and manufacturability analysis.

Optimization of Ab1

The Ab1 antibody was selected for further optimization. The affinity for pro/latent-Myostatin was optimized using yeast display. Additionally, the sequence of Ab1 was germlined to reduce the potential immunogenicity liability of non-germline amino acid positions within the human variable regions frameworks.

Affinity Optimization of Ab1 by Yeast Display

Figure 23A:
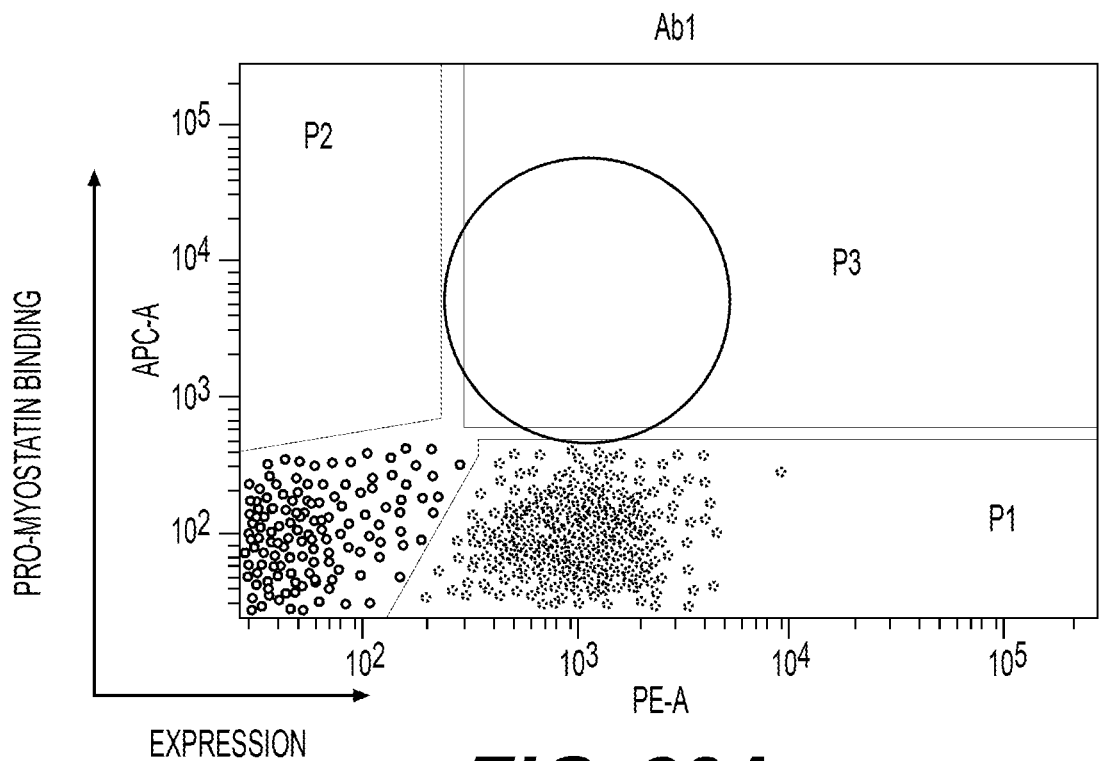
FIGS. 23A-23C show the optimization of Ab1. Optimized candidates which bind specifically to proMyostatin were chosen, resulting in dozens of clones with increased affinity. FACS was performed to show the increased binding of the yeast clones (FIG. 23B) compared to Ab1 (FIG. 23A).
Figure 23B:
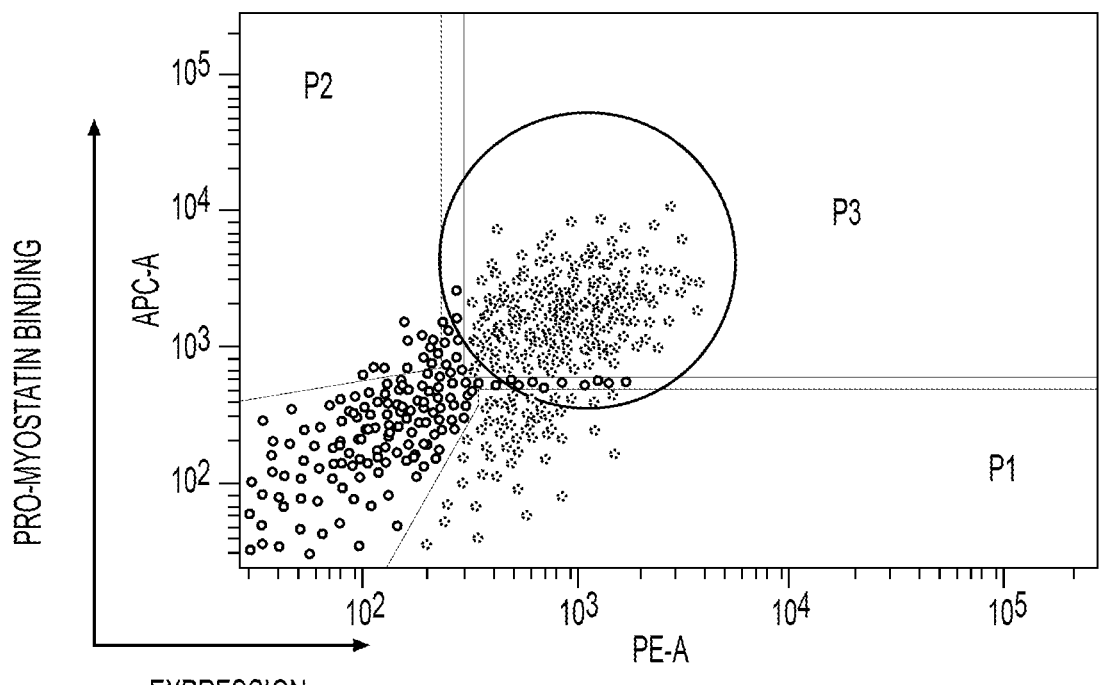
Figure 23C:
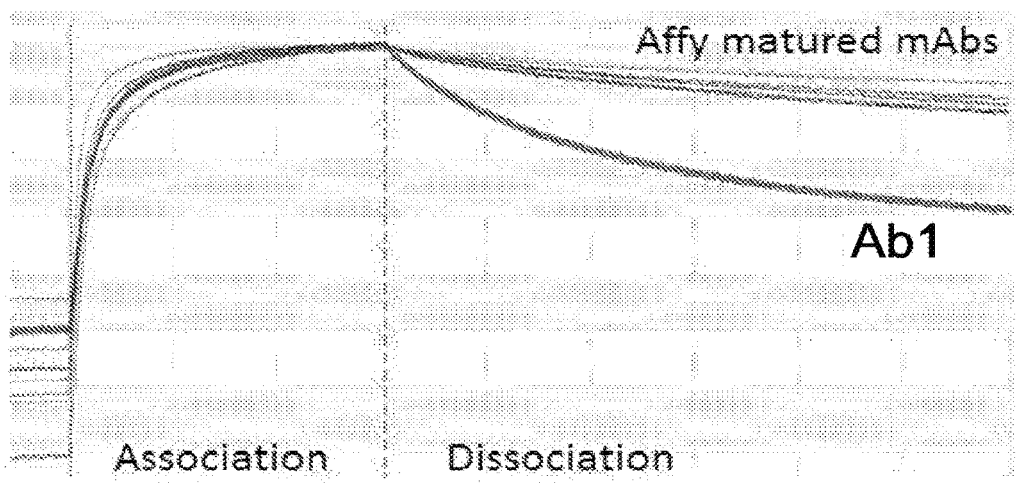

The Ab1 parental antibody was optimized for binding to pro/latent-Myostatin using an scFv display approach based in yeast. Briefly, three different scFv libraries were created to introduce point mutations to selected CDR positions based on the amino acid frequency observed in natural human antibody repertoires using antibody deep sequencing corresponding to the human frameworks utilized by Ab1. Each library contained scFv based on the Ab1 sequence with single point mutations introduced in each CDR such that each variant of the resulting heavy chain or light chain would have three total substitutions, one in each CDR. The three libraries were used for FACS-based sorting and selection to identify pools of clones with higher binding affinity for pro/latent-Myostatin (FIG. 23). Direct binding of yeast expressed scFv clones was used to select antibodies for conversion to full length IgG expressed in mammalian cell culture.

Many of the higher affinity scFv clones identified in the yeast campaign contained a substitution at position 28 of the heavy chain. For some clones, substitution of threonine to asparagine resulted in the incorporation of a non-canonical N-glycosylation motif within CDRH1. As N-glycosylation within the variable region of an antibody may be undesirable, any clone which contained a glycosylation motif was further substituted to contain alanine at this position.

The binding kinetics to pro- and latent-Myostatin were then assessed by octet for each of the affinity optimized constructs and compared to that of the parental Ab1 (discussed in Example 2). All of the clones showed significantly increased binding affinity for Myostatin, and two, Ab3 and Ab5, were selected based on the selective binding profile over GDF11.

Primary Sequence and Backbone of Anti-Pro/Latent-Myostatin Antibodies

The sequence alignment of the variable regions of parental Ab1 with its affinity optimized variants is shown below. Complementarity-determining regions (CDRs) are defined using the Kabat (underlined) and IMGT nomenclature (bold). Substitutions from parental Ab1 are shown in lower case red (below and FIG. 24A-24B).

A. Heavy Chain Variable Region

```
              FRAMEWORK 1              CDR1         FRAMEWORK 2
Ab1 paren-    QIQLVQSGGGVVQPGRSLRLSCAASGFTFSSYGMHWVRQAPGKGLEWVA
tal
Ab3           QIQLVQSGGGVVQPGRSLRLSCAASGFaFSSYGMHWVRQAPGKGLEWVA
Ab5           QIQLVQSGGGVVQPGRSLRLSCAASGFaFSSYGMHWVRQAPGKGLEWVA CDR2                FRAMEWORK 3
Ab1 paren-    VISYDGSNKYYADSVKGRFTISRDNSKNTLYLQMNSLRAEDTAVYYCAR
tal
Ab3           VISYDGSiKYYADSVKGRFTISRDNSKNTLYLQMNSLRAEDTAVYYCAR
Ab5           VISYDGnNKYYADSVKGRFTISRDNSKNTLYLQMNSLRAEDTAVYYCAR CDR3          FRAMEWORK 4
Ab1 paren-    DLLVRFLEWSHYYGMDVWGQGTTVTVSS  (SEQ ID NO: 24)
tal
Ab3           DLLVRFLEWSHkYGMDVWGQGTTVTVSS  (SEQ ID NO: 26)
Ab5           DLLVRFLEWSHkYGMDVWGQGTTVTVSS  (SEQ ID NO: 28)
```

B. Light Chain Variable Region

```
              FRAMEWORK 1          CDR1          FRW2
Ab1 paren-    QPVLTQPPSASGTPGQRVTISCSGSSSNIGSNTVHWYQQLPGTAPKLLIY
tal
Ab3           QPVLTQPPSASGTPGQRVTISCSGStSNIGSNTVHWYQQLPGTAPKLLIY
Ab5           QPVLTQPPSASGTPGQRVTISCSGSSSNIGgNTVHWYQQLPGTAPKLLIY CDR2         FRAMEWORK 3
Ab1 paren-    SDNQRPSGVPDRFSGSKSGTSASLVISGLQSDDEADYYC
tal
Ab3           SDdQRPSGVPDRFSGSKSGTSASLVISGLQSDDEADYYC
Ab5           SDdQRPSGVPDRFSGSKSGTSASLVISGLQSDDEADYYC CDR3         FRAMEWORK 4
Ab1 paren-    AAWDDSLNGVFGGGTKLTVL  (SEQ ID NO: 30)
tal
Ab3           AAWDeSLNGVFGGGTKLTVL  (SEQ ID NO: 32)
Ab5           AAWDeSLNGVFGGGTKLTVL  (SEQ ID NO: 34)
```

Antibody Engineering and Rationale for Isotype Selection

In some embodiments, an antibody useful for myostatin blockade will lack effector function. Thus for the humanized construct, an IgG4-Fc region was selected. Antibodies of the IgG4 isotype poorly bind complement C1q and therefore do not significantly activate complement. These antibodies also bind weakly to Fcγ receptors, leading to inefficient or absent antibody-dependent cell-mediated cytotoxicity (ADCC).

To avoid potential complication due to Fab-arm exchange, which is known to occur with native IgG4 mAbs, Ab1 and its variants were engineered with the stabilizing 'Adair' mutation (Angal, 1993), where serine 228 (EU numbering; residue 241 Kabat numbering) is converted to proline resulting in an IgG1-like (CPPCP (SEQ ID NO: 58)) hinge sequence. This engineered Fc-sequence is used in the production of the approved antibodies Keytruda, Mylotarg and Tysabri, as well as in a number of current late-stage clinical candidate mAbs.

Germlining and Immunogenicity Risk Assessment

The Ab1 parental antibody and its variants are fully human IgG4 (S228P), lambda antibodies derived from phage display. The Fc portion of the antibody contains a single stabilizing mutation to prevent Fab arm exchange (described above). The IgG4 Fc is not expected to have measurable binding to Fc gamma receptors (see Example 2).

Figure 22:
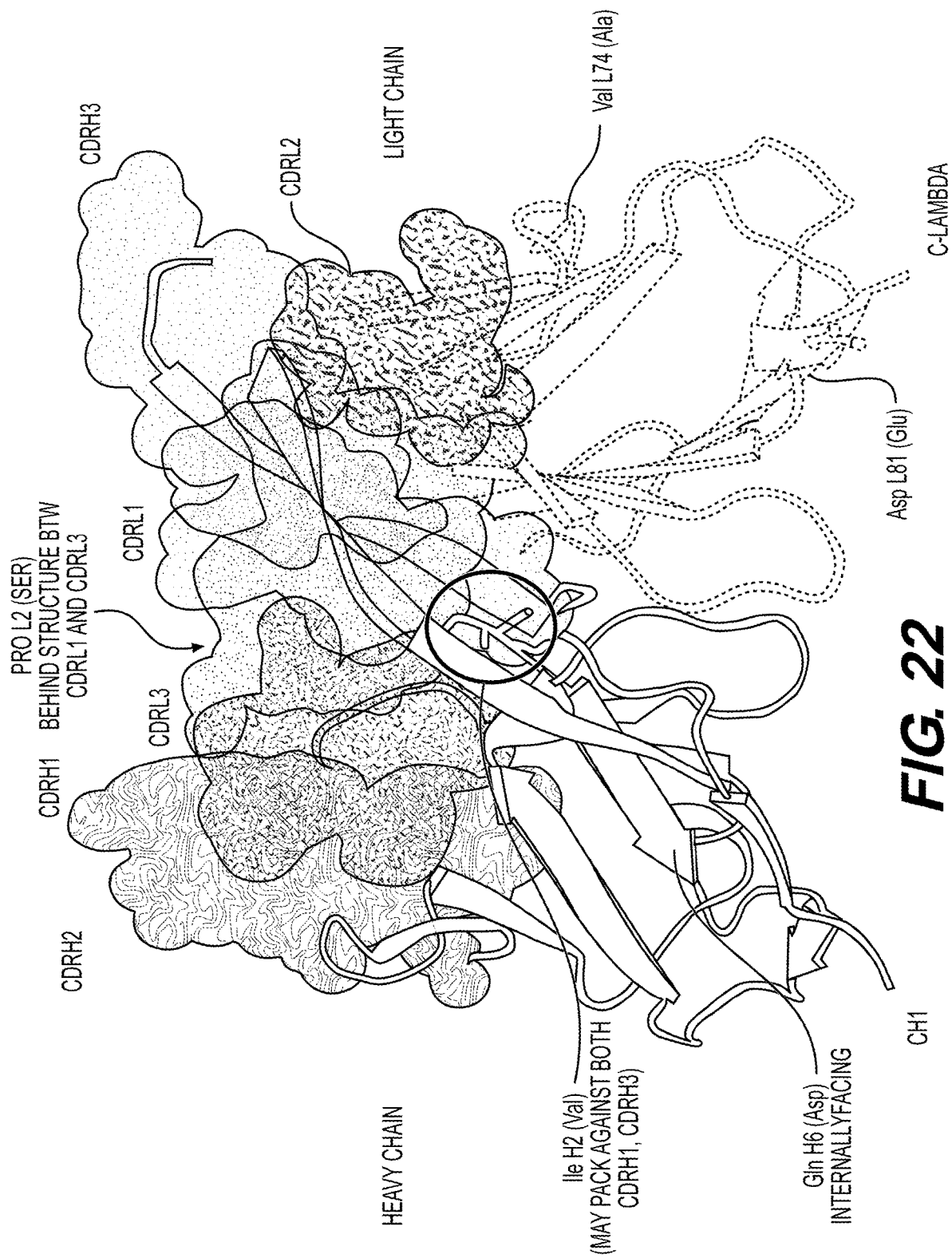
FIG. 22 is a schematic showing the reduced immunogenicity risk by germlining 24H4 (WT) contains 5 non-germline amino acids within framework regions, as indicated in the schematic.

The variable framework regions of Ab1 as isolated from the fully human naïve phage library contains five non-germline amino acids (see below and FIG. 22). Complementarity determining regions (CDRs) are defined using the Kabat nomenclature and are underlined. Non-germline residues are shown in lower case.

A. Heavy Chain Variable Region

```
         <------------FR1------------><CDR><-----FR2----><-----CDR2------>
Ab1      QIQLVQSGGGVVQPGRSLRLSCAASGFTFSSYGMHWVRQAPGKGLEWVAVISYDGSNKYYADSVKG
IgHV3-30.v...e.............................................................

<--------------FR3---------------><------CDR3-----><---FR4--->
Ab1      RFTISRDNSKNTLYLQMNSLRAEDTAVYYCARDLLVRFLEWSHYYGMDVWGQGTTVTVSS
(SEQ ID NO: 24)

IgHV3-30 ............................... (SEQ ID NO: 36)

JH6                                       ................ (SEQ ID NO: 59)
```

B. Light Chain Variable Region

```
         <---------FR1--------><----CDR1---><-----FR2-----><CDR2->
Ab1      QPVLTQPPSASGTPGQRVTISCSGSSSNIGSNTVHWYQQLPGTAPKLLIYSDNQRPS
```

```
IgLV1-44   .s........n........n.....

<--------------FR3-------------><--CDR3--><---FR4-->
Ab1         GVPDRFSGSKSGTSASLVISGLQSDDEADYYCAAWDDSLNGVFGGGTKLTVL
(SEQ ID NO: 30)

IgLV1-44   .................a......e....... (SEQ ID NO: 60)

JL1/2/3                                        ........... (SEQ ID NO: 61)
```

To mitigate the potential for immunogenicity, additional variants of Ab1 molecules were created which substitute the non-germline framework residues to their corresponding germline amino acids. In some embodiments, the substitution pertaining to Ab1 may be similarly applied to Ab3 and Ab4, or any antibody disclosed herein for which germlining is appropriate.

A sequence alignment of variable regions of Ab1 with its affinity optimized variants is shown below. A.) heavy chain, B.) light chain. Complementarity determining regions (CDRs) are defined using the Kabat (underlined) and IMGT nomenclature (bold). Framework regions substitutions present in parental Ab1 are shown in lower case.

Three of the five substitutions were found to be away from CDR regions and therefore have no impact on binding. A Proline at position 2 of the light chain packs against CDRL3 and substitution to germline Serine actually improves binding to pro/latent-Myostatin by stabilizing the CDR conformation.

The overall antibody is greater than 99% human (calculated as 100% minus the % non-germline AA excluding CDRH3). There are no chemical conjugations. The heavy chain CDRH2 sequence contains a potential isomerization liability (Asp-Gly) which is also present in the germline IgHV3-30 sequence.

```
                A. Heavy Chain Variable Region

FRAMEWORK 1           CDR1       FRAMEWORK 2
IgHV3-30   QVQLVESGGGVVQPGRSLRLSCAASGFTFSSYGMHWVRQAPGKGLEWVA
Ab1        QiQLVqSGGGVVQPGRSLRLSCAASGFTFSSYGMHWVRQAPGKGLEWVA
Ab2        QVQLVESGGGVVQPGRSLRLSCAASGFTFSSYGMHWVRQAPGKGLEWVA
Ab4        QVQLVESGGGVVQPGRSLRLSCAASGFAFSSYGMHWVRQAPGKGLEWVA
Ab6        QVQLVESGGGVVQPGRSLRLSCAASGFAFSSYGMHWVRQAPGKGLEWVA

CDR2            FRAMEWORK 3
IgHV3-30   VISYDGSNKYYADSVKGRFTISRDNSKNTLYLQMNSLRAEDTAVYYCAR
Ab1        VISYDGSNKYYADSVKGRFTISRDNSKNTLYLQMNSLRAEDTAVYYCAR
Ab2        VISYDGSNKYYADSVKGRFTISRDNSKNTLYLQMNSLRAEDTAVYYCAR
Ab4        VISYDGSIKYYADSVKGRFTISRDNSKNTLYLQMNSLRAEDTAVYYCAR
Ab6        VISYDGNNKYYADSVKGRFTISRDNSKNTLYLQMNSLRAEDTAVYYCAR

CDR3            FRAMEWORK 4
IgHV3-30   --------------------------- (SEQ ID NO: 36)
Ab1        DLLVRFLEWSHYYGMDVWGQGTTVTVSS (SEQ ID NO: 24)
Ab2        DLLVRFLEWSHYYGMDVWGQGTTVTVSS (SEQ ID NO: 25)
Ab4        DLLVRFLEWSHKYGMDVWGQGTTVTVSS (SEQ ID NO: 27)
Ab6        DLLVRFLEWSHKYGMDVWGQGTTVTVSS (SEQ ID NO: 29)

B. Light Chain Variable Region

FRAMEWORK 1           CDR1       FRW2
IgLV1-44   QSVLTQPPSASGTPGQRVTISCSGSSSNIGSNTVNWYQQLPGTAPKLLIY
Ab1        QpVLTQPPSASGTPGQRVTISCSGSSSNIGSNTVHWYQQLPGTAPKLLIY
Ab2        QSVLTQPPSASGTPGQRVTISCSGSSSNIGSNTVHWYQQLPGTAPKLLIY
Ab4        QSVLTQPPSASGTPGQRVTISCSGSTSNIGSNTVHWYQQLPGTAPKLLIY
Ab6        QSVLTQPPSASGTPGQRVTISCSGSSSNIGGNTVHWYQQLPGTAPKLLIY

CDR2        FRAMEWORK 3
IgLV1-44   SNNQRPSGVPDRFSGSKSGTSASLAISGLQSEDEADYYC
Ab1        SDNQRPSGVPDRFSGSKSGTSASLViSGLQSdDEADYYC
Ab2        SDNQRPSGVPDRFSGSKSGTSASLAISGLQSEDEADYYC
Ab4        SDDQRPSGVPDRFSGSKSGTSASLAISGLQSEDEADYYC
Ab6        SDDQRPSGVPDRFSGSKSGTSASLAISGLQSEDEADYYC

CDR3      FRAMEWORK 4
IgLV1-44   -------------------- (SEQ ID NO: 60)
Ab1        AAWDDSLNGVFGGGTKLTVL (SEQ ID NO: 30)
Ab2        AAWDDSLNGVFGGGTKLTVL (SEQ ID NO: 31)
Ab4        AAWDESLNGVFGGGTKLTVL (SEQ ID NO: 33)
Ab6        AAWDESLNGVFGGGTKLTVL (SEQ ID NO: 35)
```

Example 2: Pharmacological Characterization

In Vitro Pharmacological Assays

A total of 24 optimized Ab1 variants were expressed and purified as IgG4 and assayed for improved binding and functional activity. The changes to these molecules included germlining mutations to the parental variable region, along with mutations in the CDRs which conferred increased binding to pro/latent-Myostatin in the affinity maturation screen (see Example 1).

The Ab1 variants were screened in several different ELISA-based assays, in which the binding to the proMyostatin and latent Myostatin proteins (human, murine, and cynomolgus) was re-assessed, along with a large screen of negative control proteins to verify that non-specific binding was not introduced as a result of the affinity maturation. Negative controls included GDF11 proteins (proGDF11, latent GDF11 and mature GDF11), TGFβ proteins, and Activin proteins (proActivin). Additionally, the antibodies were assessed for polyspecificity (which can lead to rapid clearance) in a screen similar to that published previously (Hotzel et al., 2012). Any antibodies with significant interactions to negative control proteins, or with baculovirus particles in the polyspecificity screen were not considered further as candidates for a development program.

The 24 optimized variants of Ab1 were also assessed in the proMyostatin activation assay to determine their functional efficacy, and EC50 values from dose response curves were compared to the parental Ab1 antibody. Most antibodies had equivalent or improved EC50 values, with a few displaying reduced efficacy in this assay. Those with reduced efficacy in the activity assay were excluded from further analysis.

Three variants of Ab1 with improved binding to pro- and latent myostatin while retaining specificity for pro- and latent myostatin were identified. Binding and activity data for these three variants and the parental Ab1 molecule are summarized in Tables 8-11, sequences are shown in Example 1.

TABLE 8

Binding characteristics of antibodies to human/cynomolgus/mouse proMyostatin to parental Ab1 IgG4.

| | Ab1 | | | |
|---|---|---|---|---|
| | Activity Assay - 293T cells | Kinetics Analysis - Fortebio Octet | | |
| | EC50 (µM) | kon(1/Ms) | kdis(1/s) | Kd (M) |
| Human | 0.274 | 4.18E+05 | 1.99E-03 | 4.76E-09 |
| Cynomolgus | 0.5842 | 3.05E+05 | 1.75E-03 | 5.75E-09 |
| Mouse | 0.8386 | 2.37E+05 | 2.62E-03 | 1.10E-08 |

TABLE 9

Binding characteristics of antibodies to human/cynomolgus/mouse proMyostatin to Ab1 IgG4 with the correct germline residues replaced (Ab2) for non-germlined residues.

| | Ab2 | | | |
|---|---|---|---|---|
| | Activity Assay - 293T cells | Kinetics Analysis - Fortebio Octet | | |
| | EC50 (µM) | kon(1/Ms) | kdis(1/s) | Kd (M) |
| Human | 0.248 | 4.57E+05 | 1.56E-03 | 3.42E-09 |
| Cynomolgus | 0.6168 | 2.78E+05 | 1.41E-03 | 5.08E-09 |
| Mouse | 0.7138 | 2.35E+05 | 1.97E-03 | 8.39E-09 |

TABLE 10

Binding characteristics of antibodies to human/cynomolgus/mouse proMyostatin to Ab3 IgG4 containing the corrected germline residues (Ab4).

| | Ab4 | | | |
|---|---|---|---|---|
| | Activity Assay - 293T cells | Kinetics Analysis - Fortebio Octet | | |
| | EC50 (µM) | kon(1/Ms) | kdis(1/s) | Kd (M) |
| Human | 0.179 | 4.98E+05 | 2.35E-04 | 4.72E-10 |
| Cynomolgus | 0.4451 | 3.01E+05 | 2.34E-04 | 7.76E-10 |
| Mouse | 0.4466 | 2.53E+05 | 2.72E-04 | 1.08E-09 |

TABLE 11

Binding characteristics of antibodies to human/cynomolgus/mouse proMyostatin to Ab5 IgG4 containing the corrected germline residues (Ab6).

| | Ab6 | | | |
|---|---|---|---|---|
| | Activity Assay - 293T cells | Kinetics Analysis - Fortebio Octet | | |
| | EC50 (nM) | kon(1/Ms) | kdis(1/s) | Kd (M) |
| Human | 0.151 | 5.27E+05 | 2.51E-04 | 4.77E-10 |
| Cynomolgus | 0.4037 | 3.50E+05 | 2.57E-04 | 7.35E-10 |
| Mouse | 0.3068 | 2.94E+05 | 2.81E-04 | 9.54E-10 |

Cell-Based, Ex Vivo and In Vivo Biological Activity Assays

Figure 4:
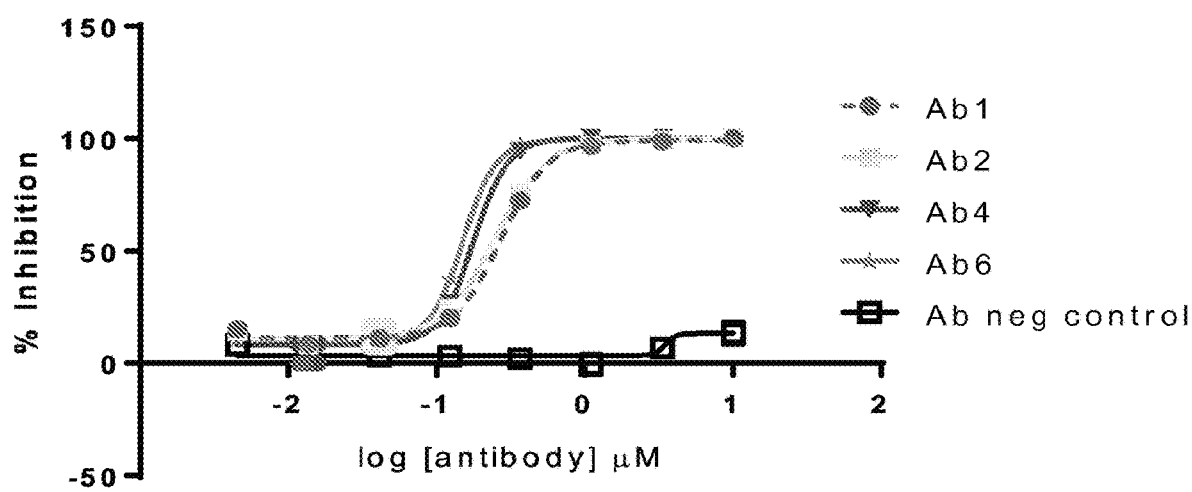
FIG. 4 shows the performance of the parental Ab1 antibody and other candidates in the cell-based reporter assay. Standard deviation for an average of 3 replicates is shown, but not visible on the graph for most data points due to their low magnitude.
Figure 5:
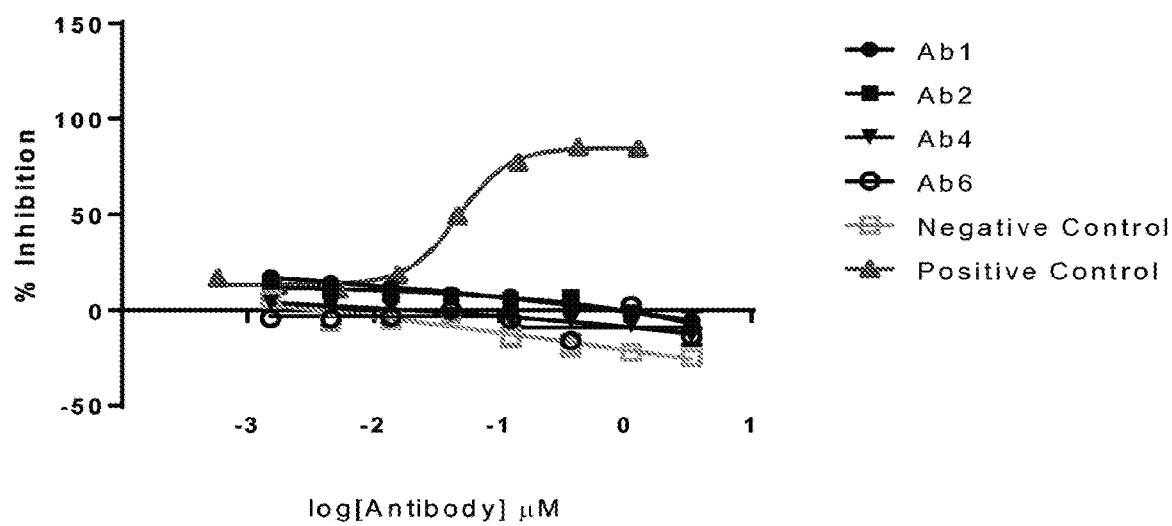
FIG. 5 shows graphically that certain antibodies do not inhibit proGDF11 activation.

Ab1 optimized variants were assessed in the GDF8 activation assay in a dose response study. In these experiments, 0.5 µM proMyostatin was pre-incubated with increasing amounts of the test article. Following this pre-incubation step, conditioned media from HEK293 cells overexpressing the mT112 and Furin proteases was added to release the mature growth factor from proMyostatin. Following incubation at 30° C. overnight, the material was added to 293T cells carrying a SMAD-based luciferase reporter plasmid, and the activity of the released material was recorded. Data are shown in FIG. 4.

Selectivity for Myostatin Over Other TGFβ Family Members

The selectivity of the candidate antibodies were also assessed by both binding and functional assays to verify the lack of cross reactivity to other members of the TGFβ family Human Myostatin and GDF11 share 90% identity in the mature growth factor domain, and 47% identity in the prodomain regions. From the epitope mapping studies, it was determined that the parental Ab1 molecule recognizes an epitope on the prodomain of proMyostatin and latent myostatin because ELISA assays have shown binding of this antibody to a construct consisting of the prodomain of myostatin. Even though the prodomains of myostatin and GDF11 share less than 50% identity, and we do not expect significant cross reactivity, the specificity of the lead antibodies was carefully assessed.

A sensitive assay for detecting interactions between the antibodies of interest and negative control reagents was developed. In this assay, biotinylated proGDF11 or biotinylated proMyostatin was immobilized on a ForteBio BLI streptavidin-coated sensor tip, which was applied to wells containing 30 µg/mL of antibody. Interactions of the analyte with the protein immobilized on the chip are measured by the magnitude of the response of the biosensor chip. The biosensor response after 5 minutes of association (a saturating signal for proGDF8) was compared between the two antigens, and expressed as the percent response for GDF8 binding. All antibodies had minimal interactions with proGDF11, compared to the robust binding events measured for proMyostatin.

TABLE 12

Interactions with proGDF11 at high concentrations of the candidate molecules

| | GDF11 response, expressed as a percentage of GDF8 response |
|---|---|
| Ab1 | 1.33% |
| Ab2 | 0.81% |
| Ab4 | 2.51% |
| Ab6 | 2.07% |

The antibody candidates were also evaluated in a GDF11 activation assay. In this assay, 50 nM proGDF11 is preincubated with increasing concentrations of the antibody. Following preincubation, conditioned medium from HEK293 cells overexpressing BMP-1 (a tolloid family protease) and PCSK5 (a furin family member specific for GDF11) was added to proteolytically activate proGDF11. Following overnight incubation at 30° C., the reaction mixtures are assessed for GDF11 activity in a SMAD-based reporter cell line. As is shown in Table 12, the anti-myostatin antibodies do not inhibit proGDF11 activation, while a positive control antibody imparts dose-dependent inhibition of GDF11 activation.

Binding affinities of antibody candidates were determined using the FortéBio Octet QKe dip and read label free assay system utilizing bio-layer interferometry. Antigens were immobilized to biosensors (streptavidin-coated biosensors for proGDF8, proGDF11 and proActivin; direct amine coupling for all others) in each experiment and the antibodies/constructs were presented in solution at high concentration (50 µg/mL) to measure binding interactions.

TABLE 13

Comparison of antibodies for binding to different forms of several TGFβ family members.

| | Ab2 | Ab4 | Ab6 | Ab1 |
|---|---|---|---|---|
| Pro GDF8 | 7.35E−09 | 9.24E−10 | 8.89E−10 | 6.23E−09 |
| Latent GDF8 | 7.84E−09 | 1.10E−09 | 1.12E−09 | 9.06E−09 |
| Mature GDF8 | — | — | — | — |
| Pro GDF11 | — | *1.25E−07 | *6.07E−08 | — |
| Mature GDF11 | — | — | — | — |
| Pro Activin A | — | — | — | — |
| Mature Activin A | — | — | — | — |
| BMP 9 | — | — | — | — |
| BMP10 | — | — | — | — |
| Mature TGFB1 | — | — | — | — |

*Non-specific binding.

Results from an antigen binding study are summarized in Table 13. There are some calculated Kd values which were fitted to data with poor binding response, which is indicated in the table as weak non-specific binding.

Evaluation of Fc-Region Functionality

The expected mechanism for anti-pro/latent-Myostatin therapy involves binding to a soluble target (pro/latent-Myostatin) and preventing proteolytic activation. As such, antibody dependent cell-mediated cytotoxicity and complement fixation are not required for this mechanism of action. Ab1 and its related variants were engineered to contain an IgG4-Fc region. It is understood that IgG4 antibodies generally lack effector function due to their weak binding to complement component C1q and Fcγ receptors.

To demonstrate the reduced capacity for effector function, Ab1 and related antibodies were tested for binding to CD64 (FcgRI) and C1q by ELISA. For comparison, an IgG1 variant of Ab1 was also prepared. In this assay, all IgG4 antibodies showed significantly weaker binding (10 to 20-fold) to CD64 and C1q compared to IgG1. The relative binding values at the EC50 are listed in Table 14.

TABLE 14

Relative binding affinities of Ab2 and related antibodies to CD64.

| Antibody | Isotype | Relative CD64 Binding @ EC50(%) | Relative C1q Binding @ EC50(%) |
|---|---|---|---|
| Ab1-G1 | IgG1 | 100 | 100 |
| Ab1 | IgG4 (S228P) | 10 | ND |
| Ab2 | IgG4 (S228P) | 5 | 8 |
| Ab3 | IgG4 (S228P) | 5 | 5 |
| Ab5 | IgG4 (S228P) | 8 | 9 |

Not determined

The apparent binding affinities of Ab1 and its related variants to CD64 and C1q are similar to other IgG4 clinical candidate antibodies, and are considerably reduced compared to antibodies of the IgG1 isotype. Based on the known biology of IgG4 antibodies, it is therefore concluded that the anti-pro/latent-Myostatin antibodies will not induce appreciable effector function in vivo.

Efficacy in Animal Models

Based on in vitro characterization, four antibodies were chosen to test in an in vivo study (Ab7, Ab1, Ab8 and Ab9). The objective of the study was to assess the ability of these four candidate antibodies to modulate muscle mass mice. Five (5) groups of ten (10) female SCID mice received test article administration by intraperitoneal (IP) injection once per week on Days 0, 7, 14, 21, 28, and 35. Prior to test article administration (Day 0), all animals underwent grip strength evaluation. Grip strength evaluation was also performed on the last day of the study (Day 42). On Day 0, blood was collected via retro-orbital bleed for assessment of complete blood counts (CBC). Following dosing, animals were evaluated daily for body weight and general health observations. On Day 42, following grip strength assessment, animals were sacrificed via $CO_2$ overdose and blood was collected via cardiac puncture for CBC assessment. Additional blood was collected for the preparation of plasma. Various tissues were isolated and weighed. The muscles collected were: gastrocnemius, pectoralis, soleus, triceps, tibialis anterior, quadriceps (rectus femoris) and diaphragm. The organs collected were: heart, kidney, spleen, liver and inguinal white adipose tissue. All tissues were weighed and snap frozen except for the gastrocnemius muscles which were fixed in formalin (leg 1) and OCT (leg 2) for histologic analysis.

Summary

Figure 6:
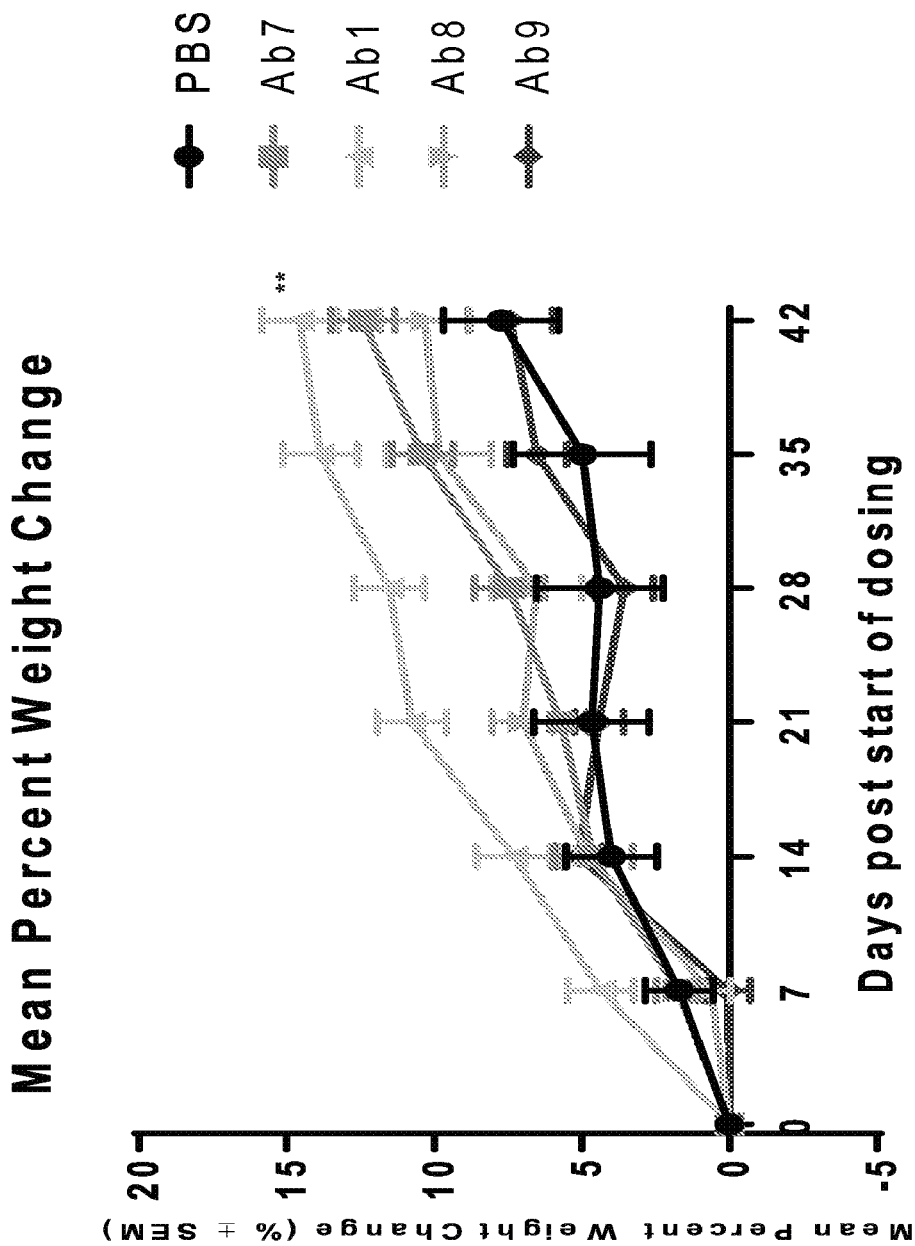
FIG. 6 shows results of an assay evaluating mean percent body weight change. Animals were weighed daily and the percent weight change from Day 0 was calculated. Data represent group means±SEM. The mean percent change data for each group on day 42 of the study were analyzed using a one-way ANOVA followed by Holm-Sidak's post hoc test in comparison to the PBS Control Group, **$p<0.01$.
Figure 7A:
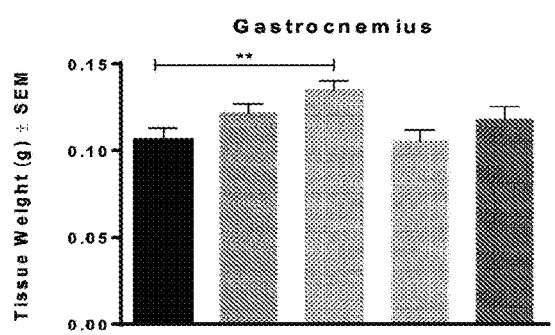
FIGS. 7A-7D show results of an assay evaluating tissue weights.
Figure 7B:
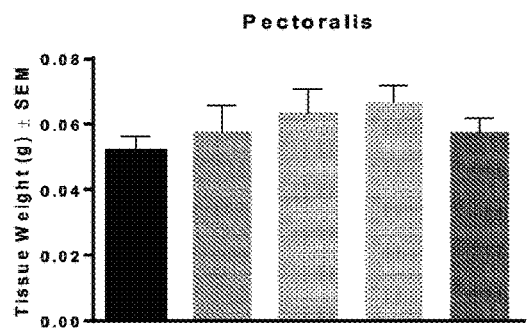
Figure 7C:
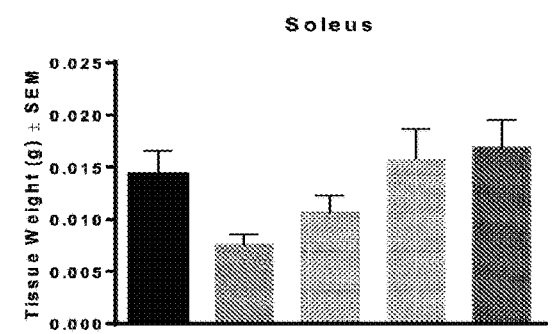
Figure 7D:
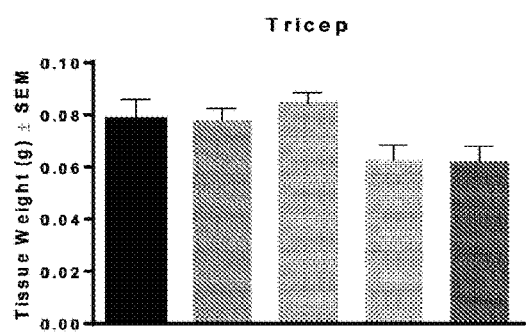

The mean daily percent weight change data for animals in study SCH-02 are shown in FIG. 6. Animals in all five groups gained weight on a weekly basis. Animals treated with the antibody Ab1 had the largest increase in body weight (14.6%) as depicted in FIG. 6. Only animals treated with Ab1 had a statistically significant increase in mean percent body weight change in comparison to animals in the vehicle (PBS) control group (FIG. 6).

Figure 8A:
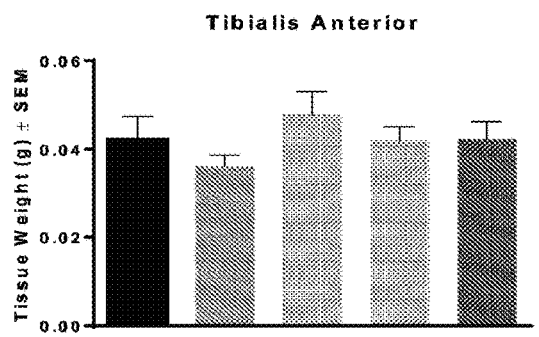
FIGS. 8A-8C show results of an assay evaluating tissue weights.
Figure 8B:
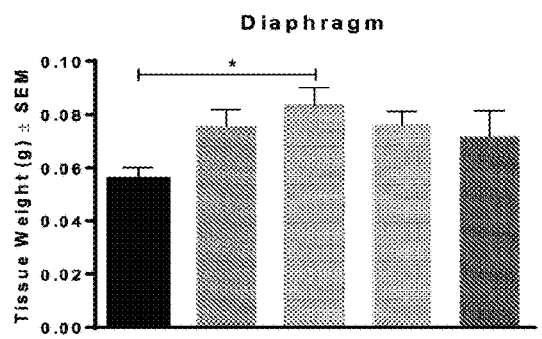
Figure 8C:
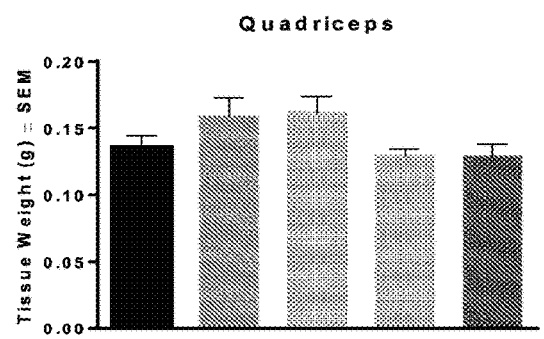

The weights for the dissected muscles are plotted in FIGS. 7 and 8. Animals treated with Ab1 had statistically significant increases in gastrocnemius (FIG. 7A) and diaphragm (FIG. 8B) weights compared to vehicle (PBS) control treated animals, 27.6% and 49.8%, respectively. Additional muscles from Ab1 treated animals showed increases in weight compared to the PBS control, but these differences were not statistically significant. There were no statistically significant differences between treatment groups for the mean tissue weights of heart, spleen, kidney, liver, and adipose tissue.

SCID Dose Response Study

In the in vivo study (above) animals dosed with Ab1 at 25 mg/kg once weekly for 6 weeks showed statistically significant increases in body weight and muscle weights (gastrocnemius and diaphragm) compared to animals dosed with the vehicle (PBS). This muscle enhancing activity of Ab1 was next investigated in more detail in a dose response study in SCID mice. In this study, whether the magnitude of the effect on muscle mass could be increased by increasing the dose of Ab1 to as high as 60 mg/kg/wk and whether the magnitude of the effect on muscle mass could be decreased by decreasing the dose of Ab1 to as low as 2 mg/kg/wk were examined. In this study, the activity of Ab1 was compared to two more antibodies (Ab8, which was originally tested in the study described above Ab10).

Ten (10) groups of ten (10) female SCID mice received test article administration by intraperitoneal (IP) injection (10 ml/kg) twice per week on Days 0, 3, 7, 10, 14, 17, 21, and 24. The doses of test articles were as follows: Ab1 (30 mg/kg, 10 mg/kg, 3 mg/kg and 1 mg/kg), Ab10 (10 mg/kg and 3 mg/kg), and Ab8 (10 mg/kg and 3 mg/kg). Control groups were dosed with PBS and IgG-control (30 mg/kg). Treatment groups are described in Table 15. Animals were 10 weeks old at the start of the study. Body weight was measured on day −4 and twice per week throughout the study, corresponding with dosing days. Body mass composition parameters (fat mass, lean mass and water content) were measured by Echo MRI (QNMR) on days −4, 7, 14, 21 and 28. Thirty (30) days after the first dose of antibody, animals were sacrificed via $CO_2$ overdose and blood was collected via cardiac puncture for CBC assessment and plasma preparation. Additionally, upon study termination, various tissues were isolated and weighed. The muscles collected were: gastrocnemius, soleus, tibialis anterior, quadriceps (rectus femoris) and diaphragm. Muscles were dissected from both the right and left legs of study mice. For analysis the weights of the individual muscles from both legs were combined and the average muscle weight in grams was calculated. The other tissues collected were: heart, kidney, spleen, liver and adipose tissue. All tissues were weighed and then snap frozen except for the gastrocnemius muscles which were fixed in formalin (left leg) and OCT (right leg) for histologic analysis.

TABLE 15

Study design

| Treatment Group | Test Article dose | # doses per week | Total dose per week | Animal IDs |
|---|---|---|---|---|
| 1 | PBS Control | 2 | 0 | 1-10 |
| 2 | IgG Control (30 mg/kg) | 2 | 60 mg/kg/wk | 11-20 |
| 3 | Ab1 (30 mg/kg) | 2 | 60 mg/kg/wk | 21-30 |
| 4 | Ab1 (10 mg/kg) | 2 | 20 mg/kg/wk | 31-40 |
| 5 | Ab1 (3 mg/kg) | 2 | 6 mg/kg/wk | 41-50 |
| 6 | Ab1 (1 mg/kg) | 2 | 2 mg/kg/wk | 51-60 |
| 7 | Ab10 (10 mg/kg) | 2 | 20 mg/kg/wk | 61-70 |
| 8 | Ab10 (3 mg/kg) | 2 | 6 mg/kg/wk | 71-80 |
| 9 | Ab8 (10 mg/kg) | 2 | 20 mg/kg/wk | 81-90 |
| 10 | Ab8 (3 mg/kg) | 2 | 6 mg/kg/wk | 91-100 |

Figure 9A:
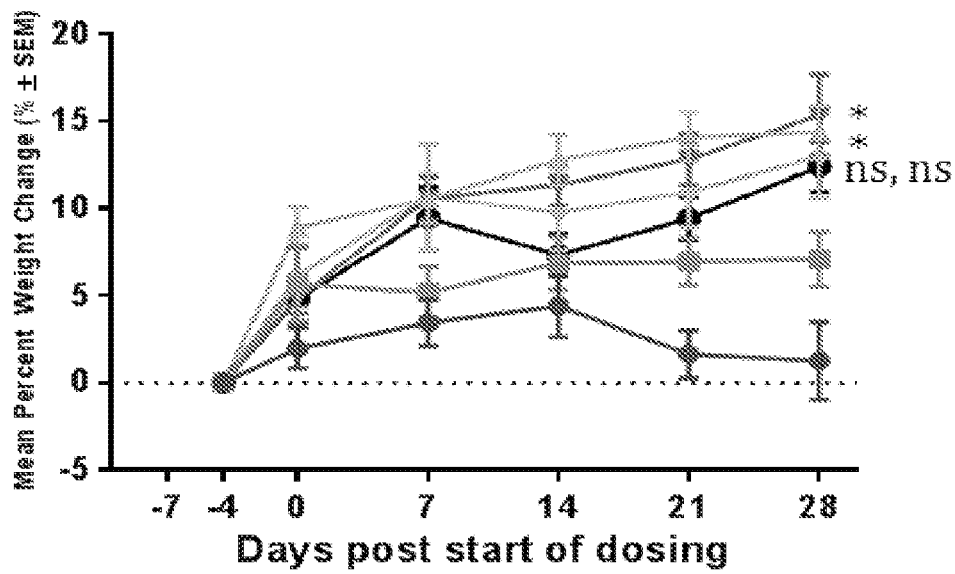
FIGS. 9A-9B show results of an assay evaluating mean percent body weight and lean mass change.
Figure 9B:
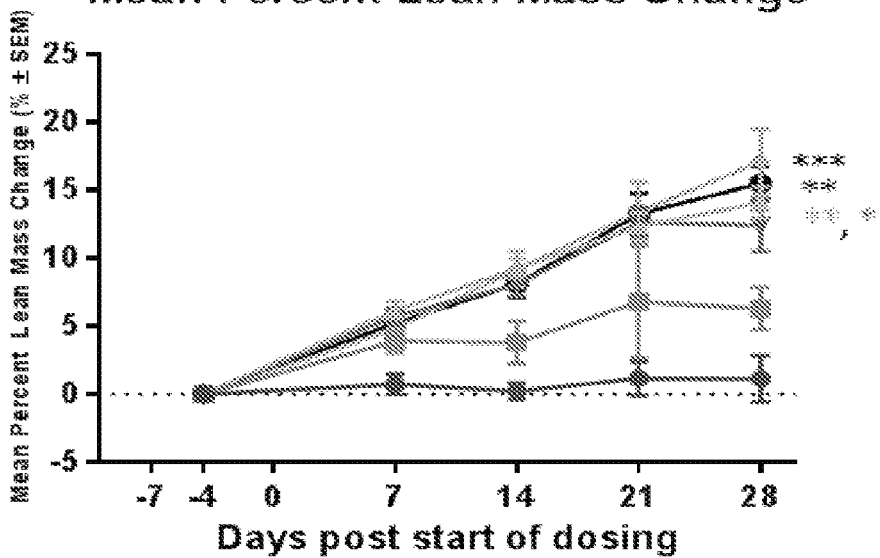

Mean percent weight change and mean percent lean mass change data for animals treated with vehicle (PBS), IgG control and different doses of Ab1 are shown in FIG. 9. Animals treated with Ab1 at 20 and 60 mg/kg/wk doses had significant increases in body weight on day 28 of the study compared to IgG control treated animals, 15.3% and 14.4%, respectively (FIG. 9A). All four groups of animals treated with Ab1 (60, 20, 6 and 2 mg/kg/wk doses) had statistically significant increases in lean mass on day 28 of the study compared to IgG control treated animals, 14.1%, 12.4%, 17.1%, and 15.5%, respectively (FIG. 9B).

Figures 10A, 10B:
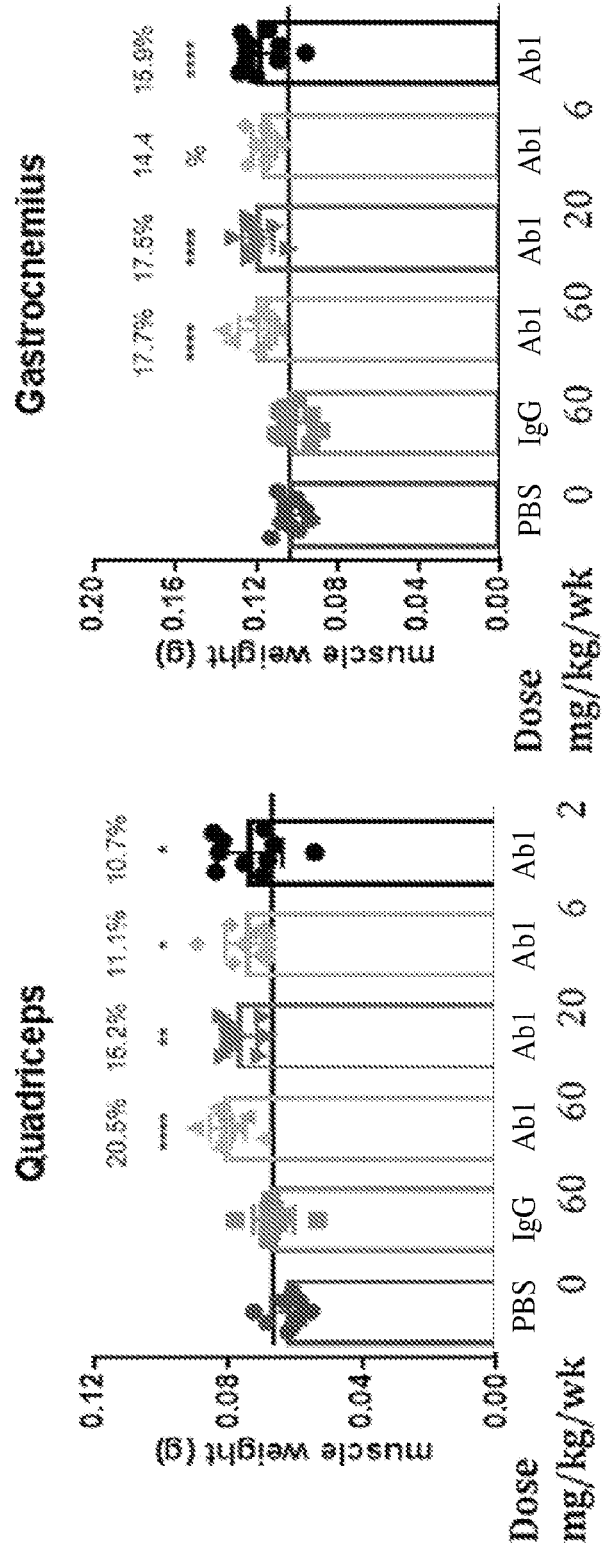
FIGS. 10A-10D are graphs showing results of an assay evaluating muscle weights.
Figures 10C, 10D:
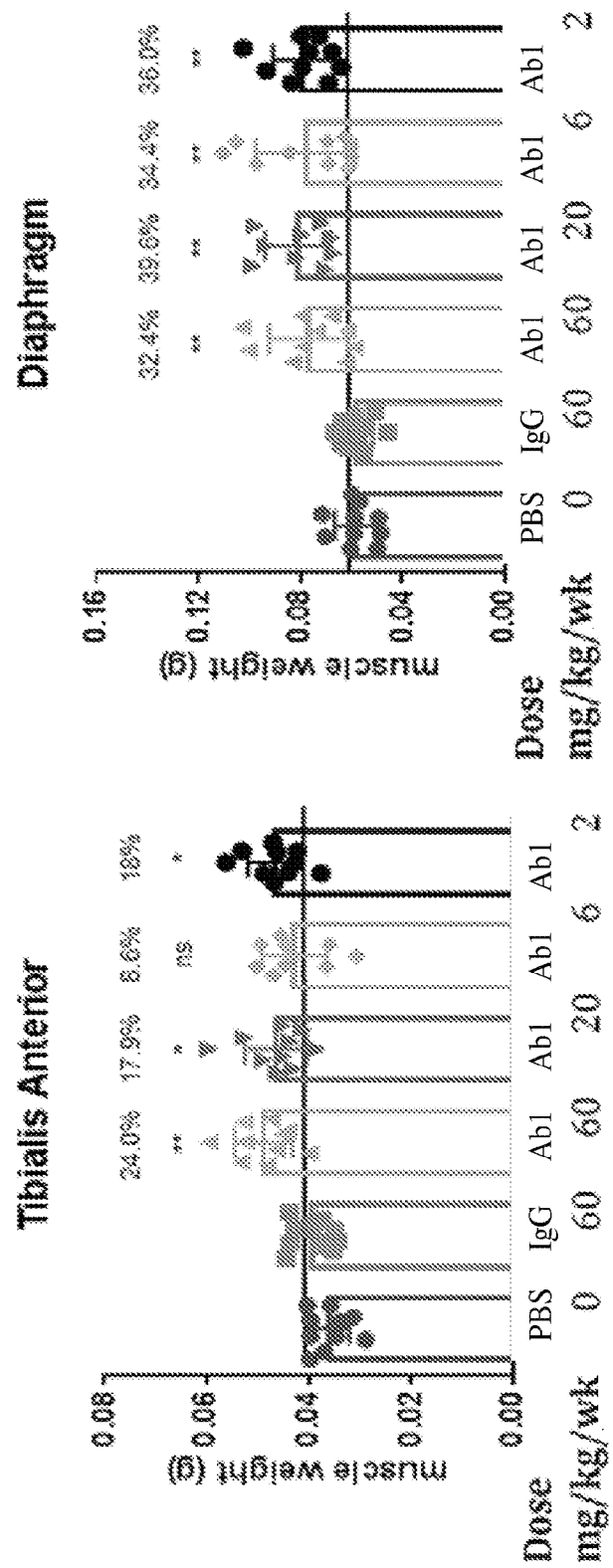

The weights for four muscles (quadriceps, gastrocnemius, tibialis anterior and diaphragm) are plotted in FIG. 10. The soleus muscle was also dissected, but the small size of the muscle resulted in an extremely variable data set. Animals treated with all doses of Ab1 had statistically significant increases in muscle weights compared to IgG control animals (FIG. 10). The mean percent changes in muscle mass compared to IgG control are shown above the corresponding bar on each muscle graph. Mean percent weight changes for quadriceps muscle ranged from 20.5% for the highest dose to 10.7% for the lowest dose (FIG. 10A). Mean percent weight changes for gastrocnemius muscle ranged from 17.7% for the highest dose to 15.9% for the lowest dose (FIG. 10B). Mean percent weight changes for tibialis anterior muscle ranged from 24.0% for the highest dose to 18.0% for the lowest dose (FIG. 10C). Mean percent weight changes for diaphragm muscle were greater than 30% for all dose groups (FIG. 10D). There were no statistically significant differences between treatment groups for the mean tissue weights of heart, spleen, kidney, liver, and adipose tissue.

Ab1 Treatment in a Dexamethasone Induced Muscle Atrophy Model

Given the ability of the anti-myostatin antibody Ab1 to build muscle mass in healthy SCID mice, it was determined whether Ab1 treatment could also protect animals from treatments that induce muscle atrophy. A model of corticosteroid-induced muscle atrophy was established by treating animals for two weeks with dexamethasone in their drinking water. The dose chosen (2.5 mg/kg/day) was able to induce significant decreases in lean body mass and the mass of individual hindlimb muscles. In the following experiment, animals were treated with different doses of Ab1 to determine if it could protect animals from this dexamethasone-induced muscle atrophy.

Figures 12A, 12B:
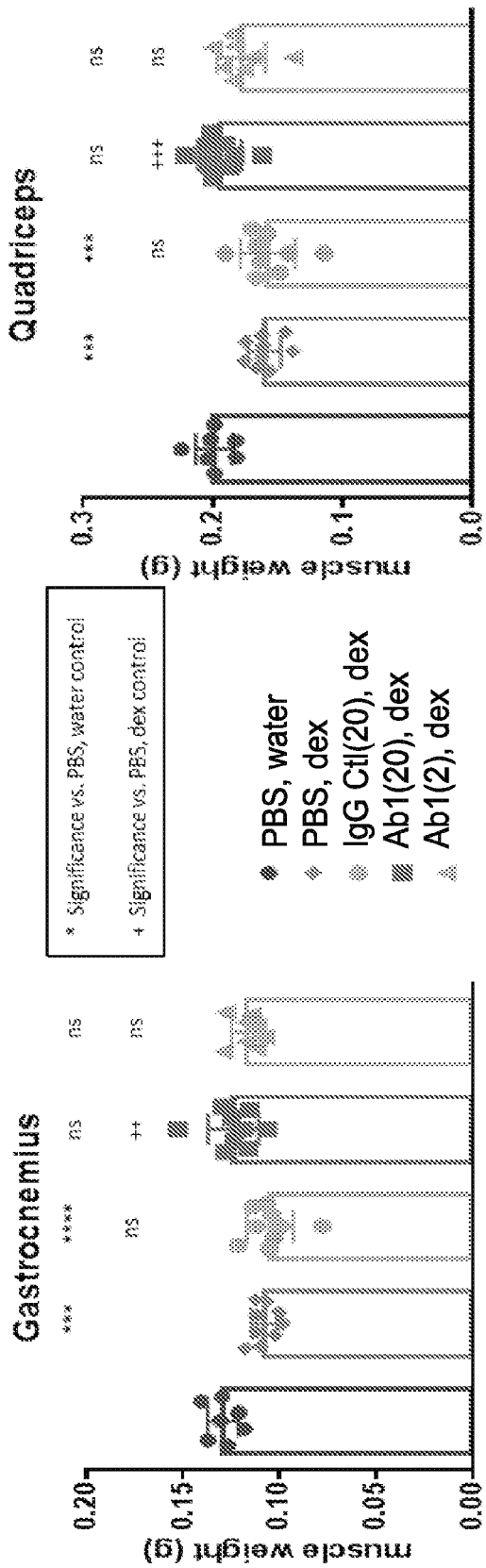
FIGS. 12A-12D are graphs showing results of an assay evaluating the weights of different muscles.
Figures 12C, 12D:
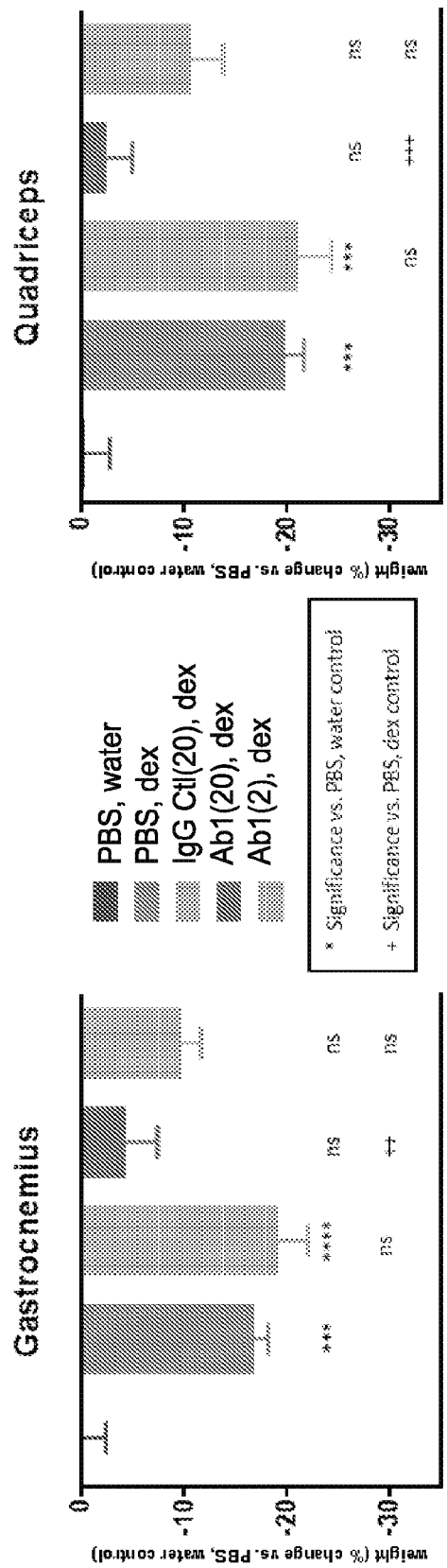

In this study, eight (8) groups of ten (10) male mice (C57BL/6) were enrolled in the study at 13.5 weeks of age. Starting on day 0 of the study, mice were given either normal drinking water (groups 1-4) or water containing dexamethasone (groups 5-8). Test articles were administered by intraperitoneal (IP) injection (10 ml/kg) twice per week on Days 0, 3, 7, and 10. The test articles and doses were as follows: PBS (groups 1 and 5), 10 mg/kg IgG Ctl (groups 2 and 6), 10 mg/kg Ab1 (groups 3 and 7), and 1 mg/kg Ab1 (groups 4 and 8). Treatment groups are described in Table 16. Body weight was measured at least twice per week throughout the study. Body mass composition parameters (fat mass, lean mass and water content) were measured by Echo MRI (QNMR) on days −1, 6, and 13. Fourteen (14) days after the first dose of antibody, animals were sacrificed via $CO_2$ overdose and blood was collected via cardiac puncture for plasma preparation. Additionally, upon study termination, various tissues were isolated and weighed. The muscles collected were: gastrocnemius, soleus, tibialis anterior, quadriceps (rectus femoris) and diaphragm. Muscles were dissected from both the right and left legs of study mice. For analysis the weights of the individual muscles from both legs were combined and the average muscle weight in grams was calculated. The other tissues collected were: heart, kidney, spleen, liver and adipose tissue. All tissues were weighed and then snap frozen except for the gastrocnemius muscles which were fixed in formalin (left leg) and OCT (right leg) for histologic analysis.

and quadriceps) are plotted in FIGS. 12A-12B. Animals that received dexamethasone via their drinking water and also received either PBS or IgG Control antibody showed significant atrophy in gastrocnemius and quadriceps muscles (groups 5 and 6) compared to the non-diseased control group (group 1). Animals treated with both dexamethasone and Ab1 at 20 mg/kg/wk (group 7), but not 2 mg/kg/wk, showed a significant difference in muscle weights when compared to either of the dexamethasone treated control groups (groups 5 and 6). In addition, mice treated with both dexamethasone and the antibody Ab1 at 20 mg/kg/wk (group 7) showed no significant difference in gastrocnemius and quadriceps weights when compared to the non-diseased control group (group 1). The mean percent difference in muscle weight of each group compared to the mean muscle weight of the control group (group 1, PBS and water) is shown in FIGS. 12C-12D. The percent decreases in gastrocnemius mass

TABLE 16

Treatment groups for Dexamethazone-induced atrophy model study

| Treatment Group | Dexamethasone in drinking water | Test Article dose | # doses per week | Total dose per week | Animal IDs |
|---|---|---|---|---|---|
| 1 | none | PBS Control | 2 | 0 | 1-10 |
| 2 | none | IgG Control (10 mg/kg) | 2 | 20 mg/kg/wk | 11-20 |
| 3 | none | Ab1 (10 mg/kg) | 2 | 20 mg/kg/wk | 21-30 |
| 4 | none | Ab1 (1 mg/kg) | 2 | 2 mg/kg/wk | 31-40 |
| 5 | 2.5 mg/kg/day | PBS Control | 2 | 0 | 51-60 |
| 6 | 2.5 mg/kg/day | IgG Control (10 mg/kg) | 2 | 20 mg/kg/wk | 61-70 |
| 7 | 2.5 mg/kg/day | Ab1 (10 mg/kg) | 2 | 20 mg/kg/wk | 71-80 |
| 8 | 2.5 mg/kg/day | Ab1 (1 mg/kg) | 2 | 2 mg/kg/wk | 81-90 |

Figures 11A, 11B:
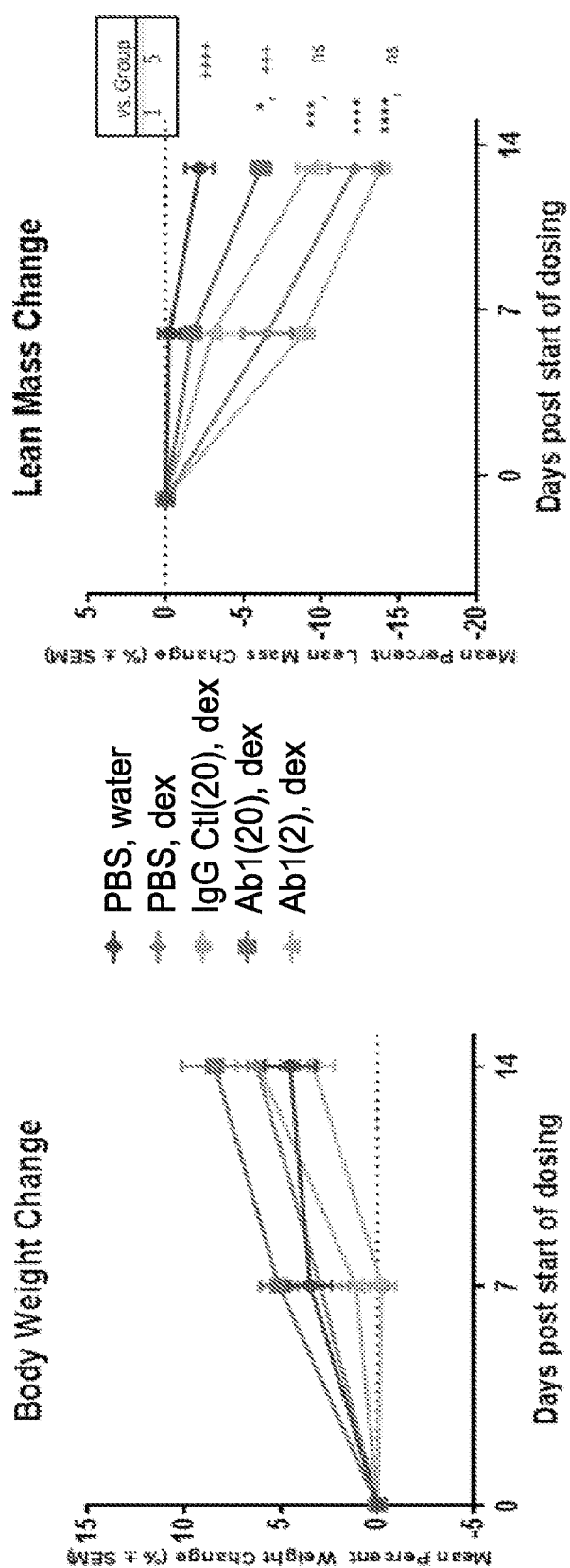
FIGS. 11A-11B show results of an assay evaluating mean percent body weight and lean mass change.

In this experiment it was determined whether treatment of mice with the anti-myostatin antibody Ab1 could protect animals from corticosteroid induced muscle atrophy. During the study body weight was measured twice weekly and lean mass by QNMR on days −1, 6 and 13. The mean percent weight change and mean percent lean mass change data for animals in the non-diseased control group (group 1) and the dexamethasone treated groups (groups 5-8) are shown in FIG. 12. There were no significant differences in mean percent body weight change between any of these treatment groups on day 14 (FIG. 11A). Treatment of mice with dexamethasone for two weeks led to a significant decrease in lean body mass (groups 5 and 6) compared to a control group (group 1) that was given normal drinking water (FIG. 11B). However, mice treated with both dexamethasone and the antibody Ab1 at 20 mg/kg/wk (group 7) showed no significant difference in percent change in lean body mass on day 14 of the study compared to the control group (group 1). Animals treated with Ab1 at 20 mg/kg/wk, but not 2 mg/kg/wk, showed a significant difference in percent change in lean body mass on day 14, when compared to either of the dexamethasone treated control groups (groups 5 and 6).

At the end of the two week treatment with dexamethasone and the test articles, individual muscles were dissected and weighed. The weight data for two muscles (gastrocnemius induced by dexamethasone treatment in the PBS and IgG Ctl groups were 16.5% and 18.9%, respectively. In contrast, animals treated with both dexamethasone and 20 mg/kg/wk of Ab1 only had a 4.0% decrease in gastrocnemius muscle mass which was not statistically different from the non-diseased control group (group 1). While animals treated with both dexamethasone and 2 mg/kg/wk Ab1 (group 8) only had a 10% decrease in gastrocnemius muscle mass, the muscle mass decrease for this group was not statistically different than the decreases for the PBS and IgG control groups (groups 5 and 6). Similar results were seen for the quadriceps muscle (FIG. 12D).

Ab1 Treatment in a Casting Induced Muscle Atrophy Model

Given the ability of the anti-myostatin antibody Ab1 to build muscle mass in healthy SCID mice, whether Ab1 treatment could also protect animals from treatments that induce muscle atrophy was investigated. A model of disuse atrophy was established by casting the right leg of mice for two weeks. Casting the right leg with the foot in a plantar flexion position for this time period was able to induce significant decreases in the mass of individual hindlimb muscles. In the following experiment animals were treated with different doses of Ab1 to determine the extent to which it protects animals from this casting induced muscle atrophy.

TABLE 17

Treatment groups for casting-induced atrophy model study

| Treatment Group | Casting | Test Article dose | # doses per week | Total dose per week | Animal IDs |
|---|---|---|---|---|---|
| 1 | No cast | PBS Control | 2 | 0 | 1-10 |
| 2 | No cast | IgG Control (10 mg/kg) | 2 | 20 mg/kg/wk | 11-20 |

TABLE 17-continued

Treatment groups for casting-induced atrophy model study

| Treatment Group | Casting | Test Article dose | # doses per week | Total dose per week | Animal IDs |
|---|---|---|---|---|---|
| 3 | No cast | Ab1 (10 mg/kg) | 2 | 20 mg/kg/wk | 21-30 |
| 4 | No cast | Ab1 (1 mg/kg) | 2 | 2 mg/kg/wk | 31-40 |
| 5 | Casted | PBS Control | 2 | 0 | 51-60 |
| 6 | Casted | IgG Control (10 mg/kg) | 2 | 20 mg/kg/wk | 61-70 |
| 7 | Casted | Ab1 (10 mg/kg) | 2 | 20 mg/kg/wk | 71-80 |
| 8 | Casted | Ab1 (1 mg/kg) | 2 | 2 mg/kg/wk | 81-90 |

In this study, eight (8) groups of ten (10) male mice (C57BL/6) were enrolled in the study at 14.5 weeks of age. Starting on day 0 of the study, mice were placed under anesthesia and a cast was applied to the right hindlimb with the foot in a plantar flexion position (groups 5-8). The control groups (groups 1-4) were also placed under anesthesia but no cast was placed on the hindlimb. Test articles were administered by intraperitoneal (IP) injection (10 ml/kg) twice per week on Days 0, 3, 7, and 10. The test articles and doses were as follows: PBS (groups 1 and 5), 10 mg/kg IgG Ctl (groups 2 and 6), 10 mg/kg Ab1 (groups 3 and 7), and 1 mg/kg Ab1 (groups 4 and 8). Treatment groups are described in Table 17. Body weight was measured at least twice per week throughout the study. Body mass composition parameters (fat mass, lean mass and water content) were measured by Echo MRI (QNMR) on days −1, 7, and 14. Fourteen (14) days after the first dose of antibody, animals were sacrificed via $CO_2$ overdose and blood was collected via cardiac puncture for plasma preparation.

Additionally, various tissues were isolated and weighed. The muscles collected were: gastrocnemius, soleus, plantaris, tibialis anterior, and quadriceps (rectus femoris). For analysis the weights of the individual muscles from the right hindlimb of the animals were collected. The other tissues collected were: heart, adipose and spleen. All tissues were weighed and then snap frozen except for the gastrocnemius muscles which were fixed in formalin for histologic analysis.

Summary

In this experiment, whether treatment of mice with the anti-myostatin antibody Ab1 could protect mice from disuse muscle atrophy induced by casting of the right hindlimb was tested. During the study, body weight was measured twice weekly and lean mass was measured by QNMR on days −1, 7 and 14. The mean percent weight change and mean percent lean mass change data for animals in the non-diseased control group (group 1) and the groups that were casted for two weeks (groups 5-8) are shown in FIG. 13. Casting of the right hind limb did not have any negative effects on body weight gain (FIG. 13A) and any differences in lean mass of groups were not significant (FIG. 13B).

Figures 14A, 14B:
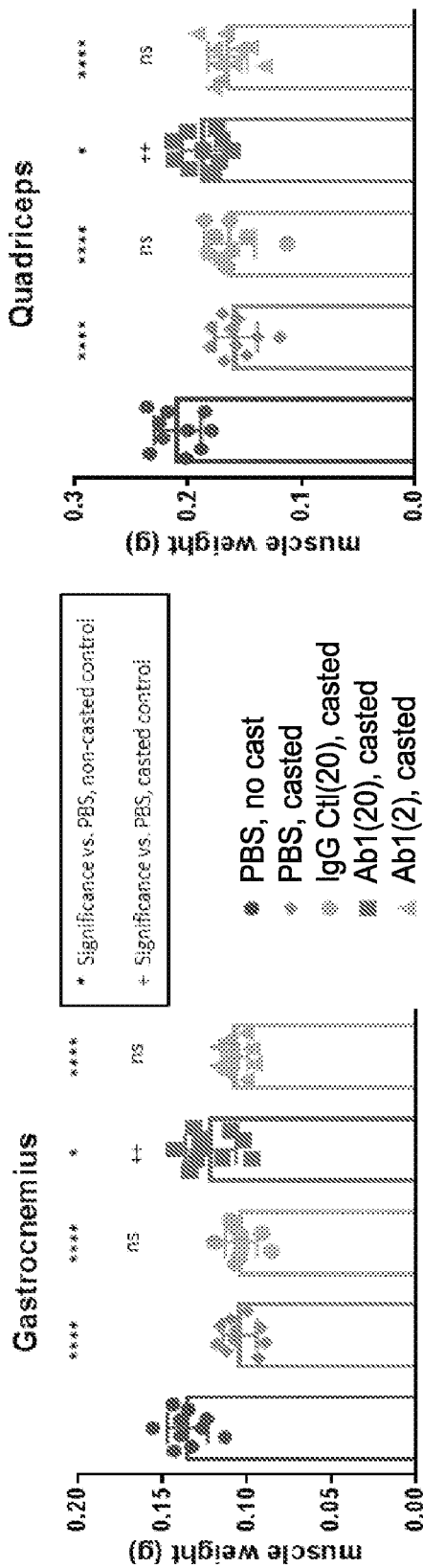
FIGS. 14A-14D show results of an assay evaluating muscle weights.
Figures 14C, 14D:
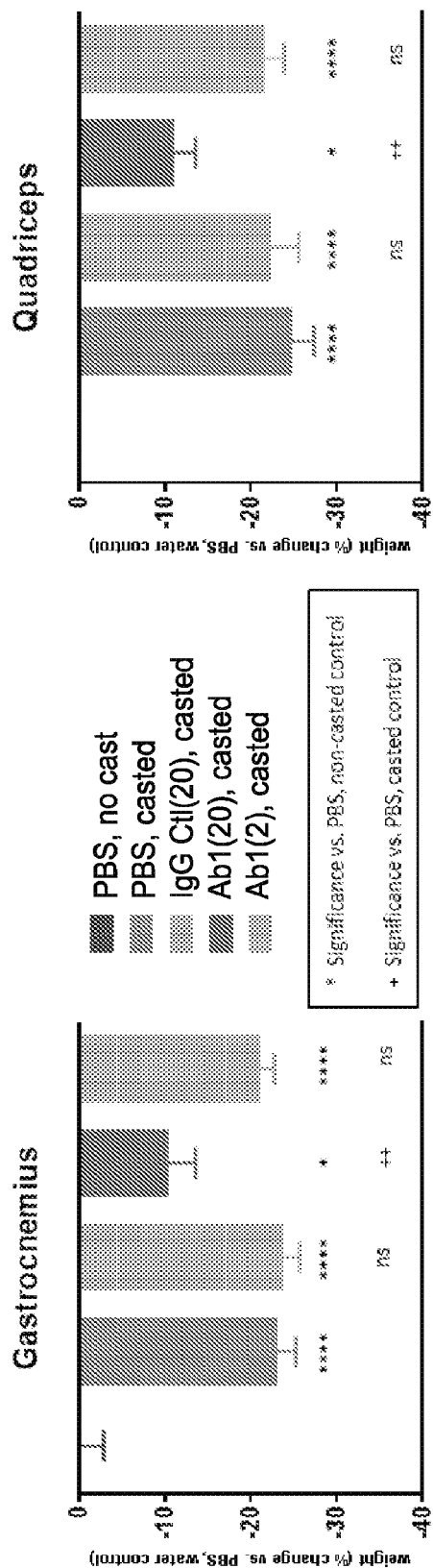
Figures 15, 16A, 16B:
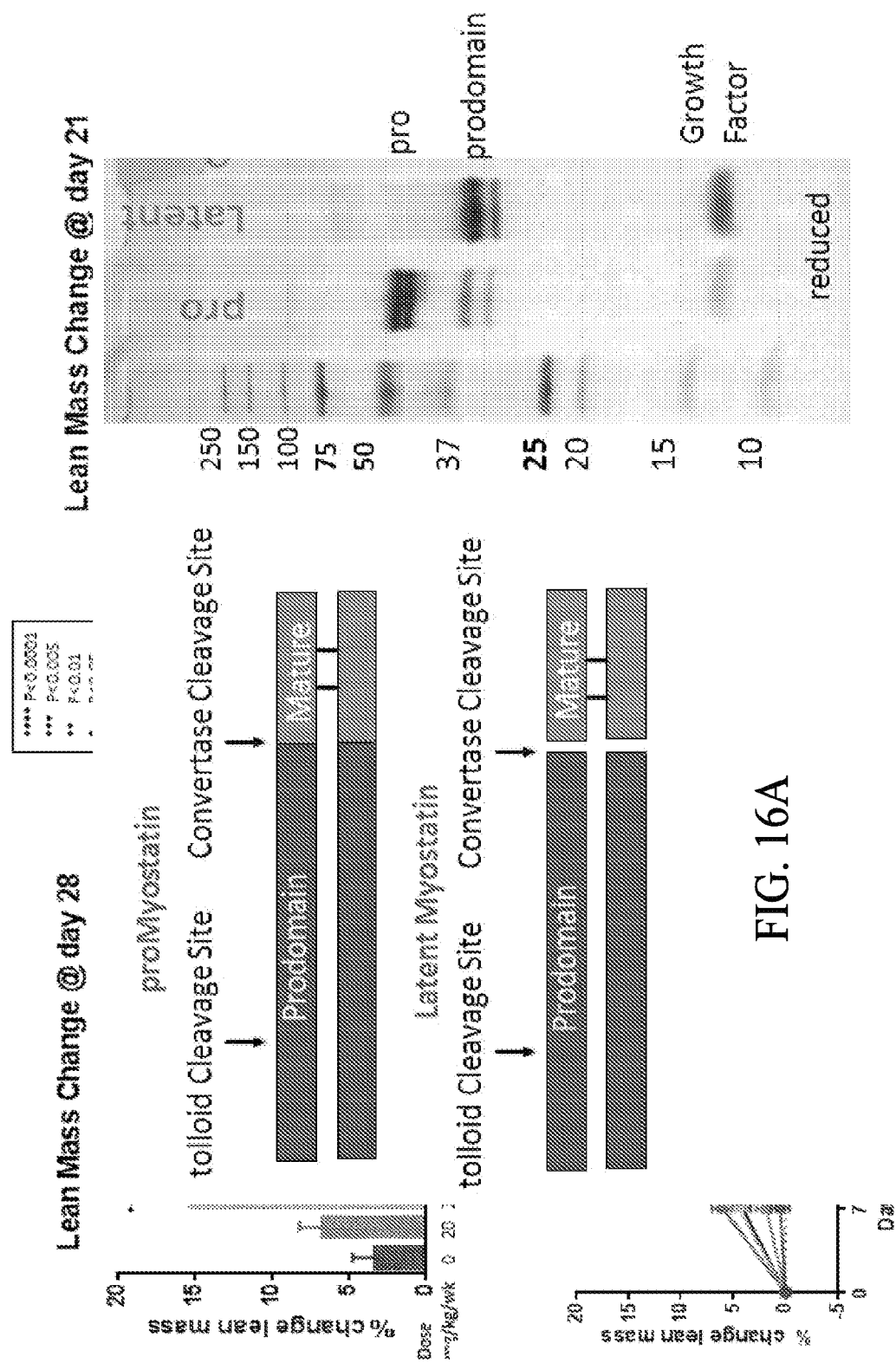
FIG. 15 shows results of an assay evaluating the lean mass change at Day 21 (top right) and Day 28 (top left). It also depicts the percent change in lean mass at three different doses, 20 mg/kg/wk (bottom left), 2 mg/kg/wk (bottom middle), and 0.5 mg/kg/wk (bottom right) of the tested antibodies, PBS control, and IgG control. Statistical evaluation was performed using a one-way ANOVA followed by a Dunnett's multiple comparisons test vs. group 1 (**$p<0.0001$, *$p<0.005$, **$p<0.01$, *$p<0.05$) and vs. the IgG control. For the top panel, bars from left-to-right are: PBS; IgG Ctrl 20 mg/mk/wk; Ab1 20 mg/mk/wk; Ab1 2 mg/mk/wk; Ab1 0.5 mg/mk/wk; Ab2 20 mg/mk/wk; Ab2 2 mg/mk/wk; Ab2 0.5 mg/mk/wk; Ab4 20 mg/mk/wk; Ab4 2 mg/mk/wk; Ab4 0.5 mg/mk/wk; Ab6 20 mg/mk/wk; Ab6 2 mg/mk/wk; and Ab6 0.5 mg/mk/wk.
FIGS. 16A-16B show the domain structure and evaluation of Myostatin precursor forms.
Figures 17A, 17B:
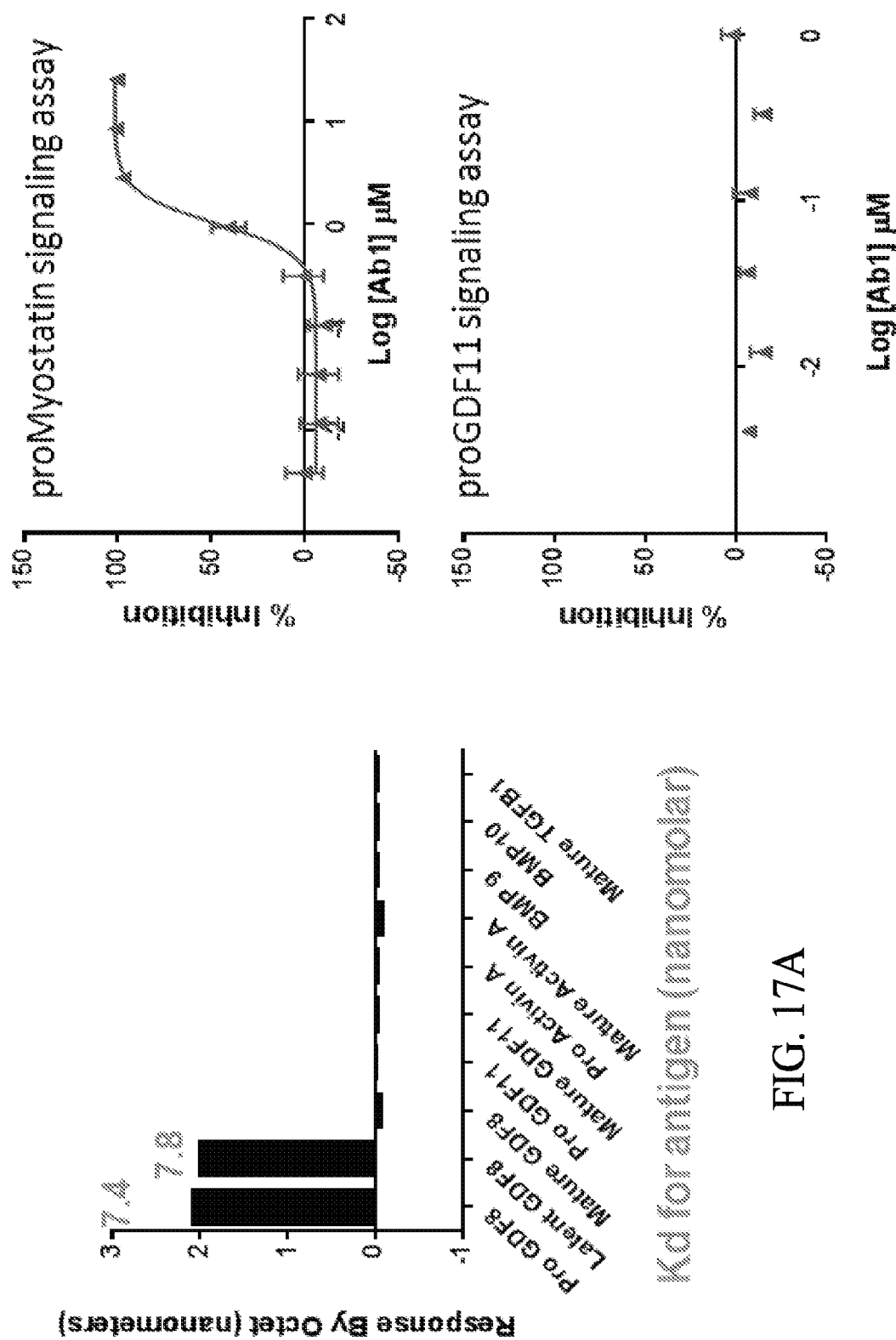
FIGS. 17A-17B show Ab1 is specific for Myostatin.
Figure 18A:
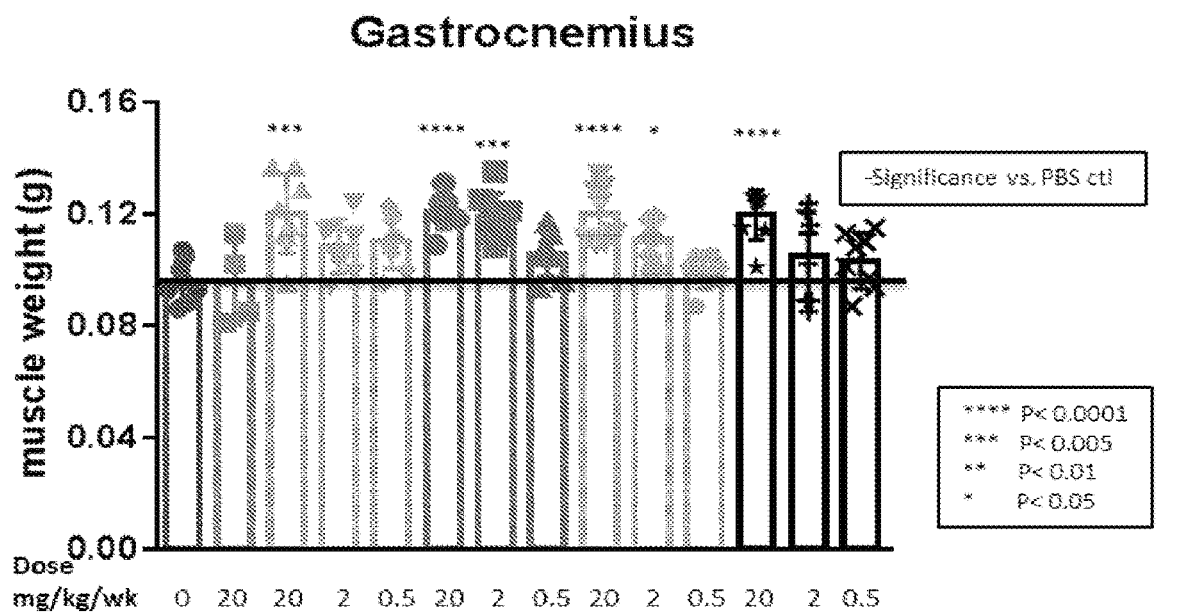
Figure 18B:
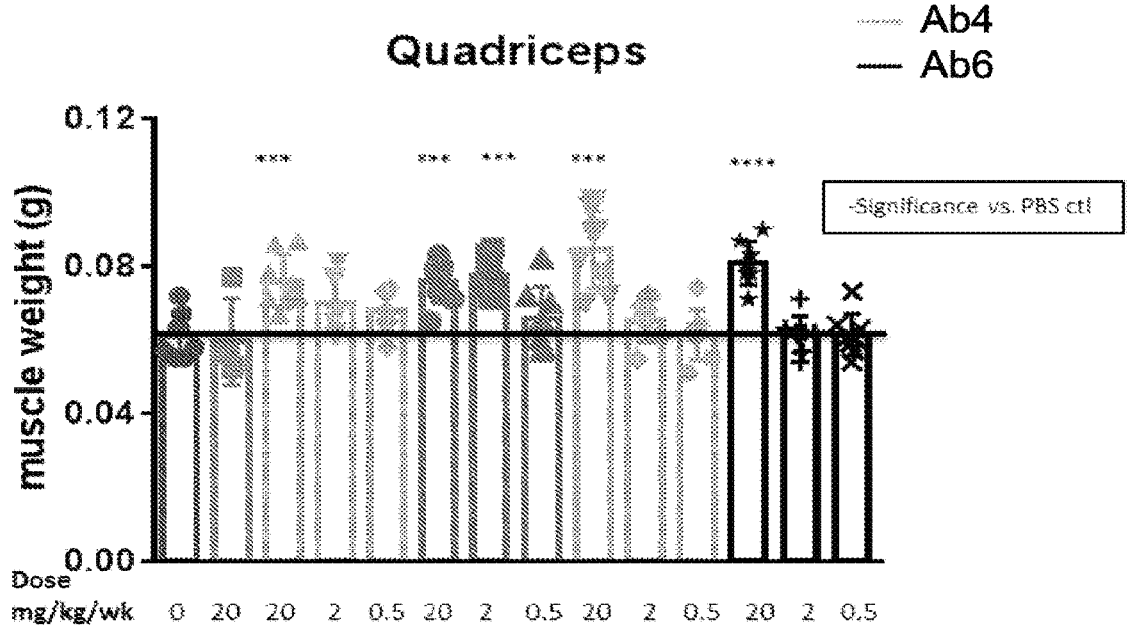
Figure 19:
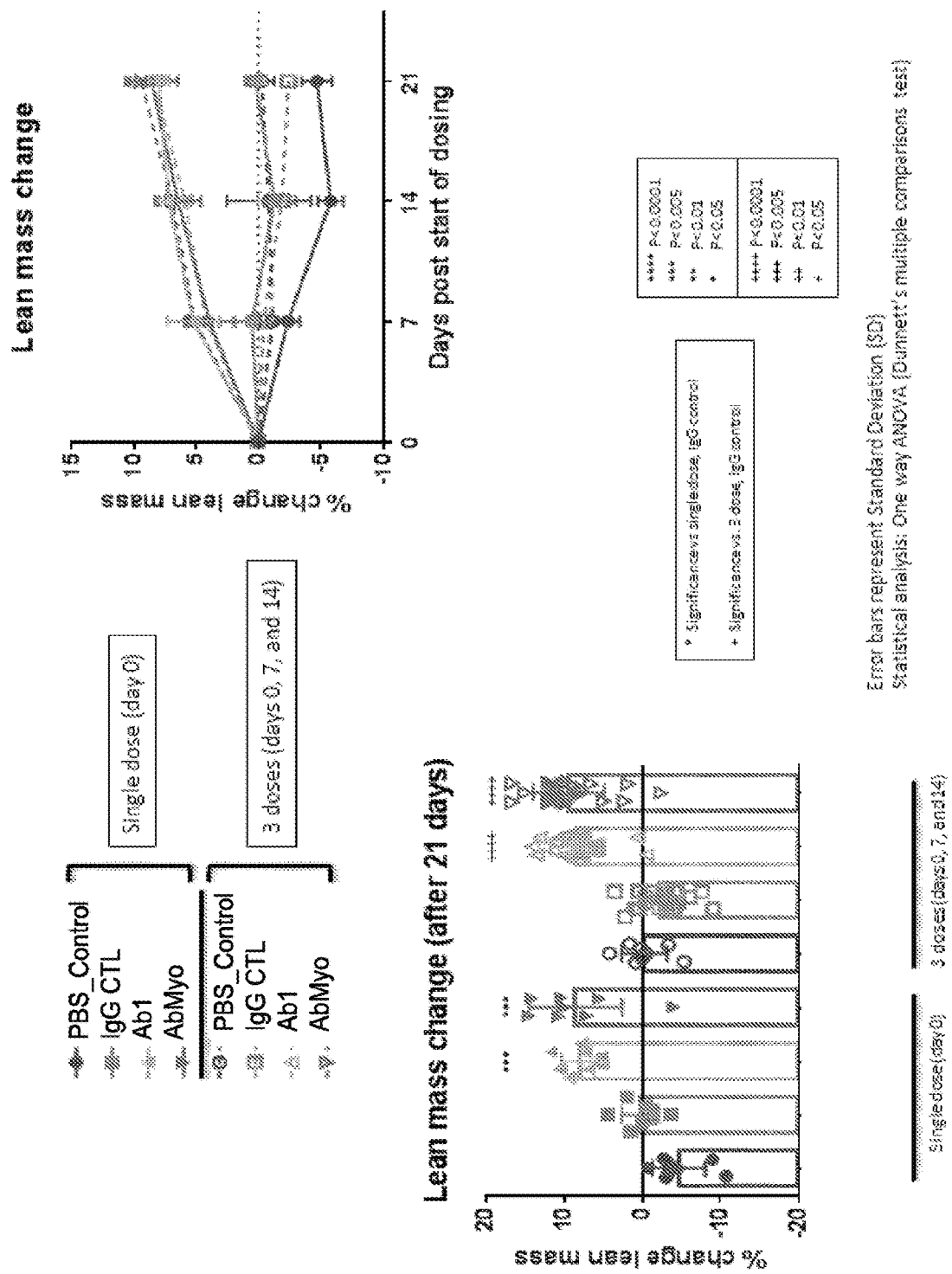
FIG. 19 shows the results of a duration of action study comparing Ab1 to an existing myostatin antibody (AbMyo). PBS was used as a negative control; IgG was used as a positive control. The lean mas change was examined under different dosing protocols after 21 days.
Figure 20:
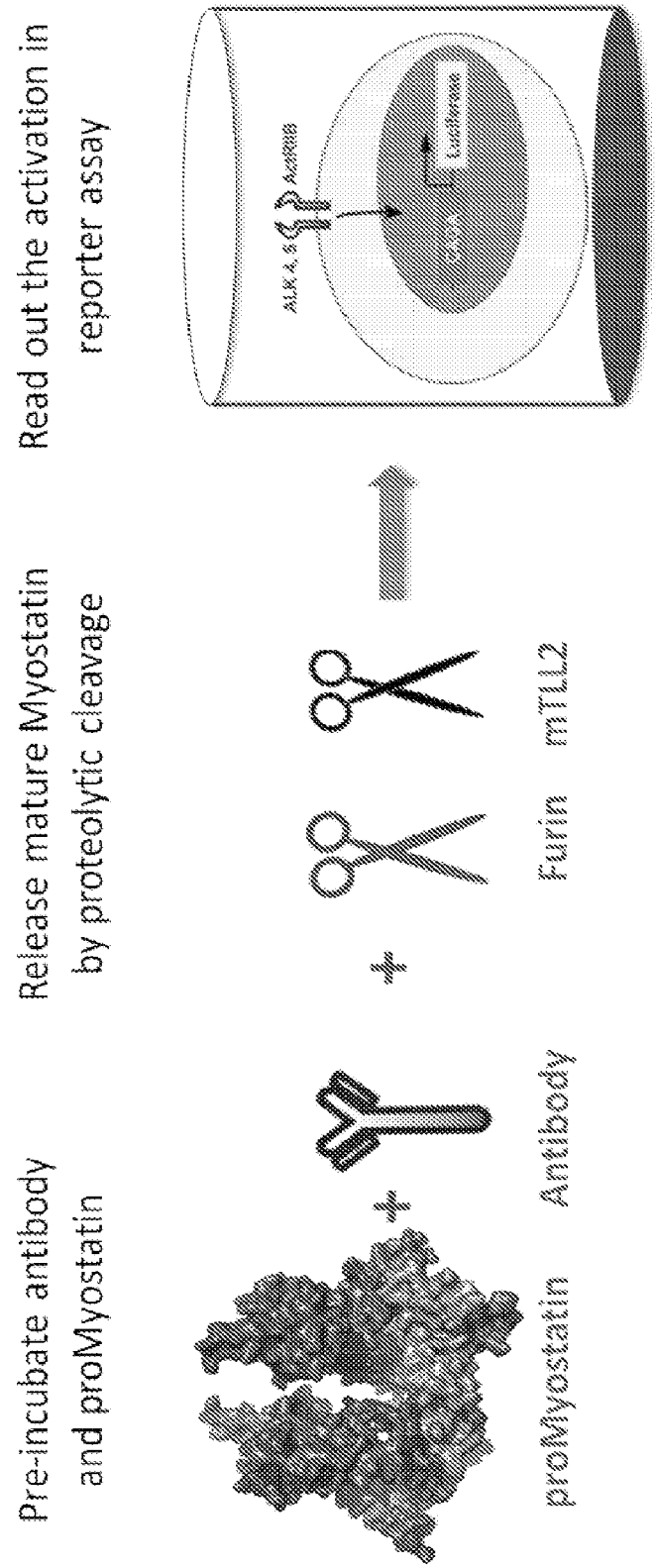
FIG. 20 is a schematic illustrating a assay that reconstitutes Myostatin activation in vitro.

At the end of the two week study individual muscles were dissected and weighed. The weight data for two muscles (gastrocnemius and quadriceps) are plotted in FIGS. 14A-14B. Animals that had their leg casted and also received either PBS or IgG Control antibody showed significant atrophy in gastrocnemius and quadriceps muscles (groups 5 and 6) compared to the non-casted control group (group 1). Animals that were both casted and dosed with Ab1 at 20 mg/kg/wk (group 7), but not 2 mg/kg/wk, showed a significant difference in muscle weights when compared to either of the casted control groups (groups 5 and 6). In addition, casted mice that were treated with the antibody Ab1 at 20 mg/kg/wk (group 7) showed no significant difference in gastrocnemius and quadriceps weights when compared to the non-casted control group (group 1). The mean percent difference in muscle weight of each group compared to the mean muscle weight of the non-casted control group (group 1) is shown in FIGS. 14C-14D. The percent decreases in gastrocnemius mass induced by casting in the PBS and IgG Ctl groups were 22.8% and 23.5%, respectively. In contrast, casted mice that were treated with 20 mg/kg/wk of Ab1 only had a 10.0% decrease in gastrocnemius muscle mass. This difference was found to be statistically different from the casted control groups that received PBS and IgG Ctl antibody (group 5 and 6). The muscle mass decrease for the casted mice treated with 2 mg/kg/wk Ab1 was not statistically different than the decreases for the PBS and IgG control groups (groups 5 and 6) Similar results were seen for the quadriceps muscle (FIG. 14D). Additional data is provided in FIGS. 15-20.

SCID Dose Response Study with Ab1, Ab2, Ab4 and Ab6

The previous in vivo studies with Ab1 have demonstrated that Ab1 can increase muscle mass in healthy animals as well as prevent muscle loss in mouse models of muscle atrophy (dexamethasone and casting induced atrophy). Antibody engineering efforts identified three antibodies with in vitro characteristics that were better than Ab1. In this study, in SCID mice, the in vivo activity of these antibodies was compared at three different doses to the already established activity of Ab1.

Fourteen (14) groups of eight (8) female SCID mice received test article administration by intraperitoneal (IP) injection (10 ml/kg) twice per week on Days 0, 3, 7, 10, 14, 17, 21, and 24. The doses of test articles were as follows: Ab1, Ab2, Ab4 and Ab6 were given at 3 different doses (10 mg/kg, 1 mg/kg, and 0.25 mg/kg) and the IgG-Ctl antibody was given at 10 mg/kg. Treatment groups are described in Table 18. Animals were 10 weeks old at the start of the study. Body weight was measured twice per week throughout the study, corresponding with dosing days. Body mass composition parameters (fat mass, lean mass and water content) were measured by Echo MRI (QNMR) on days 0, 7, 14, 21 and 28. Twenty-eight (28) days after the first dose of antibody, animals were sacrificed via $CO_2$ overdose and blood was collected via cardiac puncture for plasma preparation.

Additionally, various tissues were isolated and weighed. The muscles collected were: gastrocnemius, soleus, tibialis anterior, quadriceps (rectus femoris), extensor digitorum longus, and diaphragm. Muscles were dissected from both the right and left legs of study mice. For analysis the weights of the individual muscles from both legs were combined and the average muscle weight in grams was calculated. The other tissues collected were: heart, kidney, spleen, liver and adipose tissue. All tissues were weighed and then snap frozen except for the left gastrocnemius muscles which was fixed in formalin for histologic analysis.

TABLE 18

Treatment groups for dose response model study

| Treatment Group | Test Article dose | # doses per week | Total dose per week | Animal IDs |
|---|---|---|---|---|
| 1 | PBS Control | 2 | 0 | 1-8 |
| 2 | IgG Control (10 mg/kg) | 2 | 20 mg/kg/wk | 9-16 |
| 3 | Ab1 (10 mg/kg) | 2 | 20 mg/kg/wk | 17-24 |
| 4 | Ab1 (1 mg/kg) | 2 | 2 mg/kg/wk | 25-32 |
| 5 | Ab1 (0.25 mg/kg) | 2 | 0.5 mg/kg/wk | 33-40 |
| 6 | Ab2 (10 mg/kg) | 2 | 20 mg/kg/wk | 41-48 |
| 7 | Ab2 (1 mg/kg) | 2 | 2 mg/kg/wk | 49-56 |
| 8 | Ab2 (0.25 mg/kg) | 2 | 0.5 mg/kg/wk | 57-64 |
| 9 | Ab4 (10 mg/kg) | 2 | 20 mg/kg/wk | 65-72 |
| 10 | Ab4 (1 mg/kg) | 2 | 2 mg/kg/wk | 73-80 |
| 11 | Ab4 (0.25 mg/kg) | 2 | 0.5 mg/kg/wk | 81-88 |
| 12 | Ab6 (10 mg/kg) | 2 | 20 mg/kg/wk | 89-96 |
| 13 | Ab6 (1 mg/kg) | 2 | 2 mg/kg/wk | 97-104 |
| 14 | Ab6 (0.25 mg/kg) | 2 | 0.5 mg/kg/wk | 105-112 |

Example 3: Chemistry/Pharmaceutical Sciences

Ab2 is a humanized monoclonal antibody of the IgG4 subtype with Proline substituted for Serine at position 228. This generates an IgG1-like hinge sequence and minimizes the incomplete formation of inter-chain disulfide bridges which is characteristic of IgG4. The complete amino acid sequence of the heavy and light chains of Ab2 are shown below. The complementarity-determining regions (CDRs) are underlined. purple: N-linked glycosylation consensus sequence site; light blue: potential cleavage site; red: potential deamidation site; light green: potential isomerization site; Dark blue: potential methionine oxidation site; Bold: expected N-terminal pyroglutamic acid (FIGS. 21A-21B).

Molecular modeling of Ab1 identified several potential sites of post-translational modifications. Two asparagines in the light chain and seven asparagines in the heavy chain are susceptible to deamidation. Two of these residues are located within CDR regions of the heavy chain.

Native IgG4 mAbs may have incomplete formation of inter-heavy chain disulfide bridges, with the two half molecules (each containing one heavy and one light chain) maintained in the intact antibody structure by noncovalent interactions. IgG4 molecules may be prone to exchange of half-molecules in vitro and in vivo, and the level of half molecules must be consistent across manufacturing batches. The substitution of Ser to Pro in the backbone of the IgG4 structure results in an IgG1-like hinge sequence, thereby enabling the formation of inter-chain disulfide bonds and markedly stabilizing the antibody structure. The integrity and stability of the hinge region is monitored during development with extended characterization, using such assays as non-reducing capillary electrophoresis and quantitation of free sulfhydryls. The potential for chain swapping is monitored in vivo.

Summary

A pro/latent-Myostatin-specific antibody that blocks the activation of proMyostatin and/or latent myostatin is provided herein. Administration of this activation-blocking antibody to healthy mice increases lean body mass and muscle size, with only a single dose needed to sustain the muscle-enhancing effect over a 1 month period. Additionally, antibody administration protects healthy mice from muscle atrophy in two separate models of muscle wasting. The data demonstrate that blocking myostatin activation promotes robust muscle growth and prevents muscle atrophy in vivo, and represents an alternative mechanism for therapeutic interventions of muscle wasting.

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used. Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present disclosure.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The invention claimed is:

1. A host cell comprising a polynucleotide encoding an antibody or antigen-binding fragment thereof that specifically binds to pro/latent myostatin, binds to pro/latent myostatin with a decreased affinity at an acidic pH as compared to a neutral or physiological pH, and inhibits myostatin signaling after binding, wherein the host cell is prepared by the steps of:
  (i) screening for an antibody or antigen-binding fragment that specifically binds to pro/latent myostatin as compared to mature myostatin and/or another member of the transforming growth factor beta family;
  (ii) screening the antibody or antigen-binding fragment thereof for inhibition of myostatin signaling;
  (iii) assaying the antibody or antigen-binding fragment for binding to pro/latent myostatin wherein the antibody or fragment binds to pro/latent myostatin with a decreased affinity at an acidic pH as compared to a neutral or physiological pH;
  (iv) isolating a polynucleotide encoding the antibody or antigen-binding fragment; and
  (v) incorporating the polynucleotide in the host cell.

2. The host cell of claim 1, wherein the host cell is a mammalian cell.

3. The host cell of claim 1, wherein the host cell is a NSO cell, a HEK293 cell, or a CHO cell.

4. The host cell of claim 1, wherein step (ii) comprises screening the antibody or antigen-binding fragment thereof using a cell-based assay.

5. The host cell of claim 4, wherein the cell-based assay is a reporter assay.

6. The host cell of claim 5, wherein the reporter assay is a SMAD-based reporter assay.

7. A cell line comprising the host cell of claim 1.

8. The cell line of claim 7, wherein the cell line is a mammalian cell line.

9. The cell line of claim 7, wherein the cell line is a NSO cell line, a HEK293 cell line, or a CHO cell line.

* * * * *

UNITED STATES PATENT AND TRADEMARK OFFICE
CERTIFICATE OF CORRECTION

| | | |
|---|---|---|
| PATENT NO. | : 11,925,683 B2 | Page 1 of 1 |
| APPLICATION NO. | : 17/446897 | |
| DATED | : March 12, 2024 | |
| INVENTOR(S) | : Michelle Straub et al. | |

It is certified that error appears in the above-identified patent and that said Letters Patent is hereby corrected as shown below:

In the Claims

Claim 3, Column 134, Line 32, "NSO" should read --NS0--.

Claim 9, Column 134, Line 47, "NSO" should read --NS0--.

Signed and Sealed this
Thirtieth Day of April, 2024

Katherine Kelly Vidal
*Director of the United States Patent and Trademark Office*